(12) United States Patent
Margulies et al.

(10) Patent No.: US 10,017,525 B2
(45) Date of Patent: Jul. 10, 2018

(54) MULTI-SENSOR ARRAY COMPOUND AND METHODS OF USE THEREOF

(71) Applicant: YEDA RESEARCH AND DEVELOPMENT CO.LTD., Rehovot (IL)

(72) Inventors: David Margulies, Rehovot (IL); Bhimsen Rout, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 477 days.

(21) Appl. No.: 14/414,916

(22) PCT Filed: Jul. 16, 2013

(86) PCT No.: PCT/IL2013/050601
§ 371 (c)(1),
(2) Date: Jan. 15, 2015

(87) PCT Pub. No.: WO2014/013485
PCT Pub. Date: Jan. 23, 2014

(65) Prior Publication Data
US 2015/0232485 A1    Aug. 20, 2015

Related U.S. Application Data

(60) Provisional application No. 61/671,825, filed on Jul. 16, 2012.

(51) Int. Cl.
   *C07F 5/02*      (2006.01)
   *G01N 33/58*    (2006.01)
   *C09B 62/44*    (2006.01)

(52) U.S. Cl.
   CPC .............. *C07F 5/025* (2013.01); *C09B 62/44* (2013.01); *G01N 33/582* (2013.01); *G01N 2400/00* (2013.01); *G01N 2458/30* (2013.01); *G01N 2800/042* (2013.01); *G01N 2800/065* (2013.01); *G01N 2800/067* (2013.01); *G01N 2800/285* (2013.01)

(58) Field of Classification Search
   None
   See application file for complete search history.

(56) References Cited

U.S. PATENT DOCUMENTS

| | | | |
|---|---|---|---|
| 5,503,770 A | 4/1996 | James et al. | |
| 6,916,660 B2 | 7/2005 | Wang et al. | |
| 8,173,437 B2 | 5/2012 | Axford | |
| 2009/0221099 A1 | 9/2009 | Rotello et al. | |

OTHER PUBLICATIONS

Slate et al (1998 JACS 120:4885-6).*
Allardyce et al (2001 Platnium Metals Review 45: 62-9).*
Schwarz et al (1976 Analytical Chemistry 48:524-8.*
Levins et al (2005 JOC 70:9002-8).*
Andreasson et al. "Smart molecules at work—mimicking advanced logic operations", Chem. Soc. Rev., 2010, 39, 174-188.
Anzenbacher et al. "A practical approach to optical cross-reactive sensor arrays", Chem. Soc. Rev., 2010, 39, 3954-3979.
Bencic-Nagala et al. "Microbead Chemical Switches: An Approach to Detection of Reactive Organophosphate Chemical Warfare Agent Vapors", J. Am. Chem. Soc. 2006, 128, 5041-5048.
Bicker et al. "Synthetic lectin arrays for the detection and discrimination of cancer associated glycans and cell lines", Chem. Sci., 2012, 3, 1147-1156.
Buryak et al. "Dynamic Combinatorial Libraries of Dye Complexes as Sensors", Chem. Int. Ed. 2005, 44, 7935-7938.
Chen et al. "Synthesis of the Rheb and K-Ras4B GTPases", vol. 49, Issue 35, pp. 6090-6095, Aug. 16, 2010.
De et al. "Sensing of proteins in human serum using conjugates of nanoparticles and green fluorescent protein", Nature Chemistry vol. 1, Sep. 2009.
De Silva et al. "Molecular logic and computing", Nature Nanotechnology vol. 2, Jul. 2007.

(Continued)

*Primary Examiner* — Christopher M Gross
(74) *Attorney, Agent, or Firm* — Mark S. Cohen; Pearl Cohen Zedek Latzer Baratz LLP

(57) ABSTRACT

The present invention is directed to a multi-sensor array compound including at least three chromophores, at least one receptor and an anchor. Contacting the compound of this invention with an analyte (such as carbohydrate) forms a complex with unique optical signature. The unique optical signature allows differentiating between carbohydrates, diagnosing diseases associated with the carbohydrate, and encoding information in an encoding system.

27 Claims, 27 Drawing Sheets

(56) References Cited

OTHER PUBLICATIONS

Disney et al. "The Use of Carbohydrate Microarrays to Study Carbohydrate-Cell Interactions and to Detect Pathogens", Chemistry & Biology, vol. 11, 1701-1707, Dec. 2004.
Edwards et al. "Boronic Acid Based Peptidic Receptors for Pattern-Based Saccharide Sensing in Neutral Aqueous Media, an Application in Real-Life Samples", J. Am. Chem. Soc. 2007, 129, 13575-13583.
Elfeky "Novel Bronic Acid-Based Fluorescent Sensor for Sugars and Nucleosides", Current Organic Synthesis, vol. 8, No. 6, Jan. 1, 2011, pp. 872-880.
International Search Report for PCT Application No. PCT/IL2013/050601 dated Dec. 6, 2013.
Jagt et al. "Pattern-Based Recognition of Heparin Contaminants by an Array of Self-Assembling Fluorescent Receptors", Chem. Int. Ed. 2009, 48, 1995-1997.
Koshi et al. "A Fluorescent Lectin Array Using Supramolecular Hydrogel for Simple Detection and Pattern Profiling for Various Glycoconjugates", J. Am. Chem. Soc. 2006, 128, 10413-10422.
Larkin et al. "Boronic acid based photoinduced electron transfer (PET) fluorescene sensors for saccharides", New Journal of Chemistry, vol. 34, No. 12, Jan. 1, 2010, p. 2922.
Lin et al. "A Colorimetric Sensor Array for Detection of Triacetone Triperoxide Vapor", J. Am. Chem. Soc. 2010, 132, 15519-15521.
Margulies et al. "Protein Recognition by an Ensemble of Fluorescent DNA G-Quadruplexes", Chem. Int. Ed. 2009, 48, 1771-1774.
McCleskey et al. "Differential Receptors Create Patterns Diagnostic for ATP and GTP", J. Am. Chem. Soc. 2003, 125, 1114-1115.
Miranda et al. "Array-Based Sensing of Proteins Using Conjugated Polymers", J. Am. Chem. Soc. 2007, 129, 9856-9857.
Muller-Graff et al. "Pattern-based sensing of sulfated glycosaminoglycans with a dynamic mixture of iron complexes", Org. Biomol. Chem., 2010, 8, 2327-2331.
Musto et al. "Colorimetric Detection and Identification of Natural and Artificial Sweeteners", Analytical Chemistry, vol. 81, No. 15, Aug. 1, 2009.
Musto et al. "Differential sensing of sugars by colorimetric arrays", Current Opinion in Chemical Biology, vol. 14, No. 6, Dec. 1, 2010, pp. 758-766.
Rout et al. "Medication Detection by a Combinatorial Fluorescent Molecular Sensor", Chem. 2012, 124, 12645-12649.
Schiller et al. "Recognition of phosphosugars and nucleotides with an array of boronic acid appended bipyridinium salts", Analytica Chimica Acta, vol. 627, No. 2, Oct. 10, 2008, pp. 203-211.
Schiller et al. "A Fluorescent Sensor Array for Saccharides Based on Boronic Acid Appended Bipyridinium Salts", Angewandte Chemie, vol. 46, No. 34, Aug. 27, 2007, pp. 6457-6459.
Tian "Data Processing on a Unimolecular Platform", Chem. Int. Ed. 2010, 49, $47^{10}$-$47^{12}$.
Wook et al. "Colorimetric Identification of Carbohydrates by a pH Indicator/pH Change Inducer Ensemble", Chem. Int. Ed. 2006, 45, 6485-6487.
Wright et al. "Differential Receptors Create Patterns That Distinguish Various Proteins", Chem. Int. Ed. 2005, 44, 6375-6378.
Wright et al. "Differential receptor arrays and assays for solution-based molecular recognition", Chem. Soc. Rev., 2006, 35, 14-28.
Yang et al. "Optimizing Cross-reactivity with Evolutionary Search for Sensors", J. Am. Chem.Soc. 2012, 134, 1642-1647.
Zadmard et al. "Nanomolar Protein Sensing with Embedded Receptor Molecules", J. Am. Chem. Soc. 2005, 127, 904-915.
Zaubitzer et al. "Cp Rh-Based Indicator-Displacement Assays for the Identification of Amino Sugars and Aminoglycosides", Chem. Eur. J. 2006, 12, 3928-3934.
Zhang et al. "The Use of Differential Receptors to Pattern Peptide Phosphorylation", J. Am. Chem. Soc. 2009, 131, 11976-11984.
Zhang et al. "Discrimination and Classification of Ginsenosides and Ginsengs Using Bis- Boronic Acid Receptors in Dynamic Multicomponent Indicator Displacement Sensor Arrays", Chem. Eur. J. 2012, 18, 1102-1110.
Zhou et al. "Pattern Recognition of Proteins Based on an Array of Functionalized Porphyrins", J. Am. Chem. Soc. 2006, 128, 2421-2425.
Zyryanov et al. "Rational Design of a Fluorescence-Turn-On Sensor Array for Phosphates in Blood Serum", Chem. Int. Ed. 2007, 46, 7849-7852.

\* cited by examiner

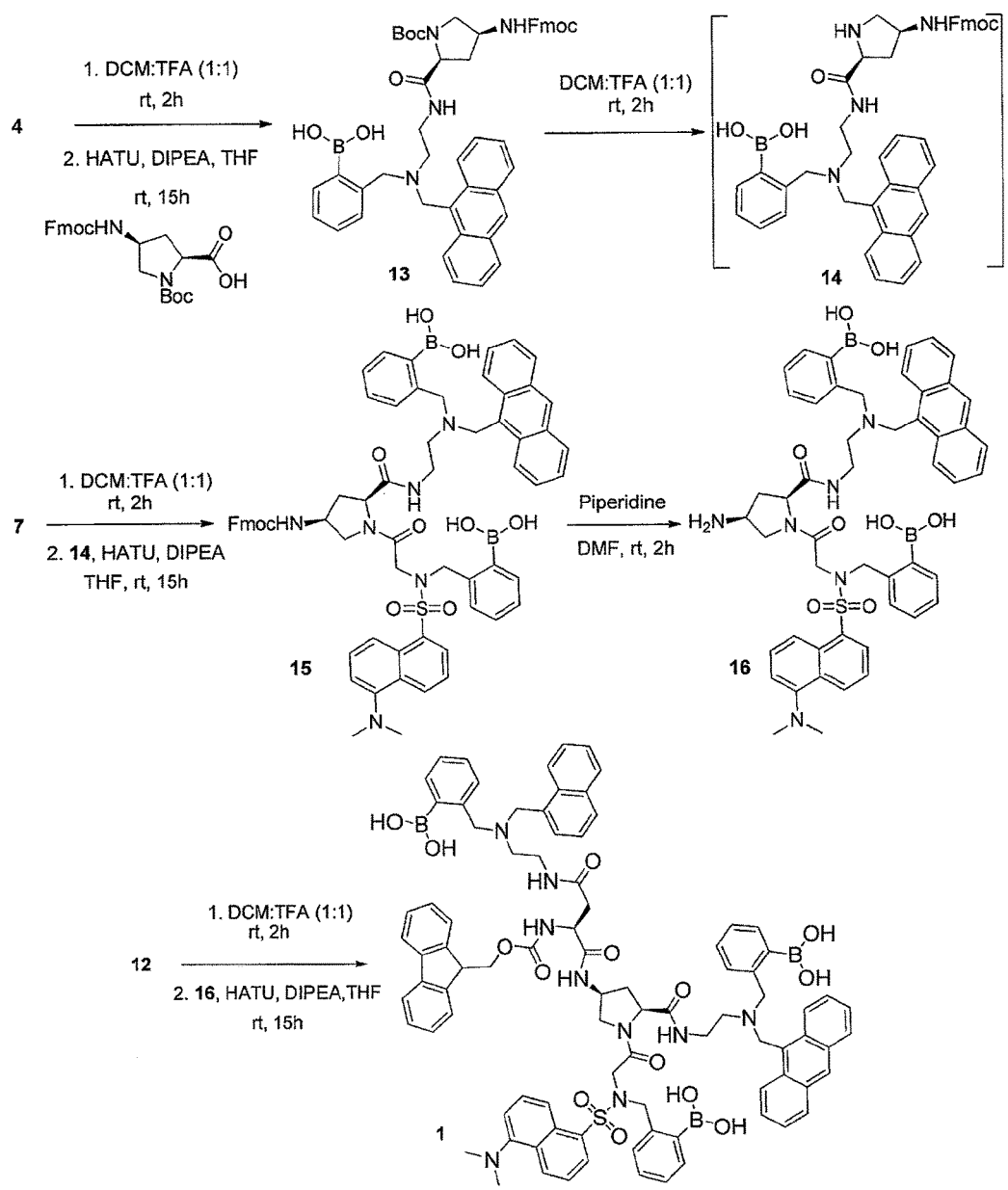
FIGURE 1-CONT.

1) None; 2) Ouabain; 3) Digoxin; 4) Digoxin (2 fold); 5) Digitoxin; 6) Erythromycin; 7) Roxithromycin; 8) Clarithromycin; 9) Azithromycin; 10) Hygromycin; 11) Amikacin; 12) Rifampicin; 13) Rifabutin.

Structures of Drugs

Digoxin　　　　　　　　　　　Digitoxin

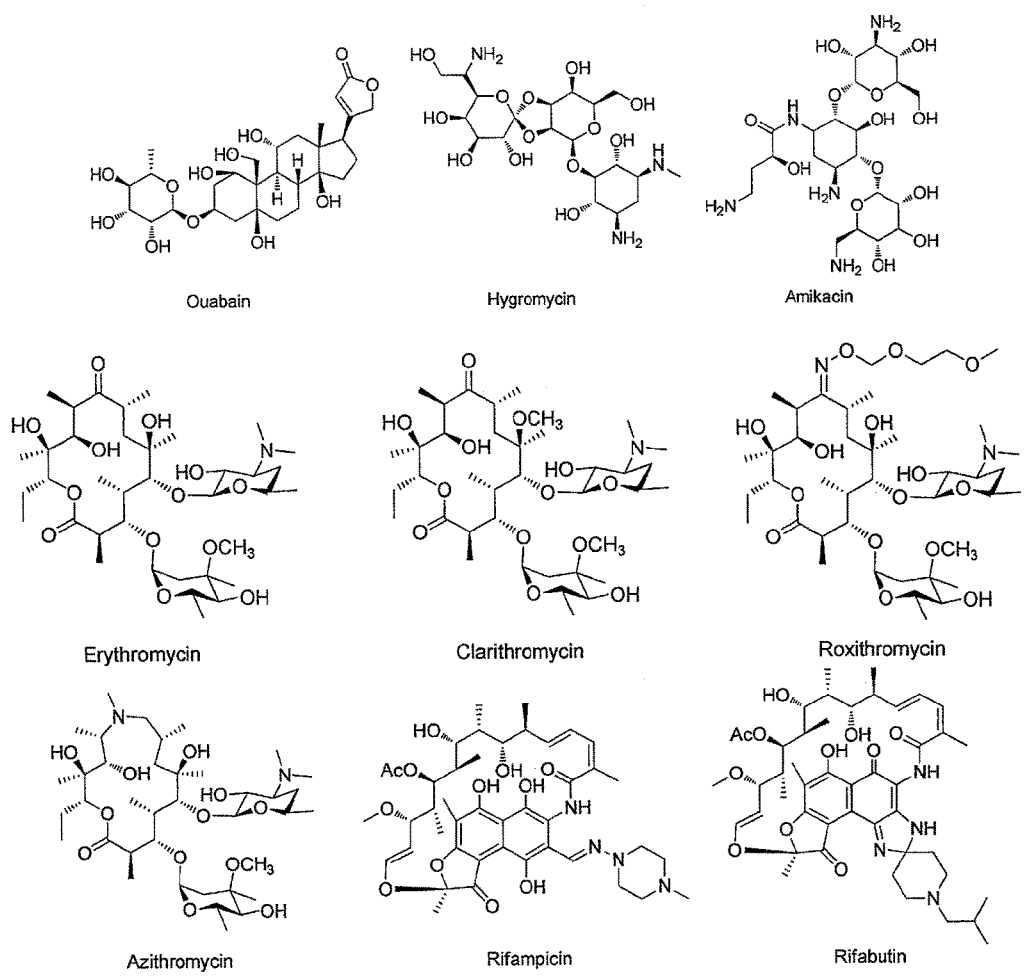
FIGURE 11-CONT

Table 2: All Possible Combination Codes of a Three State Molecular encoding System

| 1 key | 2-keys (1, 2) | 2-keys (1, 3) | 2-keys (2, 3) | 3-keys (1, 2, 3) |
|---|---|---|---|---|
| a. 111 | d. 112 | e. 113 | f. 223 | j. 123 |
| b. 222 | 121 | 131 | 232 | 132 |
| c. 333 | 211 | 311 | 322 | 213 |
|  | g. 122 | h. 133 | i. 233 | 231 |
|  | 212 | 313 | 323 | 312 |
|  | 221 | 331 | 332 | 321 |

Figure 20

MULTI-SENSOR ARRAY COMPOUND AND METHODS OF USE THEREOF

CROSS-REFERENCE TO RELATED APPLICATIONS

This application is a National Phase Application of PCT International Application No. PCT/IL2013/050601, International Filing Date Jul. 16, 2013, claiming priority of U.S. Patent Application No. 61/671,825, filed Jul. 16, 2012 which are hereby incorporated by reference in their entirely.

FIELD OF THE INVENTION

The present invention is directed to a multi-sensor array compound including at least three chromophores, at least one receptor and an anchor. Contacting the compound of this invention with an analyte (such as carbohydrate) forms a complex with unique optical signature. The unique optical signature allows differentiating between carbohydrates, diagnosing diseases associated with the carbohydrate, and encoding information in an encoding system.

BACKGROUND OF THE INVENTION

Colorimetric or fluorescent molecular sensors triggered by several input signals are applied as molecular computation and analytical devices. Such sensors can imitate the function of electronic logic gates, digital circuits; arithmetic and security systems, as well as be applied in multiplexed cellular imaging, in clever chemosensing, and as molecular tags. Such sensors require a receptor-per-target, which significantly limits their multiplicity.

In order to obtain multi-analyte detection using fluorescent or colorimetric molecular sensors cross-responsive arrays are required similar to the mammalian olfactory system. An artificial nose, typically includes two components, an array of chemical sensors and a pattern-recognizer. The array may mimic the operation of the olfactory neural system and can identify complex vapors and aromas as well as analyze disease biomarkers. State-of-the-art developments in supramolecular analytical chemistry afforded colorimetric and fluorescent molecular sensor arrays that can operate in biochemical solutions. Developing methods for verifying drug content at a point-of-care is receiving growing international attention. Unlike any other class of biosensors, such arrays can detect, identify, and discriminate among specific mixtures containing possibly hundreds of different chemical species or between structurally similar biomolecules including phosphates, steroids, saccharides, nucleotide phosphates, peptides, and proteins in a high-throughput manner.

For example, macrolides, aminoglycosides, and rifampycins are large families of antibiotics whose counterfeits are highly prevalent in the developing world. Cardiac glycosides, used for treating heart conditions, have been associated with substandard medication in developed countries and are often involved in medication errors due to their narrow therapeutic window and adverse drug interactions.

Glycans play diverse and crucial roles in several biological processes. Most plasma membrane and secretory proteins are glycosylated.

The presence and/or irregular concentrations of glycans can be a sign for various diseases such as multiple sclerosis, crohn's disease, autoimmune disease, colitis, inflammatory bowl disease, cancer, lysosomal storage disease and celiac. Some inherited and nongenetic diseases results of alterations of the glycan structures. Sensitive, convenient and precise glycan-sensing methods provide crucial tools for the early diagnosis of diseases and successful treatments of patients. Therefore, selective sugar detection is a challenging problem.

Although every sensor in an array may respond to a given chemical or mixture of chemicals differently, the pattern recognizer evaluates the responses and through predetermined, programmed, or learned patterns the pattern-recognizer compares the unique pattern or "fingerprints" of the measurements to stored patterns for known chemical species for identifying and quantifying of the species chemical.

Fluorescent or colorimetric molecular sensors have the ability to recognize various biologically compounds, specific and mixtures of chemicals and detect disease biomarkers. Fluorescent or colorimetric molecular sensors are among the most powerful analytical tools used in cell biology. Cell-permeable molecules that combine a receptor and a fluorophore allow one to sense specific ions or biomolecules in their native environments and to better understand their role in various cell signalling pathways.

A combinatorial fluorescent molecular sensor mimics the operation of optical cross-reactive sensor arrays (the so-called artificial "nose/tongues"). The sensor integrates different non-specific fluorescent receptors (e.g. boronic acid-dye conjugates) and utilizes photo-induced electron transfer (PET), internal charge transfer (ICT), and fluorescence resonance energy transfer (FRET) for generating distinguishable emission patterns for different carbohydrate-based drugs and their combinations.

Specifically, combinatorial sensing devices that, similar to small fluorescent molecules, could operate in a microscopic world might eventually be able to provide insight into the dynamics of bioanalyte combinations within cells, information that cannot be obtained from conventional fluorescent sensors.

Further, a combinatorial fluorescent molecular sensor can operate as a highly efficient molecular security/encoding system. The ability of a pattern-generating molecule to process diverse sets of chemical inputs, discriminate between their concentrations and form multivalent and kinetically-stable complexes, is a powerful tool for processing a wide range of chemical 'passwords' at different lengths. Such system results in unbreakable combination locks at a molecular scale.

Similar to the electronic devices, the molecular encoding system can respond to diverse input and authorize multiple password entries.

The subject Application is directed to molecular size array for use of differential sensing at the molecular-scale as well as within confined microscopic spaces such as cells. Specifically, sensing saccharides.

SUMMARY OF THE INVENTION

In one embodiment, this invention is directed to a compound comprising an array of at least three chromophores, at least one receptor and an anchor, wherein binding said receptor to an analyte forms a complex with unique optical signature.

In one embodiment, this invention is directed to a compound represented by the structure of compound 1:

(1)

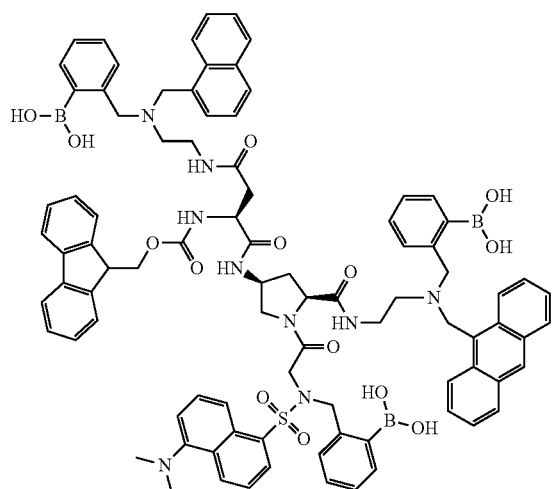

(III)

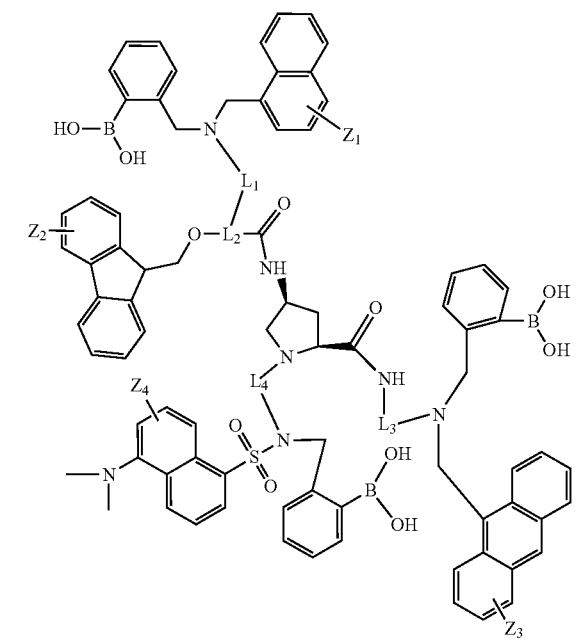

In one embodiment, this invention is directed to a method of differentiating between carbohydrates comprising:

contacting a carbohydrate with a compound in a liquid medium, wherein said carbohydrate and said compound form a complex; wherein said compound comprises an array of at least three chromophores, at least one boronic acid receptor and an anchor; wherein contacting said carbohydrate with said compound results in a conformational change of said compound and thereby to a unique optical signature of said complex; and measuring the optical signature of said complex;

and thereby, differentiating said carbohydrate.

In one embodiment, this invention is directed to a method of diagnosing a disease in a subject, wherein said diagnosis comprises detection of a carbohydrate biomarkers; said method comprising:

collecting a biological sample from a subject;

optionally isolating components from said biological sample;

contacting a compound with a carbohydrate comprised within said sample or within isolated component in a liquid medium; wherein said carbohydrate forms a complex with said compound; wherein said compound comprises an array of at least three chromophores, at least one boronic acid receptor and an anchor; wherein contacting said compound with said carbohydrate results in a conformational change of said compound and thereby to a unique optical signature of said complex;

measuring the optical signature of said complex;

identifying a carbohydrate biomarker in said sample, said carbohydrate biomarker being characteristic of a disease; or measuring a change in a concentration of a carbohydrate biomarker in said sample compared to normative values, wherein said change is characteristic of a disease;

thereby, diagnosing a disease in a subject.

In one embodiment, this invention is directed to an encoding system for encoding information using a complex of a compound represented by the structure of formula (III):

wherein
$L_1$, $L_2$, $L_3$, $L_4$ are independently a linker, wherein said linker is -alkylene-, —O-alkylene-, —NHC(O)—, —C(O)NH—, —NHC(O)X—, —C(O)NHX—, —C(O)X—, —X'NHC(O)—, —X'C(O)NH—, —X'NHC(O)X—, —X'C(O)NHX—, —X'C(O)X—, —NHX—, —NH-[amino-acid]-C(O)—, —NH-[amino-acid]-C(O)-alkylene-, —C(O)-[amino-acid]-NH—, or —C(O)-[amino-acid]-NH-alkylene-;

X and X' are independently alkylene, haloalkylene, arylene or phenylene; and $Z_1$, $Z_2$, $Z_3$, $Z_4$ are independently hydrogen, alkyl, alkenyl, haloalkyl, aryl, O-aryl, —$(CH_2)$n-aryl, cycloalkyl, O-cycloalkyl, $CF_3$, F, I, Br, Cl, $NO_2$, CN, $N(R')_2$, COOH, CUR', NHCOR', CONHR', $(CH_2)_nNH_2$, $(CH_2)_nNHR'$, SR', SH, OR', $(CH_2)_nOH$, $(CH_2)_nCOOH$, or OH; wherein R' is H, alkyl, haloalkyl, dihaloalkyl, trihaloalkyl, aryl, phenyl or halogen; and n is from 0 to 8;

and between 2 and 7 analytes in a specific sequence, wherein said complex exhibits a unique optical signature signal;

said encoding system comprising:

a data processor;

a non-transitory database storage device for storing a plurality of database records;

a chemical process interface, for controlling chemical processes binding analytes to the compound; and a spectroscopic interface, for reading unique optical signatures of the complex.

In one embodiment, this invention is directed to a method of encoding information using a compound represented by the structure of formula (III), (III)

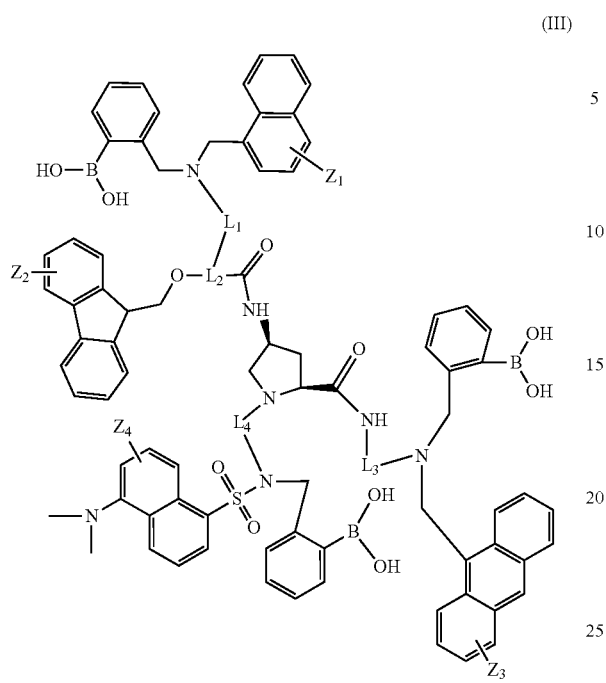

wherein
- $L_1$, $L_2$, $L_3$, $L_4$ are independently a linker, wherein said linker is -alkylene-, —O-alkylene-, —NHC(O)—, —C(O)NH—, —NHC(O)X—, —C(O)NHX—, —C(O)X—, —X'NHC(O)—, —X' C(O)NH—, —X'NHC(O)X—, —X' C(O)NHX—, —X' C(O)X—, —NHX—, —NH-[amino-acid]-C(O)—, —NH-[amino-acid]-C(O)-alkylene-, —C(O)-[amino-acid]-NH—, or —C(O)-[amino-acid]-NH-alkylene-;
- X and X' are independently alkylene, haloalkylene, arylene or phenylene; and
- $Z_1$, $Z_2$, $Z_3$, $Z_4$ are independently hydrogen, alkyl, alkenyl, haloalkyl, aryl, O-aryl, —(CH$_2$)n-aryl, cycloalkyl, O-cycloalkyl, CF$_3$, F, I, Br, Cl, NO$_2$, CN, N(R')$_2$, COOH, COR', NHCOR', CONHR', (CH$_2$)$_n$NH$_2$, (CH$_2$)$_n$NHR', SR', SH, OR', (CH$_2$)$_n$OH, (CH$_2$)$_n$COOH, or OH; wherein R' is H, alkyl, haloalkyl, dihaloalkyl, trihaloalkyl, aryl, phenyl or halogen; and
- n is from 0 to 8;

the method comprising:
a) contacting said compound with between 2 and 7 analytes in a specific sequence to form a complex, wherein said complex exhibits a unique optical signature signal;
b) reading the unique optical signature;
c) associating the unique optical signature with an encoded reference specifying said analytes contacted in said specific sequence according to a predefined encoding scheme; and
d) storing the encoded reference keyed to the unique optical signature in a database record.

In one embodiment, this invention is directed to a method of decoding encoded information using a compound represented by the structure of formula (III):

(III)

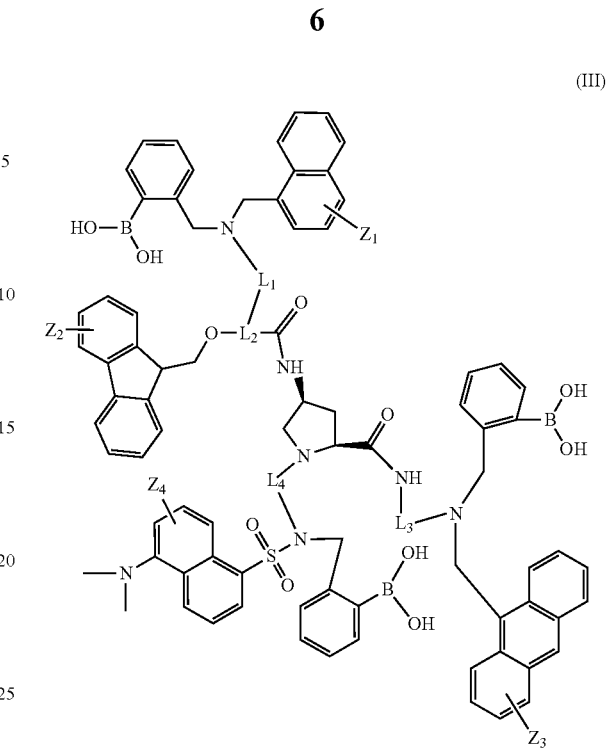

wherein
- $L_1$, $L_2$, $L_3$, $L_4$ are independently a linker, wherein said linker is -alkylene-, —O-alkylene-, —NHC(O)—, —C(O)NH—, —NHC(O)X—, —C(O)NHX—, —C(O)X—, —X'NHC(O)—, —X'C(O)NH—, —X'NHC(O)X—, —X'C(O)NHX—, —X'C(O)X—, —NHX—, —NH-[amino-acid]-C(O)—, —NH-[amino-acid]-C(O)-alkylene-, —C(O)-[amino-acid]-NH—, or —C(O)-[amino-acid]-NH-alkylene-;
- X and X' are independently alkylene, haloalkylene, arylene or phenylene; and
- $Z_1$, $Z_2$, $Z_3$, $Z_4$ are independently hydrogen, alkyl, alkenyl, haloalkyl, aryl, O-aryl, —(CH$_2$)n-aryl, cycloalkyl, O-cycloalkyl, CF$_3$, F, I, Br, Cl, NO$_2$, CN, N(R')$_2$, COOH, COR', NHCOR', CONHR', (CH$_2$)$_n$NH$_2$, (CH$_2$)$_n$HR', SR', SH, OR', (CH$_2$)$_n$OH, (CH$_2$)$_n$COOH, or OH; wherein R' is H, alkyl, haloalkyl, dihaloalkyl, trihaloalkyl, aryl, phenyl or halogen; and
- n is from 0 to 8;

the method comprising:
a) contacting said compound with between 2 and 7 analytes in a specific sequence to form a complex, wherein said complex exhibits a unique optical signature signal;
b) reading the unique optical signature of the compound; and
c) accessing a database record keyed to the unique optical signature to obtain a code corresponding to a complex of said analytes bound to said compound.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 20 provides Table 2 which includes all possible combination codes of a three state encoding system.

Figure 1:
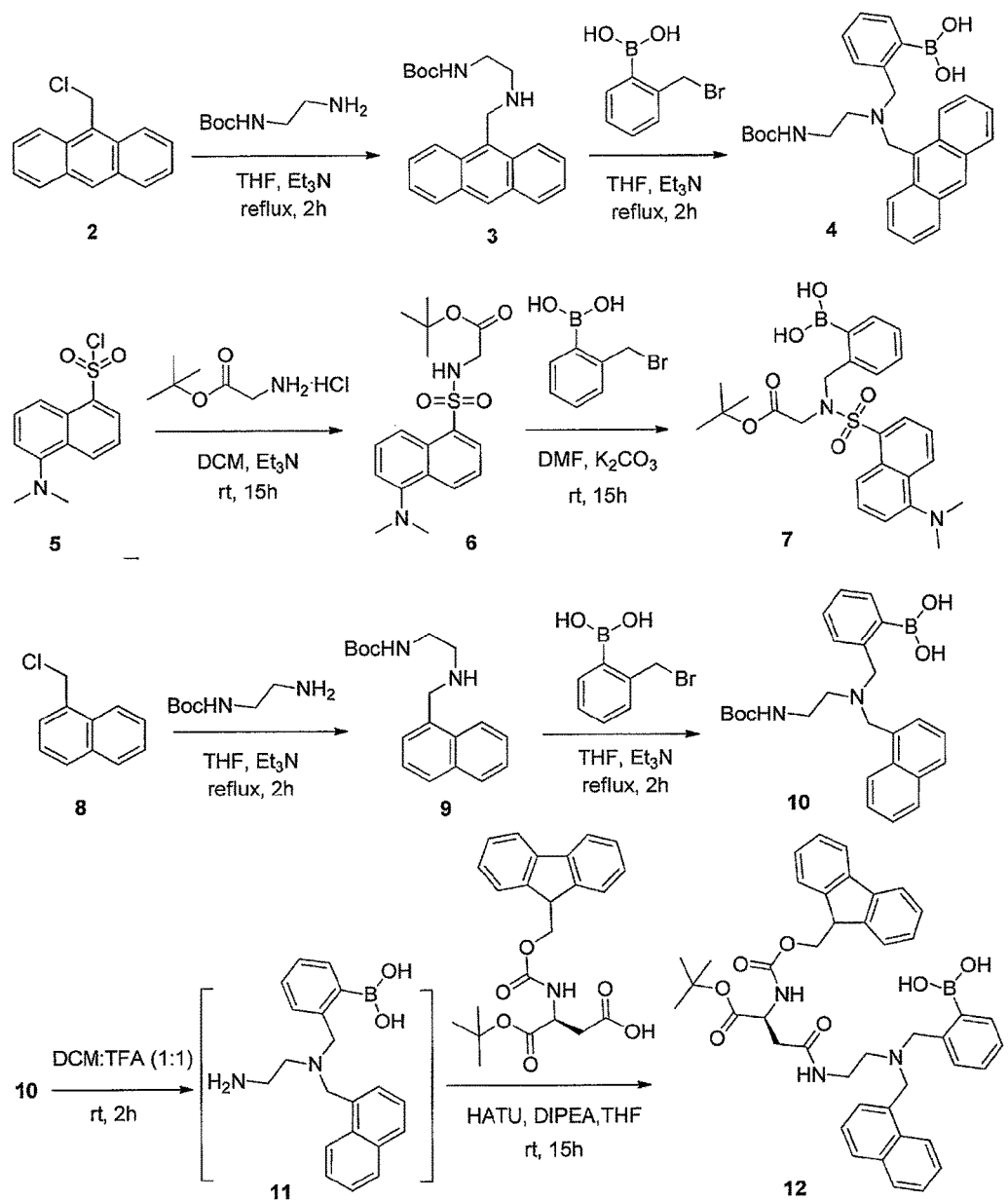
FIG. 1 depicts a synthetic scheme of a monomolecular differential sensor of compound 1.
Figure 2:
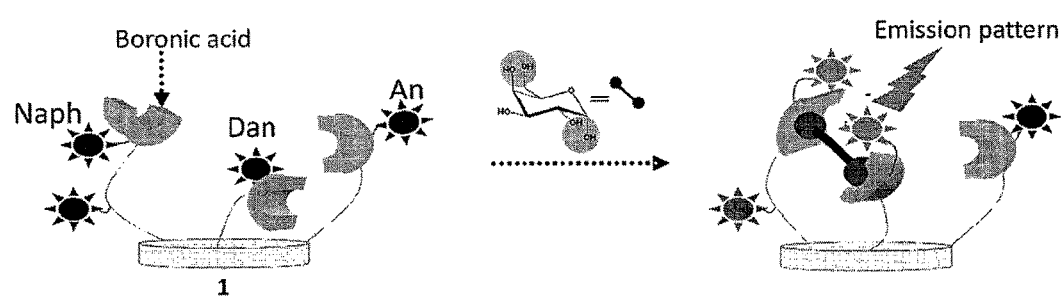
FIG. 2 depicts a schematic illustration of the sensor function. A unique emission pattern for each saccharide can be generated due to direct optical responses of each dye, as well as conformational changes that affect fluorescence resonance energy transfer (FRET) processes among them.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention is directed to a compound comprising an array of at least three chromophores, at least one receptor and an anchor, wherein binding said receptor to an analyte forms a complex with unique optical signature.

In one embodiment, this invention is directed to a compound comprising an array of at least three fluorescent dyes, at least one boronic acid receptor and an anchor, wherein binding said receptor to an analyte forms a complex with unique optical signature.

In one embodiment, this invention is directed to a complex comprising a compound and an analyte, wherein said compound comprises an array of at least three chromophores, at least one receptor and an anchor. In another embodiment, the complex has unique optical signature.

In one embodiment, this invention is directed to a complex comprising a compound and an analyte, wherein said compound comprises an array of at least three fluorescent dyes, at least one boronic acid receptor and an anchor. In another embodiment, the complex has unique optical signature.

In one embodiment, the compound of this invention includes a receptor. In one embodiment, the compound of the invention includes at least one receptor. In one embodiment, the compound of this invention includes one receptor. In another embodiment, the compound of this invention includes two receptors. In another embodiment, the compound of this invention includes three receptors. In one embodiment, the compound of this invention includes four receptors. In another embodiment, the compound of this invention includes more than four receptors, e.g., 5, 6, 7, or 8. In another embodiment, the receptor of this invention is boronic acid, phenyl-boronic acid, naphthyl-boronic acid. Boronic acid or derivatives thereof is a good receptor for diols. Specifically, boronic acid is a good receptor for saccharides or carbohydrates since boronic acid is able to react with 1,2- or 1,3-diols to form five- or six-membered rings respectively. In another embodiment, the receptor is Zn(II)-dipicolylamine (Zn-DPA). Zn-DPA and derivative thereof are receptors for phosphates, phosphate anion, and can be used as phosphate-selective chemosensor. The phosphate anion plays an important role in vivo such as in signal transmission system, recognition of an intracellular phosphorylation signal, and can be used as a tool in cell biology and analysis of a number of in vivo processes.

In another embodiment, the receptor of this invention is hydroxamate. Hydroxamate is a good receptor for transition metal ions such as $Fe^{3+}$, $Cu^{2+}$, $Cd^{2+}$, $Zn^{2+}$, Pb2+, $VO^+$ or lanthanide ions.

In another embodiment, the receptor of this invention is porphyrin, bypyridyl, crown-ether or derivative thereof. Porphyrin, bypyridyl, crown-ether or derivatives thereof are receptors for metal ions. In another embodiment crown-ether is a receptor for alkaline metal ions.

Figure 16A:
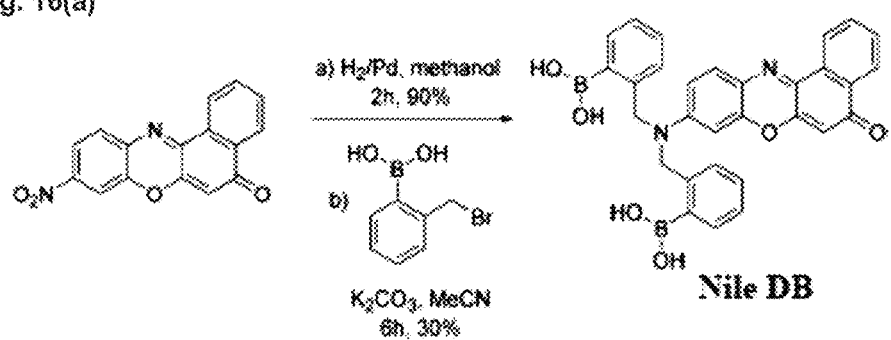
FIG. 16 depicts. a) Synthetic steps for preparing Nile-DB; b) a photograph of Nile-DB prior to and after the addition of glucose; c) emission spectra generated by 400 nM of Nile-DB (red) upon addition of 5 mM D-glucose (green), D-fructose (purple), and sucrose (blue). Excitation: 530 nm.

In one embodiment, this invention is directed to a compound and methods of use thereof. The compound of this invention includes at least three chromophores. Non limiting examples of chromospheres include conjugated systems, aromatic rings (benzene, naphthalene, anthracene, tetracene, and perylene), chlorophyll's porphyrin ring (metal complex chromophores) or an azo dye's benzene rings. In another embodiment the chromophore is a fluorescent dye. In another embodiment, the compound of this invention includes at least three fluorescent dyes. In another embodiment, the compound of this invention includes between 2 to 10 fluorescent dyes. In another embodiment, the compound includes two fluorescent dyes. In another embodiment, the compound includes three fluorescent dyes. In another embodiment, the compound includes four fluorescent dyes. In another embodiment, the compound includes five fluorescent dyes. In another embodiment, the compound includes six fluorescent dyes. In another embodiment, the fluorescent dyes are different. In another embodiment, the fluorescent dyes are the same, derivatives or different. In another embodiment, the fluorescent dye is substituted or unsubstituted anthracene; substituted or unsubstituted nile red; substituted or unsubstituted dansyl; substituted or unsubstituted fluorenyl; substituted or unsubstituted naphthalene; substituted or unsubstituted tetracene; substituted or unsubstituted perylene; substituted or unsubstituted pyrene substituted or unsubstituted fluorescein; substituted or unsubstituted rhodamine; substituted or unsubstituted cyanine, substituted or unsubstituted coumarin; or any other fluorescent dye known in the art and/or disclosed in http://www.fluorophores.org which is incorporated herein by reference. In another embodiment, the fluorescent dye of this invention is anthracene, naphthalene, fluorenyl, dansyl, nile red, fluorescein, rhodamine, perylene, cyanine, coumarine, derivative thereof, or combination thereof. In another embodiment, the fluorescent dye of this invention is substituted or unsubstituted red and NIR-emitting dyes as described in FIG. 13, for example, substituted or unsubstituted TAMRA, substituted or unsubstituted Cy3, substituted or unsubstituted BODIPY, substituted or unsubstituted Nile Red, substituted or unsubstituted Alexa Fluor, substituted or unsubstituted Dy 630, substituted or unsubstituted Cy5, substituted or unsubstituted Cy7, substituted or unsubstituted Sulfo Cy7, substituted or unsubstituted Cy7.5, substituted or unsubstituted Nd3+-Texas Red, and substituted or unsubstituted Fr3+-Fluorescein. In one embodiment, the fluorescent dye of this invention is substituted or unsubstituted Nile DB as illustrated in FIG. 16(a).

In another embodiment, the fluorescent dye of this invention is substituted by one to three substituents. In another embodiment the fluorescent dye is substituted by alkyl, alkenyl, haloalkyl, aryl, O-aryl, —$(CH_2)$n-aryl, cycloalkyl, O-cycloalkyl, $CF_3$, F, I, Br, Cl, $NO_2$, CN, $N(R')_2$, COOH, COR', NHCOR', CONHR', $(CH_2)_nNH_2$, $(CH_2)_nNHR'$, SR', SH, OR', $(CH_2)_nOH$, $(CH_2)_nCOOH$, or OH; wherein R' is H, alkyl, haloalkyl, dihaloalkyl, trihaloalkyl, aryl, phenyl or halogen and n is between 0 to 8. In another embodiment n is between 1 to 6.

In one embodiment, this invention is directed to a compound and methods of use thereof. The compound of this invention includes an anchor. In another embodiment the chromophore and the receptor are covalently attached to the anchor via a linker. In another embodiment, the anchor of the compound of this invention is chiral. In another embodiment, the anchor of the compound of this invention is cis-amino-L proline. In another embodiment, the anchor of the compound of this invention is trans-amino-L proline. In another embodiment, the anchor of the compound of this invention is cis-amino-D proline or trans-amino-D proline. In another embodiment, the anchor is an aryl. In another embodiment, the anchor of the compound of this invention is proline, phenyl, bi-phenyl, naphthalene, alkyl, cyclohexane derivative, piperidine carboxylic acid derivative, cyclodextrin derivative, histidine derivative or an amino-acid.

In one embodiment, the compound of this invention comprises a chromophore, a receptor and an anchor, wherein the chromophore is attached to an anchor via a linker, wherein the linker comprises nitrogen. In another embodiment, the nitrogen is in vicinity to the receptor. In another embodiment, a receptor is conjugated to a chromophore (or dye), thereby forming a receptor-dye conjugate. In another embodiment, boronic acid is conjugated to a receptor forming a boronic acid-dye conjugate. In another embodiment, the conjugation between the receptor (i.e. boronic acid) and the chromophore (i.e dye) is via a nitrogen atom. In another embodiment, the compound of this invention includes between 3 to 4 conjugates which are linked to the anchor.

In one embodiment, the compound of this invention comprises at least three chromophores, for example, 3, or 4, or 5, at least one receptor, for example, 1, 2, 3, 4, or 5, and at least one anchor, for example 1, 2, or 3. In another embodiment, the compound of this invention comprises at least three chromophores, at least three receptors, and at least one anchor. In one embodiment, the compound of this invention comprises three chromophores, three receptors, and one anchor. In anther embodiment, the compound of this invention comprises four chromophores, four receptors, and one anchor. In anther embodiment, the compound of this invention comprises four chromophores, three receptors, and one anchor. In anther embodiment, the compound of this invention comprises three chromophores, four receptors, and one anchor.

In one embodiment, the compound of this invention comprises a fluorescent dye, a boronic acid receptor and an anchor, wherein the fluorescence dye is attached to an anchor via a linker, wherein the linker comprises nitrogen. In another embodiment, the nitrogen is in vicinity to the boronic acid receptor.

In one embodiment, the complex, compound, encoding system and method of this invention make use of an analyte. In another embodiment, the analyte of this invention is a phosphate anion. In another embodiment, the analyte of this invention is a metal ion. In another embodiment, the analyte of this invention is a toxic gas. In another embodiment, the analyte is a drug. In another embodiment, the analyte is an explosive, in another embodiment, the analyte is an amino acid. In another embodiment, the analyte is a protein. In another embodiment, the analyte of this invention is a carbohydrate.

A "carbohydrate" of this invention refers to an organic compound that consists only of carbon, hydrogen, and oxygen and optionally nitrogen with at least one hydroxyl group, in another embodiment including diol. In another embodiment a carbohydrate include 1,2 diol or a 1,3 diol or combination thereof. In another embodiment the carbohydrate is a saccharide. In another embodiment the carbohydrate is L-Glucose, D-Glucose, D-fructose, L-fructose, D-arabinose, D-xylose, L-xylose, L-mannose, D-galactose, D-sorbitol, mannitol, dulcitol, adonitol, xylitol, L-threitol, maltitol, lactulose, D-lactose, D-maltose, D-trehalose maltotriose or combination thereof. In another embodiment, the carbohydrate of this invention is monosaccharide. In another embodiment, the carbohydrate of this invention is disaccharide. In another embodiment, the carbohydrate of this invention is polysaccharide. In another embodiment, the carbohydrate of this invention is glycan. In another embodiment, the carbohydrate of this invention is glycoprotein. In another embodiment, the carbohydrate of this invention is a proteoglycan. In another embodiment, the carbohydrate is an antibiotic. In another embodiment, the carbohydrate is a macrolide, aminoglycoside or cardiac glycoside antibiotics. In another embodiment, the carbohydrate is ouabain, digoxin, digitoxin, erythromycin, roxithromycin, clarithromycin, azithromycin, hygromycin, amikacin, rifampicin, rifabutin, or combination thereof.

In one embodiment, this invention is directed to a compound of formula I or its isomer:

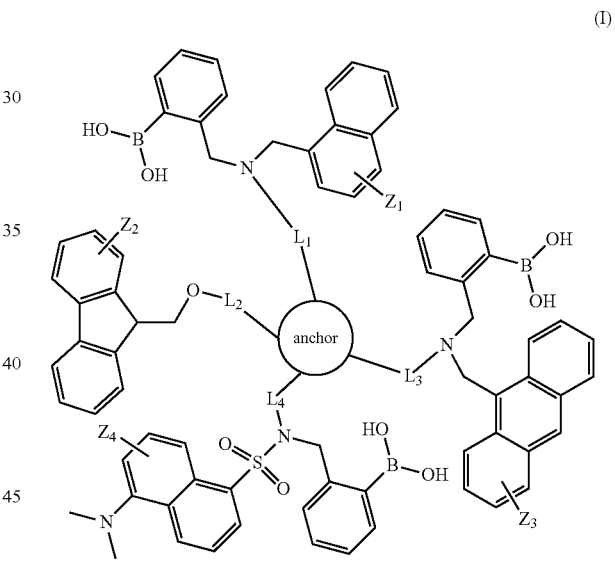

(I)

wherein
the anchor is cis-amino-L proline, trans-amino-L proline, cis-amino-D proline or trans-amino-D proline;
$L_1$, $L_2$, $L_3$, $L_4$ are independently a linker, wherein said linker is -alkylene-,
—O-alkylene-, —NHC(O)X—, —C(O)NHX—, —C(O)X—, —X'NHC(O)—, —X'C(O)NH—, —X'NHC(O)X—, —X' C(O)NHX—, —X' C(O)X—, —NHX—, —NH-[amino-acid]-C(O)—, —NH-[amino-acid]-C(O)-alkylene-, —C(O)-[amino-acid]-NH— or —C(O)-[amino-acid]-NH-alkylene-;
X and X' are independently an alkylene, haloalkylene, aryl or phenyl; and
$Z_1$, $Z_2$, $Z_3$, $Z_4$ are independently hydrogen, alkyl, alkenyl, haloalkyl, aryl, O-aryl, —(CH$_2$)n-aryl, cycloalkyl, O-cycloalkyl, CF$_3$, F, I, Br, Cl, NO$_2$, CN, N(R)$_2$, COOH, COR', NHCOR', CONHR', (CH$_2$)$_n$NH$_2$, (CH$_2$)$_n$NHR', SR', SH, OR', (CH$_2$)$_n$OH, (CH$_2$)$_n$COOH, or OH; wherein R' is H, alkyl, haloalkyl, dihaloalkyl, trihaloalkyl, aryl, phenyl or halogen and n is between 0 to 8. In another embodiment n is between 1 to 6.

In one embodiment, this invention is directed to a compound of formula II or its isomer:

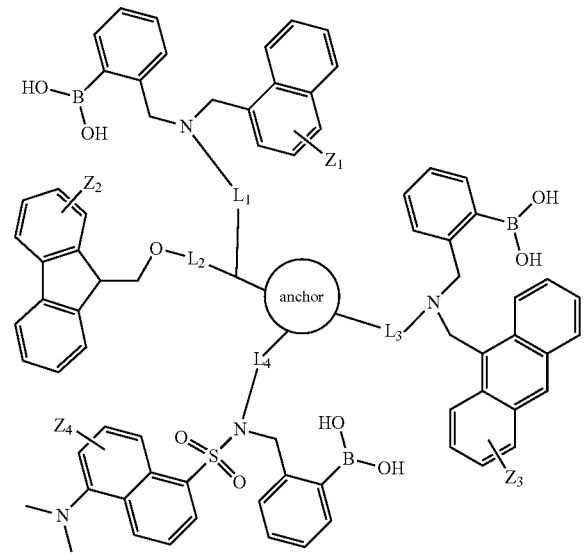

(II)

wherein the anchor is cis-amino-L prolyne, trans-amino-L prolyne, cis-amino-D prolyne or trans-amino-D prolyne;

$L_1, L_2, L_3, L_4$ are independently a linker, wherein said linker is -alkylene-, —O-alkylene-, —NHC(O)X—, —C(O)NHX—, —C(O)X—, —X'NHC(O)—, —X'C(O)NH—, —X'NHC(O)X—, —X'C(O)NHX—, —X' C(O)X—, —NHX—, —NH-[amino-acid]-C(O)—, —NH-[amino-acid]-C(O)-alkylene-, —C(O)-[amino-acid]-NH— or —C(O)-[amino-acid]-NH-alkylene-;

X and X' are independently an alkylene, haloalkylene, aryl or phenyl; and $Z_1, Z_2, Z_3, Z_4$ are independently hydrogen, alkyl, alkenyl, haloalkyl, aryl, O-aryl, —(CH$_2$)n-aryl, cycloalkyl, O-cycloalkyl, CF$_3$, F, I, Br, Cl, NO$_2$, CN, N(R)$_2$, COOH, COR', NHCOR', CONHR, (CH$_2$)$_n$NH$_2$, (CH$_2$)$_n$NHR', SR', SH, OR', (CH$_2$)$_n$OH, (CH$_2$)$_n$COOH, or OH; wherein R' is H, alkyl, haloalkyl, dihaloalkyl, trihaloalkyl, aryl, phenyl or halogen and n is between 0 to 8. In another embodiment n is between 1 to 6.

In one embodiment, if L$_2$ of formula II is —NH-[amino-acid]-C(O)—, —NH-[amino-acid]-C(O)-alkylene-, —C(O)-[amino-acid]-NH— or —C(O)-[amino-acid]-NH-alkylene- then L$_1$ is attached to L$_2$ via the residue of the amino acid.

In one embodiment, this invention is directed to a compound of formula III or its isomer:

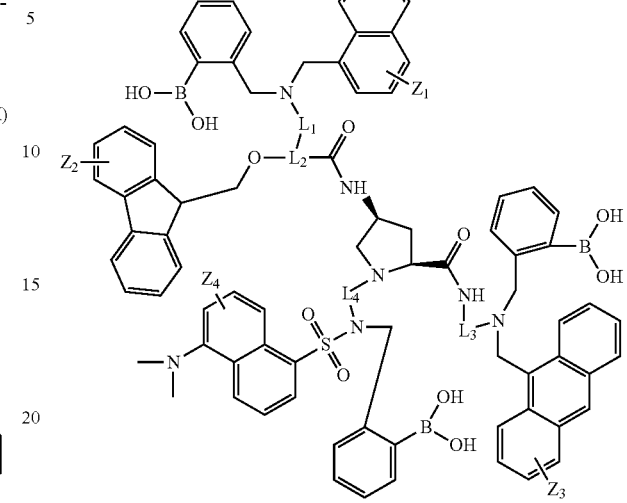

(III)

wherein $L_1, L_2, L_3, L_4$ are independently a linker, wherein said linker is -alkylene-, —O-alkylene-, NHC(O)—, —C(O)NH—, —NHC(O)X—, —C(O)NHX—, —C(O)X—, —X'NHC(O)—, —X'C(O)NH—, —X'NHC(O)X—, —X'C(O)NHX—, —X'C(O)X—, —NHX—, —NH-[amino-acid]-C(O)—, —NH-[amino-acid]-C(O)-alkylene-, —C(O)-[amino-acid]-NH—, or —C(O)-[amino-acid]-NH-alkylene-;

X and X' are independently an alkylene, haloalkylene, aryl or phenyl; and $Z_1, Z_2, Z_3, Z_4$ are independently hydrogen, alkyl, alkenyl, haloalkyl, aryl, O-aryl, —(CH$_2$)n-aryl, cycloalkyl, O-cycloalkyl, CF$_3$, F, I, Br, Cl, NO$_2$, CN, N(R')$_2$, COOH, COR', NHCOR', CONHR', (CH$_2$)$_n$NH$_2$, (CH$_2$)$_n$NHR', SR', SH, OR', (CH$_2$)$_n$OH, (CH$_2$)$_n$COOH, or OH; wherein R' is H, alkyl, haloalkyl, dihaloalkyl, trihaloalkyl, aryl, phenyl or halogen and n is between 0 to 8. In another embodiment n is between 1 to 6.

In one embodiment, this invention is directed to a compound of formula IV or its isomer:

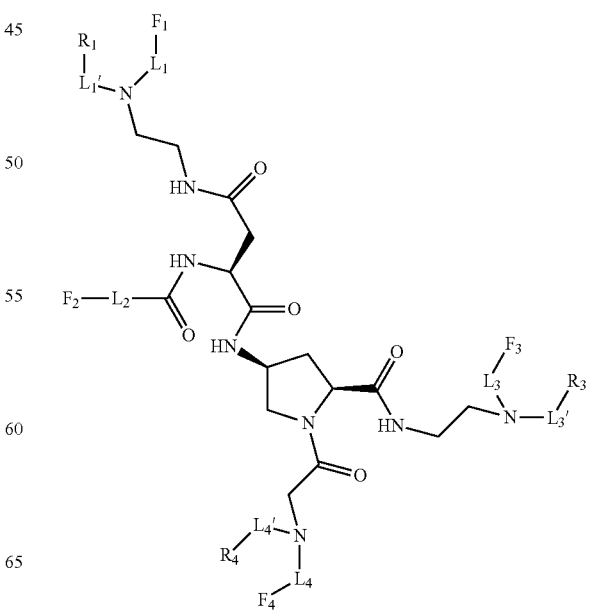

(IV)

wherein
L₁, L₁', L₂, L₃, L₃', L₄, L₄' are independently a linker, wherein said linker is a bond, alkylene, O-alkylene, —NHC(O)X—, —C(O)NHX—, —C(O)X—, —X'NHC(O)—, —X'C(O)NH—, —X'NHC(O)X—, —X'C(O)NHX—, —X'C(O)X— or —NHX—;

X and X' are independently an alkylene, haloalkylene, aryl or phenyl;

F₁, F₂, F₃, F₄ are independently substituted or unsubstituted anthracene, substituted or unsubstituted naphthalene, substituted or unsubstituted fluorenyl, substituted or unsubstituted dansyl, substituted or unsubstituted nile red, substituted or unsubstituted fluorescein, substituted or unsubstituted rhodamine, substituted or unsubstituted perylene, substituted or unsubstituted pyrene, substituted or unsubstituted cyanine, substituted or unsubstituted coumarine or combination thereof; R₁, R₂, R₃, R₄ are independently a receptor, wherein said receptor is boronic acid, aryl-boronic acid, phenyl-boronic acid, or naphthyl-boronic acid;

wherein said F₁, F₂, F₃ and F₄ are independently substituted by one to three substituents, wherein said substituents are alkyl, alkenyl, haloalkyl, aryl, O-aryl, —(CH₂)n-aryl, cycloalkyl, O-cycloalkyl, CF₃, F, I, Br, Cl, NO₂, CN, N(R')₂, COOH, COR', NHCOR', CONHR', (CH₂)$_n$NH₂, (CH₂)$_n$NHR', SR', SH, OR', (CH₂)$_n$OH, (CH₂)$_n$COOH, or OH; wherein R' is H, alkyl, haloalkyl, dihaloalkyl, trihaloalkyl, aryl, phenyl or halogen and n is between 0 to 8. In another embodiment n is between 1 to 6.

In one embodiment, this invention is directed to a compound of formula V or its isomer:

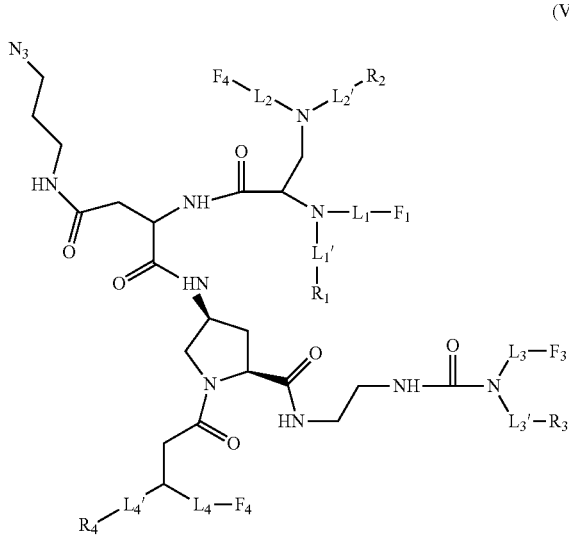

(V)

wherein
L₁, L₁', L₂, L₃, L₃', L₄, L₄' are independently a linker, wherein said linker is a bond, alkylene, O-alkylene, —NHC(O)X—, —C(O)NHX—, —C(O)X—, —X'NHC(O)—, —X'C(O)NH—, —X'NHC(O)X—, —X'C(O)NHX—, —X'C(O)X— or —NHX—;

X and X' are independently an alkylene, haloalkylene, aryl or phenyl;

F₁, F₂, F₃, F₄ are independently substituted or unsubstituted anthracene, substituted or unsubstituted naphthalene, substituted or unsubstituted fluorenyl, substituted or unsubstituted dansyl, substituted or unsubstituted nile red, substituted or unsubstituted fluorescein, substituted or unsubstituted rhodamine, substituted or unsubstituted perylene, substituted or unsubstituted pyrene, substituted or unsubstituted cyanine, substituted or unsubstituted coumarine or combination thereof;

R₁, R₂, R₃, R₄ are independently a receptor, wherein said receptor is boronic acid, aryl-boronic acid, phenyl-boronic acid, or naphthyl-boronic acid;

wherein said F₁, F₂, F₃ and F₄ are independently substituted by one to three substituents, wherein said substituents are alkyl, alkenyl, haloalkyl, aryl, O-aryl, —(CH₂)n-aryl, cycloalkyl, O-cycloalkyl, CF₃, F, I, Br, Cl, NO₂, CN, N(R)₂, COOH, COR', NHCOR', CONHR', (CH₂)$_n$NH₂, (CH₂)$_n$NHR', SR', SH, OR, (CH₂)$_n$OH, (CH₂)$_n$COOH, or OH; wherein R' is H, alkyl, haloalkyl, dihaloalkyl, trihaloalkyl, aryl, phenyl or halogen; and n is from 0 to 8.

In one embodiment, this invention is directed to a compound of formula 32 or its isomer:

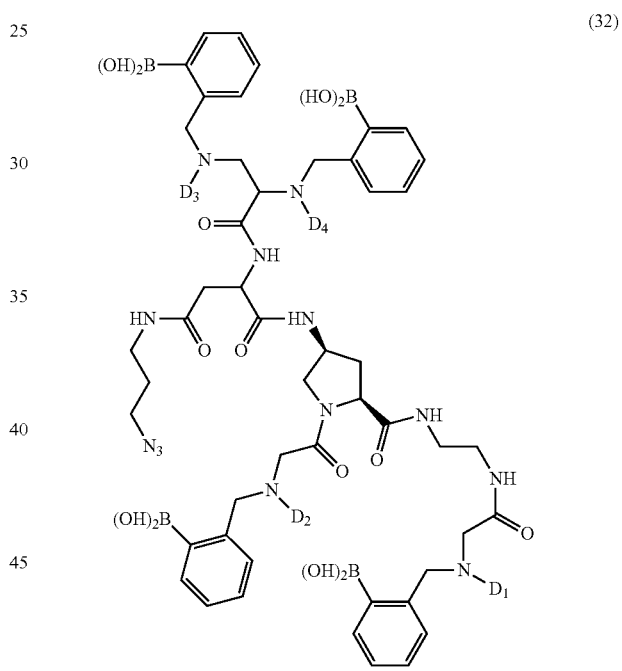

(32)

wherein D₁, D₂, D₃, D₄ independently can be any one of the dyes as described in this invention.

In one embodiment, the linkers L₁, L₂, L₃, L₄ of compound of formula I to III are independently -alkylene-. In another embodiment, the linkers L₁, L₂, L₃, L₄ of compound of formula I to III are independently —O-alkylene-. In one embodiment, the linkers of L₁, L₂, L₃, L₄ of compound of formulas I to III are independently —NHC(O)—. In another embodiment, the linkers of L₁, L₂, L₃, L₄ of compound of formulas I to III are independently —C(O)NH—. In another embodiment, the linkers L₁, L₂, L₃, L₄ of compound of formulas I to III are independently —NHC(O)X—. In another embodiment, the linkers L₁, L₂, L₃, L₄ of compound of formula I to III are independently —C(O)NHX—. In another embodiment, the linkers L₁, L₂, L₃, L₄ of compound of formula I to M are independently —C(O)X—. In another embodiment, the linkers L₁, L₂, L₃, L₄ of compound of formula I to III are independently —X'NHC(O)—. In another embodiment, the linkers $L_1$, $L_2$, $L_3$, $L_4$ of compound of formula I to III are independently —X'C(O)NH—. In another embodiment, the linkers $L_1$, $L_2$, $L_3$, $L_4$ of compound of formula I to III are independently —X'NHC(O)X—. In another embodiment, the linkers $L_1$, $L_2$, $L_3$, $L_4$ of compound of formula I to III are independently —X'C(O)NHX—. In another embodiment, the linkers $L_1$, $L_2$, $L_3$, $L_4$ of compound of formula I to III are independently —X'C(O)X—. In another embodiment, the linkers $L_1$, $L_2$, $L_3$, $L_4$ of compound of formula I to III IV are independently —NHX—. In another embodiment, the linkers $L_1$, $L_2$, $L_3$, $L_4$ of compound of formula I to III are independently —NH-[amino-acid]-C(O)—. In another embodiment, the linkers $L_1$, $L_2$, $L_3$, $L_4$ of compound of formula I to III are independently —NH-[amino-acid]-C(O)-alkylene-. In another embodiment, the linkers $L_1$, $L_2$, $L_3$, $L_4$ of compound of formula I to III are independently —C(O)-[amino-acid]-NH—. In another embodiment, the linkers $L_1$, $L_2$, $L_3$, $L_4$ of compound of formula I to III are independently —C(O)-[amino-acid]-NH-alkylene-.

In one embodiment, $Z_1$, $Z_2$, $Z_3$, $Z_4$ of compound of formula I to III are independently hydrogen. In another embodiment, $Z_1$, $Z_2$, $Z_3$, $Z_4$ of compound of formula I to III are independently alkyl. In another embodiment, $Z_1$, $Z_2$, $Z_3$, $Z_4$ of compound of formula I to III are independently alkenyl. In another embodiment, $Z_1$, $Z_2$, $Z_3$, $Z_4$ of compound of formula I to III are independently haloalkyl. In another embodiment, $Z_1$, $Z_2$, $Z_3$, $Z_4$ of compound of formula I to III are independently aryl. In another embodiment, $Z_1$, $Z_2$, $Z_3$, $Z_4$ of compound of formula I to III are independently O-aryl. In another embodiment, $Z_1$, $Z_2$, $Z_3$, $Z_4$ of compound of formula I to III are independently —(CH$_2$)n-aryl. In another embodiment, $Z_1$, $Z_2$, $Z_3$, $Z_4$ of compound of formula I to III are independently cycloalkyl. In another embodiment, $Z_1$, $Z_2$, $Z_3$, $Z_4$ of compound of formula I to III are independently O-cycloalkyl. In another embodiment, $Z_1$, $Z_2$, $Z_3$, $Z_4$ of compound of formula I to III are independently $CF_3$. In another embodiment, $Z_1$, $Z_2$, $Z_3$, $Z_4$ of compound of formula I to III are independently F, I, Br or Cl. In another embodiment, $Z_1$, $Z_2$, $Z_3$, $Z_4$ of compound of formula I to III are independently $NO_2$. In another embodiment, $Z_1$, $Z_2$, $Z_3$, $Z_4$ of compound of formula I to III are independently CN. In another embodiment, $Z_1$, $Z_2$, $Z_3$, $Z_4$ of compound of formula I to III are independently $N(R)_2$. In another embodiment, $Z_1$, $Z_2$, $Z_3$, $Z_4$ of compound of formula I to III are independently COOH. In another embodiment, $Z_1$, $Z_2$, $Z_3$, $Z_4$ of compound of formula I to III are independently COR'. In another embodiment, $Z_1$, $Z_2$, $Z_3$, $Z_4$ of compound of formula I to III are independently NHCOR'. In another embodiment, $Z_1$, $Z_2$, $Z_3$, $Z_4$ of compound of formula I to III are independently CONHR'. In another embodiment, $Z_1$, $Z_2$, $Z_3$, $Z_4$ of compound of formula I to III are independently $(CH_2)_nNH_2$. In another embodiment, $Z_1$, $Z_2$, $Z_3$, $Z_4$ of compound of formula I to III are independently $(CH_2)_nNHR'$. In another embodiment, $Z_1$, $Z_2$, $Z_3$, $Z_4$ of compound of formula I to III are independently SR. In another embodiment, $Z_1$, $Z_2$, $Z_3$, $Z_4$ of compound of formula I to III are independently SH. In another embodiment, $Z_1$, $Z_2$, $Z_3$, $Z_4$ of compound of formula I to III are independently OR'. In another embodiment, $Z_1$, $Z_2$, $Z_3$, $Z_4$ of compound of formula I to III are independently $(CH_2)_nOH$. In another embodiment, $Z_1$, $Z_2$, $Z_3$, $Z_4$ of compound of formula I to III are independently $(CH_2)_nCOOH$. In another embodiment, $Z_1$, $Z_2$, $Z_3$, $Z_4$ of compound of formula I to III are independently OH.

In one embodiment, the linkers $L_1$, $L_1'$, $L_2$, $L_3$, $L_3'$, $L_4$, $L_4'$ of compound of formulas IV and V are independently a bond. In another embodiment, the linkers $L_1$, $L_1'$, $L_2$, $L_3$, $L_3'$, $L_4$, $L_4'$ of compound of formulas IV and V are independently alkylene. In another embodiment, the linkers $L_1$, $L_1'$, $L_2$, $L_3$, $L_3'$, $L_4$, $L_4'$ of compound of formulas IV and V are independently O-alkylene. In one embodiment, the linkers of $L_1$, $L_2$, $L_3$, $L_4$ of compound of formulas IV and V are independently —NHC(O)—. In another embodiment, the linkers of $L_1$, $L_2$, $L_3$, $L_4$ of compound of formulas IV and V are independently —C(O)NH—. In another embodiment, the linkers $L_1$, $L_1'$, $L_2$, $L_3$, $L_3'$, $L_4$, $L_4'$ of compound of formulas IV and V are independently —NHC(O)X—. In another embodiment, the linkers $L_1$, $L_1'$, $L_2$, $L_3$, $L_3'$, $L_4$, $L_4'$ of compound of formulas IV and V are independently —C(O)NHX—. In another embodiment, the linkers $L_1$, $L_1'$, $L_2$, $L_3$, $L_3'$, $L_4$, $L_4'$ of compound of formulas IV and V are independently —C(O)X—. In another embodiment, the linkers $L_1$, $L_1'$, $L_2$, $L_3$, $L_3'$, $L_4$, $L_4'$ of compound of formulas IV and V are independently —X'NHC(O)—. In another embodiment, the linkers $L_1$, $L_1'$, $L_2$, $L_3$, $L_3'$, $L_4$, $L_4'$ of compound of formulas IV and V are independently —X'C(O)NH—. In another embodiment, the linkers $L_1$, $L_1'$, $L_2$, $L_3$, $L_3'$, $L_4$, $L_4'$ of compound of formulas IV and V are independently —X'NHC(O)X—. In another embodiment, the linkers $L_1$, $L_1'$, $L_2$, $L_3$, $L_3'$, $L_4$, $L_4'$ of compound of formulas IV and V are independently —X'C(O)NHX—. In another embodiment, the linkers $L_1$, $L_1'$, $L_2$, $L_3$, $L_3'$, $L_4$, $L_4'$ of compound of formulas IV and V are independently —X'C(O)X—. In another embodiment, the linkers $L_1$, $L_1'$, $L_2$, $L_3$, $L_3'$, $L_4$, $L_4'$ of compound of formulas IV and V are independently —NHX—.

Figure 13:
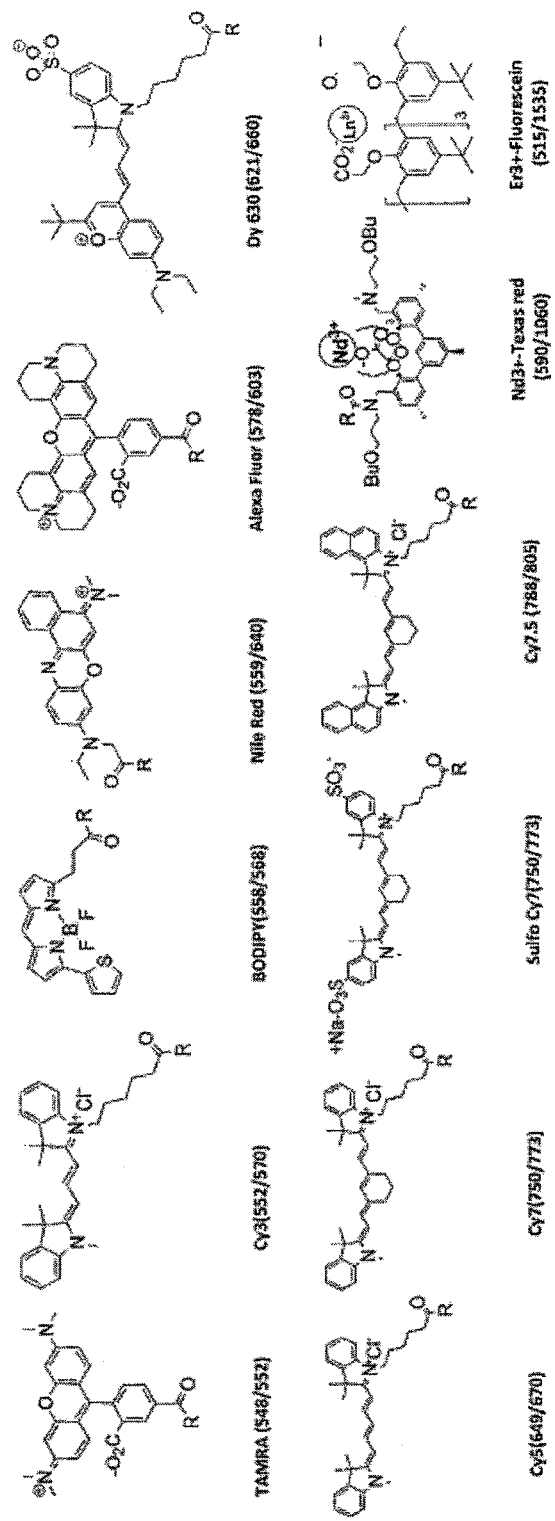
FIG. 13 depicts excitation and emission wavelengths of various commercially available red and NIR-emitting dyes (D)/chromophores of this invention. (R=OH or NH(CH$_2$)$_2$Br)
Figure 16B:
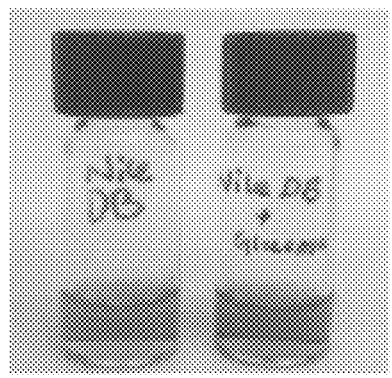
Figure 16C:
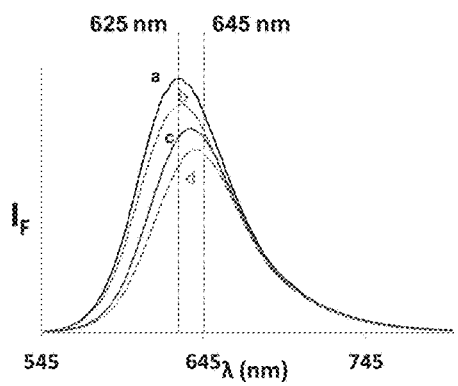

In one embodiment, $F_1$, $F_2$, $F_3$, and/or $F_4$ of compound of formulas IV and V are independently substituted or unsubstituted anthracene. In another embodiment, $F_1$, $F_2$, $F_3$, and/or $F_4$ of compound of formulas N and V are independently substituted or unsubstituted naphthalene. In another embodiment, $F_1$, $F_2$, $F_3$ and/or $F_4$ of compound of formulas N and V are independently substituted or unsubstituted fluorenyl. In another embodiment, $F_1$, $F_2$, $F_3$, and/or $F_4$ of compound of formulas IV and V are independently substituted or unsubstituted dansyl. In another embodiment, $F_1$, $F_2$, $F_3$ and/or $F_4$ of compound of formulas N and V are independently substituted or unsubstituted nile red. In another embodiment, $F_1$, $F_2$, $F_3$ and/or $F_4$ of compound of formulas IV and V are independently substituted or unsubstituted fluorescein. In another embodiment, $F_1$, $F_2$, $F_3$ and/or $F_4$ of compound of formulas N and V are independently substituted or unsubstituted rhodamine. In another embodiment, $F_1$, $F_2$, $F_3$, $F_4$ of compound of formulas IV and V are independently substituted or unsubstituted perylene. In another embodiment, $F_1$, $F_2$, $F_3$ and/or $F_4$ of compound of formulas N and V are independently substituted or unsubstituted cyanine. In another embodiment, $F_1$, $F_2$, $F_3$ and/or $F_4$ of compound of formulas IV and V are independently substituted or unsubstituted coumarine. In another embodiment, $F_1$, $F_2$, $F_3$ and/or $F_4$ of compound of formulas N and V are independently substituted or unsubstituted pyrene. In one embodiment, $F_1$, $F_2$, $F_3$, and/or $F_4$ of compound of formulas IV and V are independently substituted or unsubstituted red or NIR-emitting dyes as illustrated in FIG. 13. In another embodiment, $F_1$, $F_2$, $F_3$, and/or $F_4$ of compound of formulas IV and V are independently substituted or unsubstituted TAMRA. In another embodiment, $F_1$, $F_2$, $F_3$, and/or $F_4$ of compound of formulas IV and V are independently substituted or unsubstituted Cy3. In another embodiment, $F_1$, $F_2$, $F_3$, and/or $F_4$ of compound of formulas N and V are independently substituted or unsubstituted BODIPY. In another embodiment, $F_1$, $F_2$, $F_3$, and/or $F_4$ of compound of formulas IV and V are independently substituted or unsubstituted Nile Red. In another embodiment, $F_1$, $F_2$, $F_3$, and/or $F_4$ of compound of formulas N and V are independently substituted or unsubstituted Alexa Fluor. In another embodiment, $F_1$, $F_2$, $F_3$, and/or $F_4$ of compound of formulas N and V are independently substituted or unsubstituted Dy 630. In another embodiment, $F_1$, $F_2$, $F_3$, and/or $F_4$ of compound of formulas N and V are independently substituted or unsubstituted Cy5. In another embodiment, $F_1$, $F_2$, $F_3$, and/or $F_4$ of compound of formulas IV and V are independently substituted or unsubstituted Cy7. In another embodiment, $F_1$, $F_2$, $F_3$, and/or $F_4$ of compound of formulas N and V are independently substituted or unsubstituted Sulfo Cy7. In another embodiment, $F_1$, $F_2$, $F_3$, and/or $F_4$ of compound of formulas IV and V are independently substituted or unsubstituted Cy7.5. In another embodiment, $F_1$, $F_2$, $F_3$, and/or $F_4$ of compound of formulas IV and V are independently substituted or unsubstituted Nd3+-Texas Red. In another embodiment, $F_1$, $F_2$, $F_3$, and/or $F_4$ of compound of formulas IV and V are independently substituted or unsubstituted Fr3+-Fluorescein. In another embodiment, $F_1$, $F_2$, $F_3$, and/or $F_4$ of compound of formulas IV and V are independently substituted or unsubstituted Nile DB as illustrated in FIG. 16.

In one embodiment, $D_1$, $D_2$, $D_3$, and/or $D_4$ of the compounds of this invention (such as compounds 21, 22, 23, 25, 26, 27, 29-32—see FIGS. 14-15) refer to dyes. In one embodiment, $D_1$, $D_2$, $D_3$, and/or $D_4$ of the compounds of this invention are independently substituted or unsubstituted anthracene. In another embodiment, $D_1$, $D_2$, $D_3$, and/or $D_4$ of the compounds of this invention are independently substituted or unsubstituted naphthalene. In another embodiment, $D_1$, $D_2$, $D_3$, and/or $D_4$ of the compounds of this invention are independently substituted or unsubstituted fluorenyl. In another embodiment, $D_1$, $D_2$, $D_3$, and/or $D_4$ of the compounds of this invention are independently substituted or unsubstituted dansyl. In another embodiment, $D_1$, $D_2$, $D_3$, and/or $D_4$ of the compounds of this invention are independently substituted or unsubstituted nile red. In another embodiment, $D_1$, $D_2$, $D_3$, and/or $D_4$ of the compounds of this invention are independently substituted or unsubstituted fluorescein. In another embodiment, $D_1$, $D_2$, $D_3$, and/or $D_4$ of the compounds of this invention are independently substituted or unsubstituted rhodamine. In another embodiment, $D_1$, $D_2$, $D_3$, and/or $D_4$ of the compounds of this invention are independently substituted or unsubstituted perylene. In another embodiment, $D_1$, $D_2$, $D_3$, and/or $D_4$ of the compounds of this invention are independently substituted or unsubstituted cyanine. In another embodiment, $D_1$, $D_2$, $D_3$, and/or $D_4$ of the compounds of this invention are independently substituted or unsubstituted coumarine. In another embodiment, $D_1$, $D_2$, $D_3$, and/or $D_4$ of the compounds of this invention are independently substituted or unsubstituted pyrene. In one embodiment, $D_1$, $D_2$, $D_3$, and/or $D_4$ of the compounds of this invention are independently substituted or unsubstituted red or NIR-emitting dyes as illustrated in FIG. 13. In another embodiment, $D_1$, $D_2$, $D_3$, and/or $D_4$ of the compounds of this invention are independently substituted or unsubstituted TAMRA. In another embodiment, $D_1$, $D_2$, $D_3$, and/or $D_4$ of the compounds of this invention independently substituted or unsubstituted Cy3. In another embodiment, $D_1$, $D_2$, $D_3$, and/or $D_4$ of the compounds of this invention are independently substituted or unsubstituted BODIPY. In another embodiment, $D_1$, $D_2$, $D_3$, and/or $D_4$ of the compounds of this invention are independently substituted or unsubstituted Nile Red. In another embodiment, $D_1$, $D_2$, $D_3$, and/or $D_4$ of the compounds of this invention are independently substituted or unsubstituted Alexa Fluor. In another embodiment, $D_1$, $D_2$, $D_3$, and/or $D_4$ of the compounds of this invention are independently substituted or unsubstituted Dy 630. In another embodiment, $D_1$, $D_2$, $D_3$, and/or $D_4$ of the compounds of this invention are independently substituted or unsubstituted Cy5. In another embodiment, $D_1$, $D_2$, $D_3$, and/or $D_4$ of the compounds of this invention are independently substituted or unsubstituted Cy7. In another embodiment, $D_1$, $D_2$, $D_3$, and/or $D_4$ of the compounds of this invention are independently substituted or unsubstituted Sulfo Cy7. In another embodiment, $D_1$, $D_2$, $D_3$, and/or $D_4$ of the compounds of this invention are independently substituted or unsubstituted Cy7.5. In another embodiment, $D_1$, $D_2$, $D_3$, and/or $D_4$ of the compounds of this invention are independently substituted or unsubstituted Nd3+-Texas Red. In another embodiment, $D_1$, $D_2$, $D_3$, and/or $D_4$ of the compounds of this invention are independently substituted or unsubstituted Fr3+-Fluorescein. In another embodiment, $D_1$, $D_2$, $D_3$, and/or $D_4$ of the compounds of this invention are independently substituted or unsubstituted Nile DB as illustrated in FIG. 16.

Definitions

In some embodiments, the term "isomer" includes, but is not limited to, optical isomers and analogs, structural isomers and analogs, conformational isomers and analogs, enantiomers, stereoisomers, diastereomers, tautomers and the like. In one embodiment, the term "isomer" is meant to encompass optical isomers of the described compounds such as enantiomers and diastereomers. It will be appreciated by those skilled in the art that the compounds of the present invention contain at least one chiral center. Accordingly, the compounds used in the methods of the present invention may exist in, and be isolated in, optically-active or racemic forms. It is to be understood that the present invention encompasses any racemic, optically-active, or stereoisomeric form, or mixtures thereof In one embodiment, the compounds are the pure (R)-isomers. In another embodiment, the compounds are the pure (S)-isomers. In another embodiment, the compounds are a mixture of the (R) and the (S) isomers. In another embodiment, the compounds are a racemic mixture comprising an equal amount of the (R) and the (S) isomers.

In one embodiment, the compounds of this invention are the pure (RR)-stereoisomers. In another embodiment, the compounds are the pure (SS)-stereoisomers. In another embodiment, the compounds are the pure (RS)-stereoisomers. In another embodiment, the compounds are the pure (SR)-stereoisomers. In another embodiment, the compounds are a mixture of the (RR), (SS), (RS) and the (SR) stereoisomers. In another embodiment, the compounds are a mixture of the (RR) and the (RS) diastereomers. In another embodiment, the compounds are a mixture of the (RR) and the (SR) diastereomers. In another embodiment, the compounds are a mixture of the (RR) and the (SS) enantiomers. In another embodiment, the compounds are a mixture of the (SS) and the (RS) diastereomers. In another embodiment, the compounds are a mixture of the (SS) and the (SR) diastereomers. In another embodiment, the compounds are a mixture of the (SR) and the (RS) enantiomers. In another embodiment, the compounds are a racemic mixture comprising an equal amount of the (RR), (SS), (RS) and the (SR) stereoisomers. In another embodiment, the compounds are a racemic mixture comprising an equal amount of the (RR) and (SS) enantiomers. In another embodiment, the compounds are a racemic mixture comprising an equal amount of the (RS) and the (SR) enantiomers.

It is well known in the art how to prepare optically-active forms (for example, by resolution of the racemic form by recrystallization techniques, by synthesis from optically-active starting materials, by chiral synthesis, or by chromatographic separation using a chiral stationary phase).

An "alkyl" or "alkylene" group refers, in one embodiment, to a saturated aliphatic hydrocarbon, including straight-chain and branched-chain. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen, hydroxy, alkoxy, carbonyl, amido, alkylamido, dialkylamido, nitro, amino, alkylamino, dialkylamino, carboxyl, thio and thioalkyl.

An "alkenyl" group refers, in another embodiment, to an unsaturated hydrocarbon, including straight chain and branched chain having one or more double bond. The alkenyl group may have one double bond, two double bonds, three double bonds, etc. Examples of alkenyl groups are ethenyl, propenyl, butenyl, cyclohexenyl, etc. In one embodiment, the alkenyl group has 1-12 carbons. In another embodiment, the alkenyl group has 1-7 carbons. In another embodiment, the alkenyl group has 1-6 carbons. In another embodiment, the alkenyl group has 1-4 carbons. The alkenyl group may be unsubstituted or substituted by one or more groups selected from halogen, hydroxy, alkoxy, carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, in one embodiment by F, in another embodiment by Cl, in another embodiment by Br, in another embodiment by I.

A "cycloalkyl" group refers to a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are selected from halogen, haloalkyl, hydroxy, alkoxy, carbonyl, amido, alkylamido, dialkylamido, nitro, amino, alkylamino, dialkylamino, carboxy, thio or thioalkyl. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy, carbonyl, amido, alkylamido, dialkylamido, nitro, amino, alkylamino, dialkylamino, carboxy, thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the aryl group is a 4-8 membered ring. In another embodiment, the aryl group is a 4-12 membered ring(s). In another embodiment, the aryl group is a 3-10 membered ring(s). In another embodiment, the aryl group is a 3-8 membered ring(s). In another embodiment, the aryl group is a 6 membered ring. In another embodiment, the aryl group is a 5 membered ring. In another embodiment, the aryl group is 2-4 fused ring system.

In one embodiment, this invention is directed to a compound, complex, encoding system and methods of use thereof. In another embodiment, the compound of this invention binds to an analyte resulting in a conformational change of the compound upon the binding of the analyte to the compound of this invention, which is transmitted to the chromophore and results in an optical signature. In another embodiment, the optical signature is a fluorescent pattern. The optical signature is characteristic to the complex formed between the compound of this invention and the analyte. In another embodiment, attaching the chromophore to an anchor (such as proline) provides a flexible and chiral molecular cavity that can potentially accommodate and discriminate between a wide range of carbohydrates.

In another embodiment, the optical signature of the complex of this invention is used to identify, detect, differentiate an analyte of this invention, or diagnose a disease which is characterize by the presence of the analyte.

In another embodiment, the optical signature of the complex of this invention is used to identify, detect, differentiate a carbohydrate of this invention, or diagnose a disease which is characterize by the presence of the carbohydrate, glycans and glycoproteins.

Binding of different analytes affects differently the optical properties of the chromophore, as well as to induce conformational changes that would result in different optical signature. In another embodiment binding of different analytes affects differently the emission of each fluorescent dye, as well as to induce conformational changes that would result in different fluorescence resonance energy transfer (FRET) processes between them. The combination of these effects provides a vast number of unique optical signatures. In one embodiment, the compound of this invention includes at least three fluorescent dyes. In another embodiment, the first fluorescent dye emits at a wavelength which is the absorption wavelength of a second fluorescent dye. In another embodiment, the first fluorescent dye is naphthalene, fluorenyl or combination thereof, wherein said first fluorescent dye emits light at a wavelength of between 300-370 nm following excitation at 270 nm. In another embodiment, the second fluorescent dye is dansyl, anthracene or combination thereof, wherein said second fluorescent dye absorbs light at a range of between 300 to 400 nm.

In another embodiment, FIG. 3 shows the excitation and emission spectra of the individual fluorescent dyes, namely, each boronic acid-dye conjugate (e.g., Naph*, An*, and Dan*) and a fluorenyl-aspartic acid derivative (Flu*). The emission spectra of naphthalene and fluorenyl overlap with the excitation spectra of antharacene and dansyl. Therefore, illuminating at 270 nm results in an emission pattern ranging across the UV-Vis spectrum due to FRET between the donors (e.g., naphthalene and fluorenyl) and acceptors (e.g., dansyl and anthracene) as well as direct excitations, mainly of naphthalene, fluorenyl, and dansyl. An additional energy transfer process that occurs to a lesser extent involves FRET between anthracene and dansyl. Because FRET largely depends on the distances between the donors and acceptors, conformational changes that are likely to occur upon carbohydrate binding is one factor that should contribute to the generation of distinct fluorescence signatures.

Another photochemical process known to significantly affect the emission of boronic acid-based sensors is photoinduced electron transfer (PET), resulting from incorporating a nitrogen atom in the vicinity of a boronic acid and a fluorophore.

A third signaling mechanism that further contributes to the discrimination ability of the compound of this invention is an internal charge transfer (ICT). In designing a differential compound an advantage of ICT over PET and FRET is that ICT can also induce a change in the emission wavelength.

In another embodiment, the optical signature of the complex of this invention provides quantitative information of the analyte in the sample or the in the liquid medium.

In one embodiment, the compound, complex and methods of this invention operate at the molecular scale, which larger analytical devices cannot address. The compound of this invention includes non-specific chromophores in a single molecular platform. The compound of this invention can discriminate between a wide range of closely related carbohydrate structures.

In one embodiment, the methods of this invention operate at the molecular scale, such that combinatorial sensing by individual molecules is feasible. The molecular diagnostic system presented here combines several recognition elements, and utilizes distinct photochemical processes that enable to analyze a wide range of pharmaceuticals in a high-throughput manner.

In one embodiment, contacting a compound of this invention with an analyte forms a complex. In another embodiment, contacting a compound of this invention with an analyte results in a conformational change of said compound and thereby to a unique optical signature of the complex.

In one embodiment, this invention is directed to a method of differentiating between analytes comprising:
  contacting an analyte with a compound in a liquid medium, wherein said analyte and said compound form a complex; wherein said compound comprises an array of at least three chromophores, at least one receptor and an anchor; wherein contacting said analyte with said compound results in a conformational change of said compound and thereby to a unique optical signature of said complex; and
  measuring the optical signature of said complex;
and thereby, differentiating said analyte.

In one embodiment, this invention is directed to a method of differentiating between carbohydrates comprising:
  contacting a carbohydrate with a compound in a liquid medium, wherein said carbohydrate and said compounds form a complex; wherein said compound comprises an array of at least three chromophores, at least one boronic acid receptor and an anchor; wherein contacting said carbohydrate with said compound results in a conformational change of said compound and thereby to a unique optical signature of said complex and
  measuring the optical signature of said complex;
and thereby, differentiating said carbohydrate.

In one embodiment, this invention is directed to a method of differentiating between saccharides comprising:
  contacting a saccharide with a compound in a liquid medium, wherein said saccharide and said compounds form a complex; wherein said compound comprises an array of at least three fluorescent dyes, at least one boronic acid receptor and an anchor; wherein contacting said saccharide with said compound results in a conformational change of said compound and thereby to a unique optical signature of said complex and
  measuring the optical signature of said complex;
and thereby, differentiating said saccharide.

In one embodiment, this invention is directed to a method of identifying an analyte, said method comprising:
  contacting an analyte with a compound in a liquid medium, wherein said analyte and said compound form a complex; wherein said compound comprises an array of at least three chromophores, at least receptor and an anchor; wherein contacting said analyte with said compound results in a conformational change of said compound and thereby to a unique optical signature of said complex and
  measuring the optical signature of said complex;
and thereby, identifying said analye.

In one embodiment, this invention is directed to a method of identifying a carbohydrate, said method comprising:
  contacting a carbohydrate with a compound in a liquid medium, wherein said carbohydrate and said compound form a complex; wherein said compound comprises an array of at least three chromophores, at least one boronic acid receptor and an anchor; wherein contacting said carbohydrate with said compound results in a conformational change of said compound and thereby to a unique optical signature of said complex and
  measuring the optical signature of said complex;
and thereby, identifying said carbohydrate.

In one embodiment, this invention is directed to a method of identifying a saccharide, said method comprising:
  contacting a saccharide with a compound in a liquid medium, wherein said saccharide and said compound form a complex; wherein said compound comprises an array of at least three chromophores, at least one boronic acid receptor and an anchor; wherein contacting said saccharide with said compound results in a conformational change of said compound and thereby to a unique optical signature of said complex and
  measuring the optical signature of said complex;
and thereby, identifying said saccharide.

In one embodiment, the methods of this invention for identifying an analyte, carbohydrate or a saccharide further comprising comparing the received optical signature with stored database of optical signatures (emission spectra) of said complex of this invention, and thereby identifying said analyte, carbohydrate or a saccharide.

In one embodiment, this invention is directed to a method of diagnosing a disease in a subject, wherein said diagnosis comprises detection of an analyte biomarkers; said method comprising:
  collecting a biological sample from a subject;
  optionally isolating components from said biological sample;
  contacting a compound with an analyte comprised within said sample or within isolated component in a liquid medium; wherein said analyte forms a complex with said compound; wherein said compound comprises an array of at least three chromophores, at least one receptor and an anchor; wherein contacting said compound with said analye results in a conformational change of said compound and thereby to a unique optical signature of said complex;
  measuring the optical signature of said complex;
  identifying an analyte biomarker in said sample, said analyte biomarker being characteristic of a disease; or measuring a change in a concentration of an analyte biomarker in said sample compared to normative values, wherein said change is characteristic of a disease.

In one embodiment, this invention is directed to a method of diagnosing a disease in a subject, wherein said diagnosis comprises detection of glycans, glycoprotein or carbohydrates biomarkers, said method comprising:
- collecting a biological sample from a subject;
- optionally isolating components from said biological sample;
- contacting a compound with glycans, glycoprotein or carbohaydreates comprised within said sample or within isolated component in a liquid medium; wherein said glycans, glycoprotein or carbohydrates forms a complex with said compound; wherein said compound comprises an array of at least three chromophores, at least one boronic acid receptor and an anchor; wherein contacting said compound with said glycans, glycoprotein or carbohydrates results in a conformational change of said compound and thereby to a unique optical signature of said complex;
- measuring the optical signature of said complex;
- identifying a glycans, glycoprotein or carbohydrates biomarkers in said sample, said glycans, glycoprotein or carbohydrates biomarkers being characteristic of a disease; or measuring a change in a concentration of glycans, glycoprotein or carbohydrates biomarkers in said sample compared to normative values, wherein said change is characteristic of a disease.

In one embodiment, this invention is directed to a method of diagnosing a disease in a subject, wherein said diagnosis comprises detection of a saccharide biomarker; said method comprising:
- collecting a biological sample from a subject;
- optionally isolating components from said biological sample;
- contacting a compound with a saccharide comprised within said sample or within isolated component in a liquid medium; wherein said saccharide forms a complex with said compound; wherein said compound comprises an array of at least three chromophores, at least one boronic acid receptor and an anchor; wherein contacting said compound with said saccharide results in a conformational change of said compound and thereby to a unique optical signature of said complex;
- measuring the optical signature of said complex;
- identifying a saccharide biomarker in said sample, said saccharide biomarker being characteristic of a disease; or measuring a change in a concentration of a saccharide biomarker in said sample compared to normative values, wherein said change is characteristic of a disease;

thereby, diagnosing a disease in a subject.

In one embodiment, the methods of this invention for diagnosing a disease in a subject comprising a step of identifying a analyte, glycans, glycoprotein, carbohydrates or saccharide biomarkers. In another embodiment, the identifying step further comprising comparing the received optical signature of the complex with stored database of optical signatures (emission spectra) of said complex of this invention, and thereby identifying said analyte, glycans, glycoprotein, carbohydrates or saccharide biomarkers.

In one embodiment, this invention is directed to a kit comprising a compound of this invention in a liquid medium. In one embodiment, said kit further comprises tools for measuring an optical signature (i.e. spectrophotometer) of a complex formed by contacting said compound with analytes, or carbohydrates, or saccharides. In another embodiment, said kit further comprises means for comparing the measured optical signature with stored database of optical signatures (emission spectra) of said complex of this invention. In one embodiment, said kit can be used for differentiating between said analytes, or said carbohydrates, or saccharides. In another embodiment, said kit can be used for identifying said analytes, or said carbohydrates, or said saccharides, and thereby diagnosing a disease in a subject.

In one embodiment, this invention is directed to a kit for differentiating between analytes comprising:
- a compound of this invention in a liquid medium, wherein said compound comprises an array of at least three chromophores, at least one receptor and an anchor; and
- a tool for measuring a unique optical signature (i.e. spectrophotometer) of a complex formed by contacting said analytes with said compound, thereby, differentiating said analytes.

In one embodiment, said compound is a compound of formula (I). In another embodiment, said compound is a compound of formula (II). In another embodiment, said compound is a compound of formula (III). In another embodiment, said compound is a compound of formula (IV). In another embodiment, said compound is a compound of formula (V). In another embodiment, said compound is compound 1. In another embodiment, said compound is compound 32.

In one embodiment, this invention is directed to a kit for differentiating between carbohydrates comprising:
- a compound of this invention in a liquid medium, wherein said compound comprises an array of at least three chromophores, at least one boronic acid receptor and an anchor; and
- a tool for measuring a unique optical signature (i.e. spectrophotometer) of a complex formed by contacting said carbohydrates with said compound, thereby, differentiating said carbohydrates.

In one embodiment, said compound is a compound of formula (I). In another embodiment, said compound is a compound of formula (II). In another embodiment, said compound is a compound of formula (III). In another embodiment, said compound is a compound of formula (IV). In another embodiment, said compound is a compound of formula (V). In another embodiment, said compound is compound 1. In another embodiment, said compound is compound 32.

In one embodiment, this invention is directed to a kit for differentiating between saccharides comprising:
- a compound of this invention in a liquid medium, wherein said compound comprises an array of at least three fluorescent dyes, at least one boronic acid receptor and an anchor; and
- a tool for measuring a unique optical signature (i.e. spectrophotometer) of a complex formed by contacting said saccharides with said compound;

thereby, differentiating said saccharides.

In one embodiment, said compound is a compound of formula (I). In another embodiment, said compound is a compound of formula (II). In another embodiment, said compound is a compound of formula (III). In another embodiment, said compound is a compound of formula (IV). In another embodiment, said compound is a compound of formula (V). In another embodiment, said compound is compound 32. In another embodiment, said compound is compound 1.

In one embodiment, this invention is directed to a kit for identifying an analyte, comprising:
- a compound of this invention in a liquid medium, wherein said compound comprises an array of at least three chromophores, at least receptor and an anchor; and a tool for measuring a unique optical signature (i.e. spectrophotometer) of a complex formed by contacting said analyte with said compound;

thereby, identifying said analye.

In one embodiment, said compound is a compound of formula (I). In another embodiment, said compound is a compound of formula (II). In another embodiment, said compound is a compound of formula (III). In another embodiment, said compound is a compound of formula (IV). In another embodiment, said compound is a compound of formula (V). In another embodiment, said compound is compound 1. In another embodiment, said compound is compound 32.

In one embodiment, this invention is directed to a kit for identifying a carbohydrate, comprising:
 a compound of this invention in a liquid medium, wherein said compound comprises an array of at least three chromophores, at least one boronic acid receptor and an anchor; and
 a tool for measuring a unique optical signature (i.e. spectrophotometer) of a complex formed by contacting said carbohydrate with said compound;

thereby, identifying said carbohydrate.

In one embodiment, said compound is a compound of formula (I). In another embodiment, said compound is a compound of formula (II). In another embodiment, said compound is a compound of formula (III). In another embodiment, said compound is a compound of formula (IV). In another embodiment, said compound is a compound of formula (V). In another embodiment, said compound is compound 1. In another embodiment, said compound is compound 32.

In one embodiment, this invention is directed to a kit for identifying a saccharide, comprising:
 a compound of this invention in a liquid medium, wherein said compound comprises an array of at least three chromophores, at least one boronic acid receptor and an anchor; and
 a tool for measuring a unique optical signature (i.e. spectrophotometer) of a complex formed by contacting said saccharide with said compound;

thereby, identifying said saccharide.

In one embodiment, said compound is a compound of formula (I). In another embodiment, said compound is a compound of formula (II). In another embodiment, said compound is a compound of formula (III). In another embodiment, said compound is a compound of formula (IV). In another embodiment, said compound is a compound of formula (V). In another embodiment, said compound is compound 1. In another embodiment, said compound is compound 32.

In one embodiment, the kits of this invention for identifying an analyte, carbohydrate or a saccharide may further include means for comparing the received optical signature with stored database of optical signatures (emission spectra) of said complex of this invention, and thereby identifying said analyte, carbohydrate or a saccharide.

In one embodiment the complex and method of this invention make use of an analyte. In another embodiment, the analyte is a saccharide. The term "saccharide" in this invention refers to monosaccharide, disaccharide, trisaccharide, polysaccharide, carbohydrate, sugar or glycan. The polysaccharide is linear or branched. In another embodiment, the saccharide is found free or attached to, e.g., proteins, lipids, other carbohydrates, nucleic acid, a virus, or a cell in biological samples. In another embodiment, a saccharide of this invention is a component of a glycoprotein, a glycolipid or a proteoglycan. In another embodiment, the saccharide of this invention is independent of a protein or lipid molecule. Non limiting examples of monosacharides include galactose, glucose, mannose, N-acetylneuraminic acid, fucose, N-acetylgalactosamine, N-acetylglucosamine, xylose, iduronic acid, arabinose and glucuronic acid.

The term "glycoprotein" includes any molecule that contains both a protein component and a carbohydrate component. The carbohydrate component is commonly referred to as a "glycan." As used herein, the term glycoprotein is inclusive of a glycopeptide, a glycopolypeptide and a proteoglycan. A glycan may contain one monosaccharide, or it may contain two or more monosaccharides linked by glycosidic bonds. A glycan can include nonrepeating or repeating monosaccharides, or both.

An oligosaccharide is an oligomeric saccharide that contains two or more saccharides. The structure of an oligosaccharide is typically characterized by particular identity, order, linkage positions (including branch points), and linkage stereochemistry ($\alpha$, $\beta$) of the monomers, and as a result has a defined molecular weight and composition. An oligosaccharide typically contains about 2 to about 20 or more saccharide monomers. In a polysaccharide, the identity, order, linkage positions (including branch points) and/or linkage stereochemistry can vary from molecule to molecule. Polysaccharides typically contain a larger number of monomeric components than oligosaccharides and thus have higher molecular weights. The term "glycan" as used herein is inclusive of both oligosaccharides and polysaccharides, and includes both branched and unbranched polymers as defined herein.

In one embodiment, this invention is directed to a kit and method of differentiating, identifying or diagnosing an analyte, a saccharide or a carbohydrate in a liquid medium. In another embodiment, the liquid medium is an aqueous solution. In another embodiment, the liquid medium is a buffered aqueous solution. In another embodiment, the liquid medium is a biological sample.

In one embodiment, the methods of this invention include a step of measuring the optical signature of the complex of this invention. In another embodiment, the optical signature is a unique optical signature for each complex. In another embodiment, the unique optical signature provides a fluorescence pattern of said complex; and said fluorescence pattern is obtained followed irradiation of said complex at a wavelength that at least one of said fluorescent dyes is excited. In another embodiment, the fluorescence pattern indicates the presence of at least one saccharide in said medium. In one embodiment, measuring the optical signature of the formed complex refers to the emission spectra of the complex. In one embodiment, measuring the optical signature of the formed complex refers to the absorption spectra of the complex. In one embodiment, measuring the optical signature of the formed complex refers to the emission and/or absorption spectra of the complex.

In one embodiment, the method of this invention is directed to a method of diagnosing a disease in a subject, wherein said diagnosis comprises detection of a carbohydrate biomarker comprising the step of collecting a biological sample from a subject. In another embodiment, the term "biological sample" refers to a serum, a blood, a plasma, a urine, a saliva, a peritoneal, a stool, a mucus, a tear, a sweat, a biopsy, a sperm or a cerebrospinal fluid sample.

In one embodiment, the method of this invention is directed to a method of diagnosing a disease in a subject, wherein said diagnosis comprises detection of a carbohydrate biomarker comprising the step of optionally isolating components from said biological sample. In another embodiment, "isolating components" refers to isolating cells having saccharide or carbohydrate; isolating proteins from the biological samples, isolating sugars, isolating glycans, phosphates (non limiting examples include ATP, ADP, AMP, GMP), isolating phospholipids, isolating glycoprotein, a glycolipid or a proteoglycan from the biological sample.

In one embodiment, the method of this invention is directed to a method of diagnosing a disease in a subject. In another embodiment, the disease is a sugar disease. Non limited examples of a disease are hypoglycemia, prostate cancer, diabetes, HIV, Tuberculosis or syndrome X.

In another embodiment, the disease is a glycoprotein based disease. Non limiting examples of a glycoprotein based disease is multiple sclerosis, crohn's disease, autoimmune disease, colitis, inflammatory bowel disease, cancer, lysosomal storage disease, or celiac. Changes of structures and functions of glycoproteins have implications in cancer, inflammatory diseases such as influenza, nerve degenerative diseases, muscle degenerative diseases such as muscle dystrophy, and lifestyle-related diseases such as diabetes. The disease being diagnosed in this invention may be a cardiovascular disease (e.g., acute myocardial infarction), cerebrovascular disease (e.g., stroke), rheumatoid arthritis, chronic alcoholism or cancer (e.g., a carcinoma, lymphoma, blastoma, sarcoma, or leukemia). More particular examples of such cancers include prostate cancer, squamous cell cancer, small-cell lung cancer, non-small-cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, vulval cancer, thyroid cancer, hepatic carcinoma, gastric cancer, melanoma, and various types of head and neck cancer. The disease may also be an autoimmune disease, e.g., autoimmune hepatitis, multiple sclerosis, systemic lupus erythematosus, myasthenia gravis, type I diabetes, rheumatoid arthritis, psoriasis, Hashimoto's thyroiditis, Grave's disease, Sjogren's syndrome, or scleroderma. The methods described herein may also be used to diagnose infections, e.g., viral infections, such as hepatitis C infection and human immunodeficiency virus (HW) infection.

In another embodiment, the disease is prostate cancer.

In one embodiment, the method of this invention is directed to a method of diagnosing a disease in a subject comprising identifying a saccharide biomarker in a biological sample. In another embodiment, the saccharide biomarker is a component of a glycoprotein, a glycolipid or a proteoglycan. In another embodiment, the saccharide biomarker is a monosaccharide, a disaccharide or a glycan independent of a protein or lipid molecule.

A biomarker is a molecular, biological, or physical characteristic that can be measured or otherwise evaluated as an indicator of a normal biologic process, disease state, or response to a therapeutic intervention. The biomarker of the invention is a "saccharide" or "carbohydrate" biomarker, i.e., it includes a 1,2 or 1,3-diol moiety. Saccharide biomarkers of the invention include, but are not limited to, monosaccharides, disaccharides, oligosaccharides, polysaccharides, glycans, saccharides linked to peptides (e.g, proteoglycans), saccharides linked to proteins (e.g., glycoproteins), saccharides linked to lipids (e.g., glycolipids). Saccharide biomarkers are detectable and/or measurable using a compound of this invention.

The saccharide/carbohydrate or glycoprotein biomarker may be indicative of a sugar disease or a glycoprotein disease or a condition by its presence, absence, increase in amount, decrease in amount, or differential glycosylation. Amounts of biomarker can be determined in absolute or relative terms. For example, a carbohydrate biomarker may indicate the presence of cancer or a precancerous condition simply by its presence, absence or amount compared to a noncancerous sample or a predetermined level.

Examples of glycans that can be detected on an ovarian cancer-specific glycoprotein glycoform include erythroagglutinating phytohemagglutinin (E-PHA), *Aleuria aurantia* lectin (AAL) and *Datura stramonium* lectin (DSL). In another embodiment, non limiting examples for diagnosing cancer or a precancerous disease include a GlcNAc β.(1,6) Man branched N-linked glycan, a GlcNAc β.(1,4) Man bisected N-linked glycan, a glycan containing α.(1,6) fucose linked to a core N-acetylglucosamine, and a branched N-linked glycan extended with N-acetyllactosamine.

Various concentrations of biomarkers and biomarker complexes may be detected and measured by the methods described herein. Biomarkers present at concentrations of between about 1-5 mM, 1-100 uM, 50-100 mg/mL or less than, e.g., 100 milligrams/milliliter (mg/ml), 10 mg/ml, 1 mg/ml, 100 micrograms/milliliter (μg/ml), 10 μg/ml, 1 μg/ml, 100 nanograms/milliliter (ng/ml), 10 ng/ml, 1 ng/ml, may be detected in the biological sample, and the concentration may be measured.

In one embodiment, the method of this invention is directed to a method of diagnosing a disease in a subject measuring a change in a concentration of a saccharide biomarker compared to normative values, wherein said change is characteristic of a disease. The term "normative value" refers to the concentration range of saccharide found in a normal healthy subject. The term "normative value" refers to the control.

In one embodiment, the method of this invention is directed to a method of diagnosing a disease in a subject. In another embodiment, a subject refers to a mammal, a human, a female or a male.

The terms "comprises" and variations thereof do not have a limiting meaning where these terms appear in the description and claims.

Unless otherwise specified, "a," "an," "the," and "at least one" are used interchangeably and mean one or more than one.

In one embodiment, this invention is directed to an encoding system for encoding information using a compound of the present invention.

In another embodiment, this invention is directed to an encoding system for encoding information using a complex of a compound represented by the structure of formula (III):

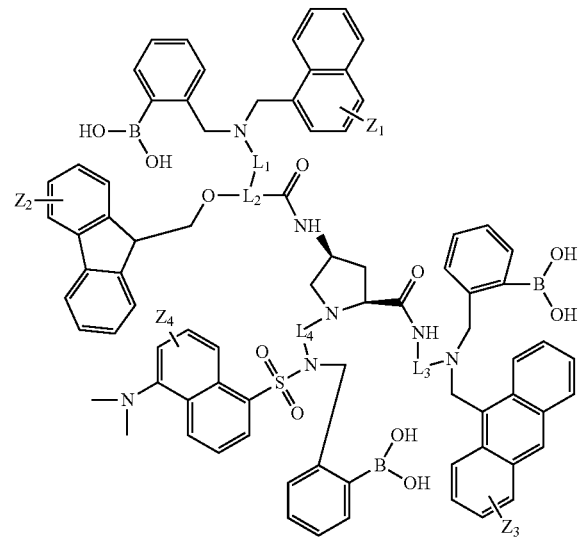

(III)

wherein

L$_1$, L$_2$, L$_3$, L$_4$ are independently a linker, wherein said linker is -alkylene-, —O-alkylene-, —NHC(O)—, —C(O)NH—, —NHC(O)X—, —C(O)NHX—, —C(O)X—, —X'NHC(O)—, —X'C(O)NH—, —X'NHC(O)X—, —X'C(O)NHX—, —X'C(O)X—, —NHX—, —NH-[amino-acid]-C(O)—, —NH-[amino-acid]-C(O)-alkylene-, —C(O)— [amino-acid]-NH—, or —C(O)-[amino-acid]-NH-alkylene-;

X and X' are independently alkylene, haloalkylene, arylene or phenylene; and $Z_1$, $Z_2$, $Z_3$, $Z_4$ are independently hydrogen, alkyl, alkenyl, haloalkyl, aryl, O-aryl, —(CH$_2$)n-aryl, cycloalkyl, O-cycloalkyl, CF$_3$, F, I, Br, Cl, NO$_2$, CN, N(R)$_2$, COOH, COR', NHCOR', CONHR', (CH$_2$)$_n$NH$_2$, (CH$_2$)$_n$NHR', SR', SH, OR', (CH$_2$)$_n$OH, (CH$_2$)$_n$COOH, or OH; wherein R' is H, alkyl, haloalkyl, dihaloalkyl, trihaloalkyl, aryl, phenyl or halogen; and n is from 0 to 8;

and between 2 and 7 analytes in a specific sequence, wherein said complex exhibits a unique optical signature signal;

said encoding system comprising:

a data processor;

a non-transitory database storage device for storing a plurality of database records;

a chemical process interface, for controlling chemical processes binding analytes to the compound; and a spectroscopic interface, for reading unique optical signatures of the complex.

In certain embodiment, n is from 1 to 6.

In one embodiment, $L_1$, $L_2$, $L_3$, $L_4$ are independently -alkylene-, —NHC(O)—, —C(O)NH—, —NHC(O)X—, —C(O)NHX—, —C(O)X—, —X'NHC(O)X—, or —X'C(O)NHX—. In another embodiment, $L_1$ and $L_2$ are independently NHC(O)—, —C(O)NH— —NHC(O)X—, or —C(O)NHX and $L_3$, $L_4$ are independently -alkylene- or —C(O)X—.

In certain embodiment, said compound is represented by the following structure 1:

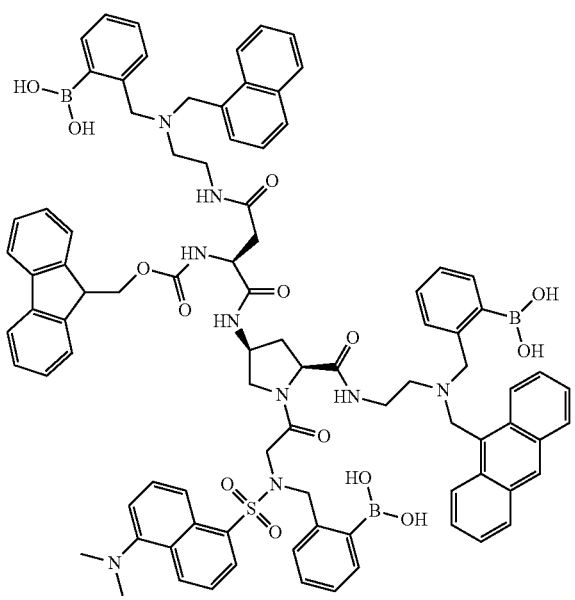

(1)

In one embodiment, said analytes are between 2 and 7 analytes. In another embodiment, 2 or 3 analytes.

In another embodiment, said between 2 and 7 analytes can be any number of analytes. For example, between 2 and 7 analytes. In another embodiment, 2 analytes, 3 analytes, 4 analytes, 5 analytes, 6 analytes, or 7 analytes.

In one embodiment, said analytes are a carbohydrate. In another embodiment, said carbohydrate is L-Glucose, D-Glucose, D-fructose, L-fructose, D-arabinose, D-xylose, L-xylose, L-mannose, D-galactose, D-sorbitol, mannitol, dulcitol, adonitol, xylitol, L-threitol, maltitol, lactulose, D-lactose, D-maltose, D-trehalose, or maltotriose.

In one embodiment, said analytes are the same or different. In another embodiment, said analytes can be distinct from each other. In another embodiment, said analytes can include the same analytes. For example, when three analytes are included, the first two of the analytes can be the same, and the third analyte is distinct from the first two analytes.

In one embodiment, the encoding system further comprises a non-transitory program storage device for storing an application program.

In another embodiment, the encoding system further comprising a hardware controller with a logic element configured to receive an input from the processor.

In one embodiment, this invention is directed to a method of encoding information using a compound represented by the structure of formula (III),

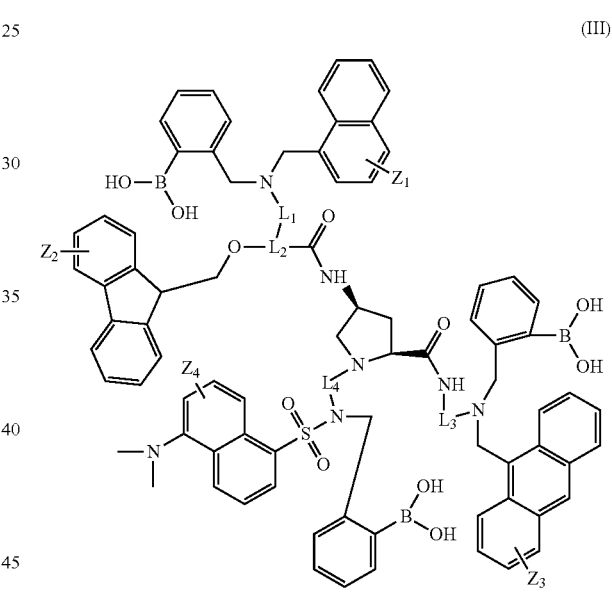

(III)

wherein $L_1$, $L_2$, $L_3$, $L_4$ are independently a linker, wherein said linker is -alkylene-, —O-alkylene-, —NHC(O)—, —C(O)NH—, —NHC(O)X—, —C(O)NHX—, —C(O)X—, —X'NHC(O)—, —X'C(O)NH—, —X'NHC(O)X—, —X'C(O)NHX—, —X'C(O)X—, —NHX—, —NH-[amino-acid]-C(O)—, —NH-[amino-acid]-C(O)-alkylene-, —C(O)-[amino-acid]-NH—, or —C(O)-[amino-acid]-NH-alkylene-;

X and X' are independently alkylene, haloalkylene, arylene or phenylene; and $Z_1$, $Z_2$, $Z_3$, $Z_4$ are independently hydrogen, alkyl, alkenyl, haloalkyl, aryl, O-aryl, —(CH$_2$)n-aryl, cycloalkyl, O-cycloalkyl, CF$_3$, F, I, Br, Cl, NO$_2$, CN, N(R)$_2$, COOH, CUR', NHCOR', CONHR', (CH$_2$)$_n$NH$_2$, (CH$_2$)$_n$NHR', SR', SH, OR', (CH$_2$)$_n$OH, (CH$_2$)$_n$COOH, or OH; wherein R' is H, alkyl, haloalkyl, dihaloalkyl, trihaloalkyl, aryl, phenyl or halogen; and n is from 0 to 8;

the method comprising:
a) contacting said compound with between 2 and 7 analytes in a specific sequence to form a complex, wherein said complex exhibits a unique optical signature signal;
b) reading the unique optical signature;
c) associating the unique optical signature with an encoded reference specifying said analytes contacted in said specific sequence according to a predefined encoding scheme; and
d) storing the encoded reference keyed to the unique optical signature in a database record In certain embodiment, n is from 1 to 6.

In one embodiment, $L_1$, $L_2$, $L_3$, $L_4$ are independently -alkylene-, —NHC(O)—, —C(O)NH—, —NHC(O)X—, —C(O)NHX—, —C(O)X—, —X'NHC(O)X—, or —X'C(O)NHX—. In another embodiment, $L_1$ and $L_2$ are independently NHC(O)—, —C(O)NH— —NHC(O)X—, or —C(O)NHX and $L_3$, $L_4$ are independently -alkylene- or —C(O)X—.

In certain embodiment, said compound is represented by the following structure 1:

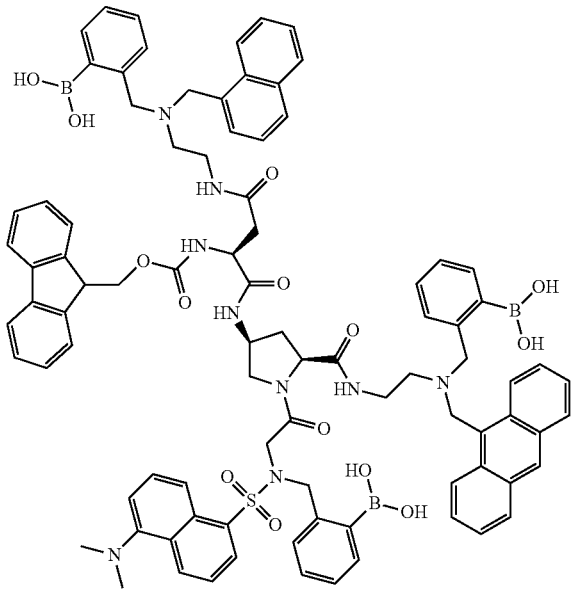

(1)

In one embodiment, said contacting step comprises contacting between 2 and 7 analytes. In another embodiment, 2 or 3 analytes.

In another embodiment, said between 2 and 7 analytes can be any number of analytes. For example, between 2 and 7 analytes. In another embodiment, 2 analytes, 3 analytes, 4 analytes, 5 analytes, 6 analytes, or 7 analytes.

In one embodiment, said analytes are a carbohydrate. In another embodiment, said carbohydrate is L-Glucose, D-Glucose, D-fructose, L-fructose, D-arabinose, D-xylose, L-xylose, L-mannose, D-galactose, D-sorbitol, mannitol, dulcitol, adonitol, xylitol, L-threitol, maltitol, lactulose, D-lactose, D-maltose, D-trehalose, or maltotriose.

In one embodiment, said analytes are the same or different. In another embodiment, said analytes can be distinct from each other. In another embodiment, said analytes can include the same analytes. For example, when three analytes are included, the first two of the analytes can be the same, and the third analyte is distinct from the first two analytes.

Figure 18:
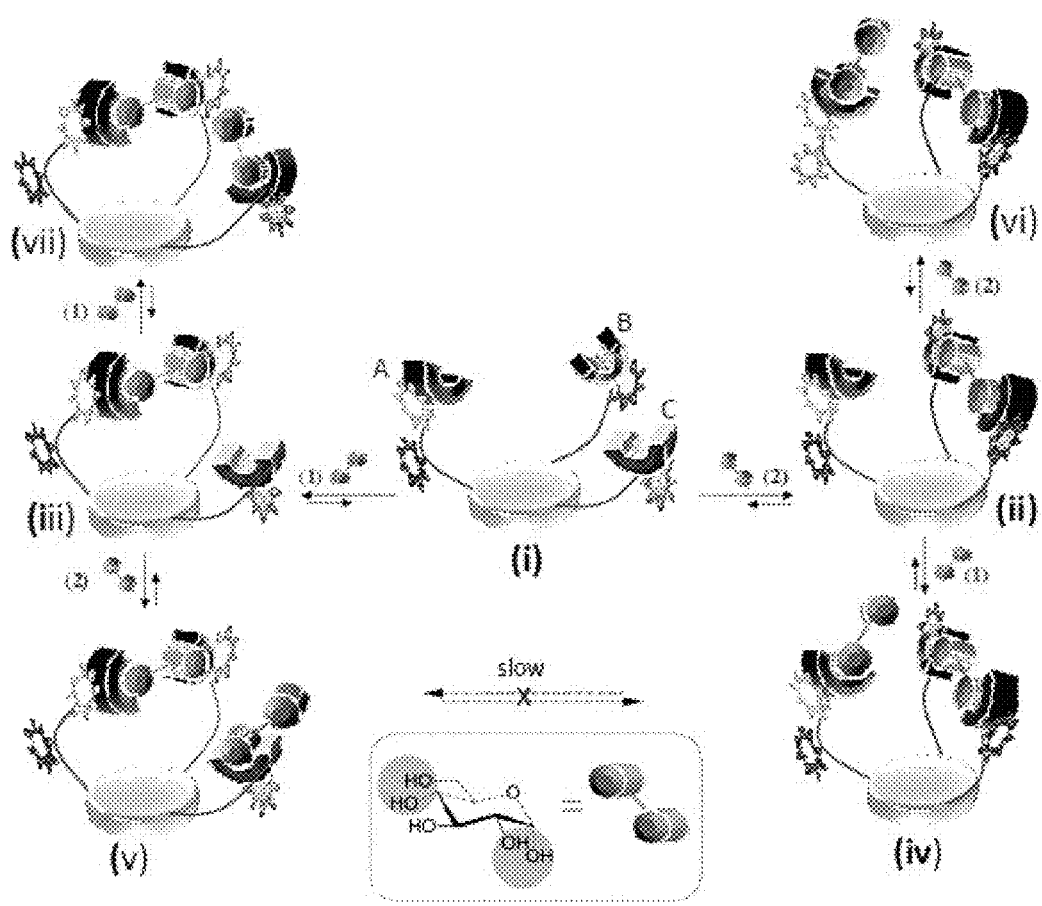
FIG. 18 schematically illustrates an unimolecular combinatorial encoding system function. Possible complexes that can be formed upon addition of two distinct saccharides (1 and 2) in different order (iv Vs. v) or at different concentrations (ii and vi vs. iii and vii), leading to differentiation between 1, 2, 11, 22, 12, 21.

In one embodiment, the term "in a specific sequence" refers to "in a specific order" or "in a particular order." As indicated herein, e.g., FIG. 18, contacting analytes and the compound of the invention in a different sequence would induce the formation of distinct complexes which would exhibit different optical signatures.

In one embodiment, this invention is directed to a method of decoding encoded information using a compound represented by the structure of formula (III),

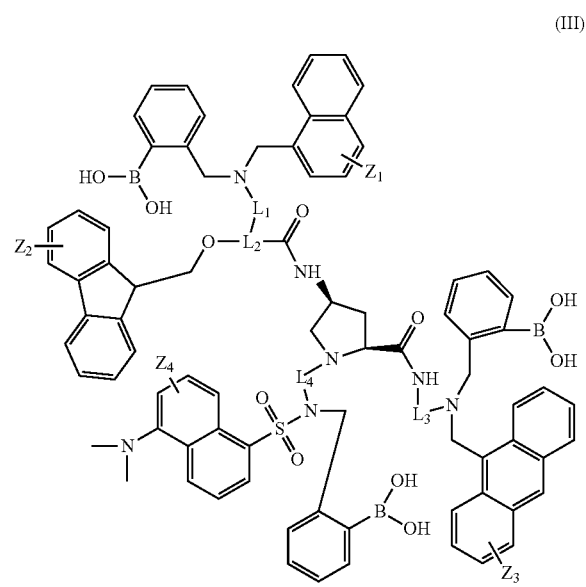

(III)

wherein
$L_1$, $L_2$, $L_3$, $L_4$ are independently a linker, wherein said linker is -alkylene-, —O-alkylene-, —NHC(O)—, —C(O)NH—, —NHC(O)X—, —C(O)NHX—, —C(O)X—, —X'NHC(O)—, —X'C(O)NH—, —X'NHC(O)X—, —X'C(O)NHX—, —X'C(O)X—, —NHX—, —NH-[amino-acid]-C(O)—, —NH-[amino-acid]-C(O)-alkylene-, —C(O)-[amino-acid]-NH—, or —C(O)-[amino-acid]-NH-alkylene-;
X and X' are independently alkylene, haloalkylene, arylene or phenylene; and
$Z_1$, $Z_2$, $Z_3$, $Z_4$ are independently hydrogen, alkyl, alkenyl, haloalkyl, aryl, O-aryl, —(CH$_2$)n-aryl, cycloalkyl, O-cycloalkyl, CF$_3$, F, I, Br, Cl, NO$_2$, CN, N(R')$_2$, COOH, COR', NHCOR', CONHR', (CH$_2$)$_n$NH$_2$, (CH$_2$)$_n$NHR', SR', SH, OR', (CH$_2$)$_n$OH, (CH$_2$)$_n$COOH, or OH; wherein R' is H, alkyl, haloalkyl, dihaloalkyl, trihaloalkyl, aryl, phenyl or halogen; and
n is from 0 to 8;
the method comprising:
a) contacting said compound with between 2 and 7 analytes in a specific sequence to form a complex, wherein said complex exhibits a unique optical signature signal;
b) reading the unique optical signature of the compound; and
c) accessing a database record keyed to the unique optical signature to obtain a code corresponding to a complex of said analytes bound to said compound.

In certain embodiment, n is from 1 to 6.

In one embodiment, $L_1$, $L_2$, $L_3$, $L_4$ are independently -alkylene-, —NHC(O)—, —C(O)NH—, —NHC(O)X—, —C(O)NHX—, —C(O)X—, —X'NHC(O)X—, or —X'C(O)NHX—. In another embodiment, $L_1$ and $L_2$ are independently NHC(O)—, —C(O)NH— —NHC(O)X—, or —C(O)NHX and $L_3$, $L_4$ are independently -alkylene- or —C(O)X—.

In certain embodiment, said compound is represented by the following structure 1:

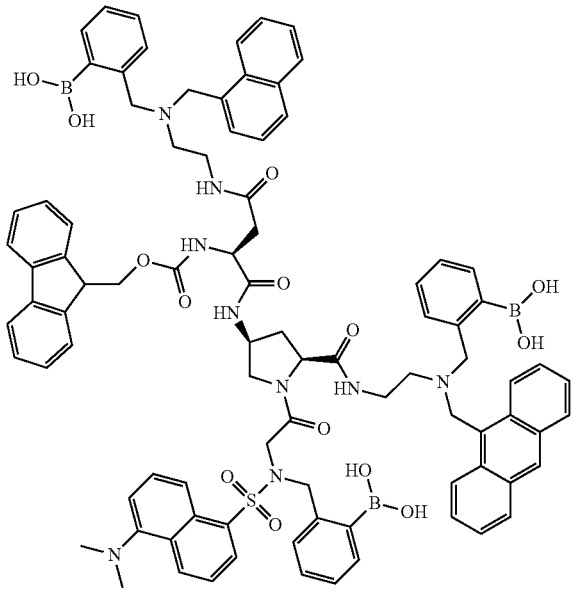

(1)

In one embodiment, said contacting step comprises contacting between 2 and 7 analytes. In another embodiment, 2 or 3 analytes.

In another embodiment, said between 2 and 7 analytes can be any number of analytes. For example, between 2 and 7 analytes. In another embodiment, 2 analytes, 3 analytes, 4 analytes, 5 analytes, 6 analytes, or 7 analytes.

In one embodiment, said analytes are a carbohydrate. In another embodiment, said carbohydrate is L-Glucose, D-Glucose, D-fructose, L-fructose, D-arabinose, D-xylose, L-xylose, L-mannose, D-galactose, D-sorbitol, mannitol, dulcitol, adonitol, xylitol, L-threitol, maltitol, lactulose, D-lactose, D-maltose, D-trehalose, or maltotriose.

In one embodiment, said analytes are the same or different. In another embodiment, said analytes can be distinct from each other. In another embodiment, said analytes can include the same analytes. For example, when three analytes are included, the first two of the analytes can be the same, and the third analyte is distinct from the first two analytes.

In one embodiment, the method further comprises inputting the code corresponding to the complex into a decision point in a program executed by a processor; and executing a program branch of the decision point according to the code.

In another embodiment, the method further comprising inputting the code corresponding to the complex into a hardware logic element of a hardware controller.

The compound of the present invention can be used in an efficient molecular encoding system because it is able to generate unique optical "fingerprints" for a wide range of analytes and thus substantially increases the number of input "keys" that can be processed by the encoding system of this invention. Further, because pattern-generating systems are very efficient in discriminating between input concentrations, the compound of the present invention should be able to distinguish between password entries containing distinct ratios of identical inputs, for example, between 112 and 122. Moreover, the tendency of multivalent receptors to exhibit binding cooperativity and conformational dynamics as well as their ability to be entrapped in kinetically-stable states, should allow the compound of the present invention to distinguish between chemical input sequences.

The compound of the present invention can bind different saccharides in distinct stoichiometries, for example, 1:1, 1:2, or 1:3, and these saccharides can interact with it in a mono-, bi-, or trivalent configuration, thus resulting in distinct optical signatures.

The molecular encoding system of the present invention can be a two state, or three state, or four state, or five state, or six state, or seven state, or more than seven state molecular encoding system. In one embodiment, the molecular encoding system can be a two state molecular encoding system. In another embodiment, the molecular encoding system can be a three state molecular encoding system. In another embodiment, the molecular encoding system can be a four state molecular encoding system. By way of example, when the molecular encoding systems of the present invention is a two state molecular encoding system that respond to different sequences of saccharide pairs, the saccharide pairs can be D-glucose (G) and D-xylose (X), or D-glucose (G) and galactose (L), or D-fructose (F) and maltitol (M). It is the feature of the present invention that the distinct optical signatures can be observed for passwords GX/XG, GL/LG, and FM/MF as described in Example 8. The state of the encoding system is determined by the number of inputs. For example input of D-glucose (G) and D-xylose (X), is a two state molecular encoding system.

The molecular encoding systems of the present invention can distinguish between passwords containing different inputs or different ratios of the same input. For example, the compound of the present invention, e.g., compound 1, recognizes X, G, XX, and GG as distinct code entries.

The method of the present invention enables a unimolecular security system to be 'programmed' to authorize multiple password combinations, as well as passwords assembled from diverse input keys. The later can be selected from a vast library of structurally similar saccharides that are transparent in the visible region; hence, their structure and concentration levels cannot be straightforwardly determined. The security system becomes exceedingly complicated when fluorescence-signaling provides the system with ultimate steganography for breaking such a security system. Specifically, it requires prior knowledge of code entries, as well as access to a molecular-scale security device and to invisible and randomly-selected chemical inputs. An additional layer of protection comes from the fact that the system utilizes both password- and pattern-recognition for user authentication. Thus, unlike electronic encoding systems or biometric locks that rely on a single defense mechanism, the molecular devices can ensure that even if the combination codes or the entry 'keys' are exposed, the system remains secure.

Figure 23:
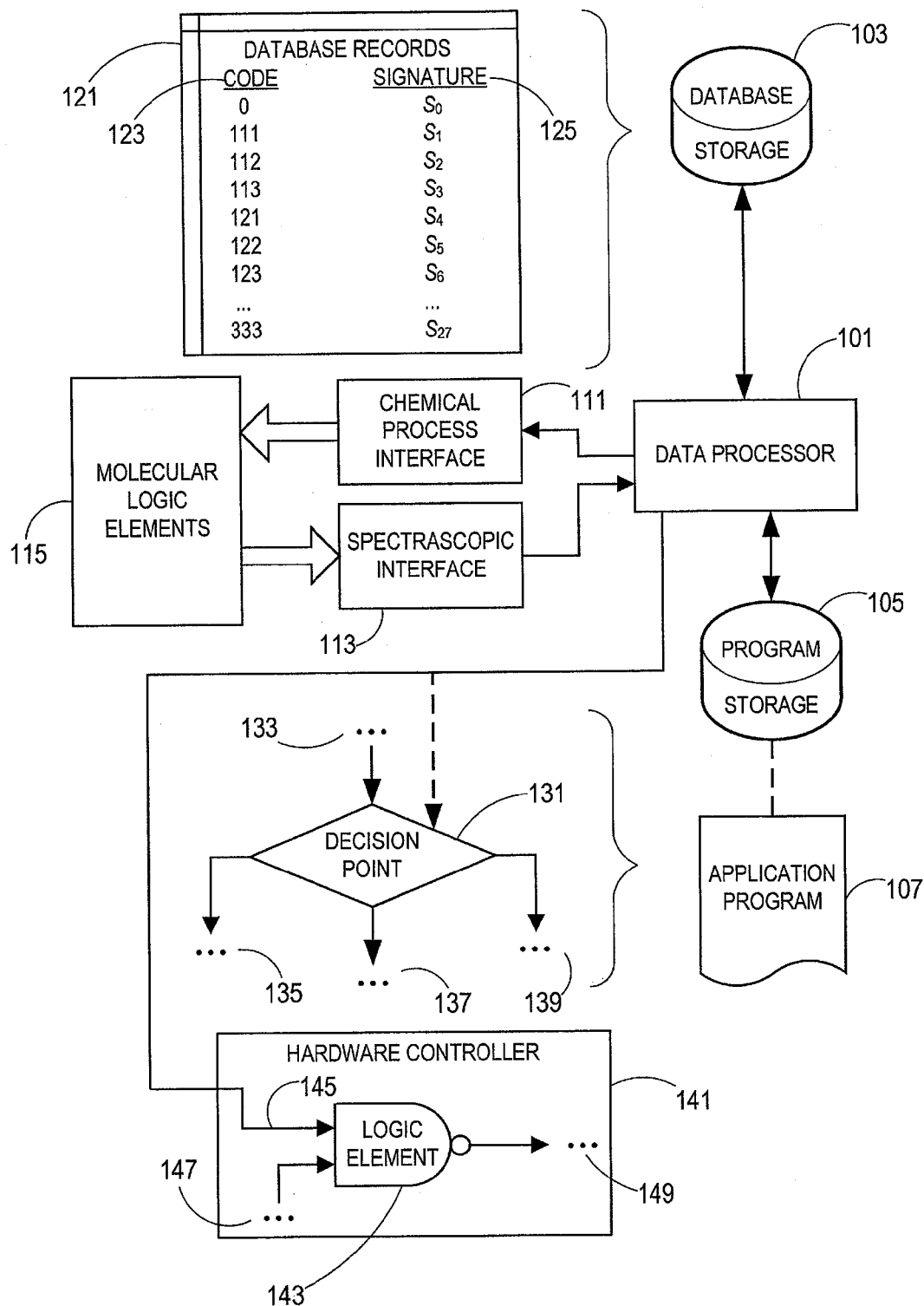
FIG. 23 is a block diagram of an encoding system according to certain embodiments of the present invention.

In one embodiment, the encoding system of this invention is as presented in FIG. 23 wherein a data processor 101 is connected to a non-transitory database storage device 103 and to a non-transitory program storage device 105 for storing application program 107. A chemical process interface 111 provides output control from processor 101 over chemical processes that modify molecular logic elements 115 to represent different data states {these are the "molecular logic elements"). A spectroscopic interface 113 provides input sensing to processor 101 according to the unique optical signature of molecular logic elements 115.

According to an embodiment of the invention, to initialize a database for use, processor 101 stores database records 121 in storage device 105 according to a code field 123 whose code values are according to a predefined encoding scheme and which correspond to the order of analyte binding of molecular logic elements 115 as described herein, which is keyed in database records 121 to a unique optical signature field 125.

In use, molecular logic elements 115 express their binding history {e.g., first binds analyte A, then binds analyte C—} by their unique optical signature, which is input to processor 101 via spectroscopic interface 113. Processor then looks up the corresponding code in database records 121. In an embodiment of the invention the code is input into a software decision point 131 in application program 107. Decision point 131 follows a point 133 in program execution and has multiple branches, illustrated in this non-limiting example as program branches 135, 137, and 139. The branch taken by program execution depends on the code input into decision point 131. In a related embodiment, a hardware controller 141 contains a hardware logic element 143 (illustrated in this non-limiting example as a gate), and the code is input into an input 145. An additional input for another signal is shown as an input 147. Logic element 143 has an output 149 for controlling a function of controller 141 according to the code.

As described above, the state of molecular logic elements 115 can thereby influence the execution of application program 107 and/or control devices via hardware controller 141.

Although embodiments of the invention are not limited in this regard, discussions utilizing terms such as, for example, "processing," "computing," "calculating," "determining," "establishing", "analyzing", "checking", "receiving", "comparing", or the like, refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium, transmission or display devices that may store instructions to perform operations and/or processes.

Embodiments of the present invention may use terms such as, "processor", "computer", "apparatus", "system", "subsystem", "module", "unit", "device" (in single or plural form) for performing the operations herein. This may be specially-constructed for the desired purposes, or may comprise a general purpose computer selectively activated or reconfigured by a computer program stored in the computer.

Some embodiments may be provided in a computer program product that may include a non-transitory machine-readable medium, stored thereon instructions, which may be used to program a computer, or other programmable devices, to perform methods as disclosed herein. Embodiments of the invention may include an article such as a computer or processor non-transitory readable medium, or a computer or processor non-transitory storage medium, such as for example a memory, a disk drive, or a USB flash memory, encoding, including or storing instructions, e.g., computer-executable instructions, which when executed by a processor or controller, carry out methods disclosed herein. The storage medium may include, but is not limited to, any type of disk including floppy disks, optical disks, compact disk read-only memories (CD-ROMs), rewritable compact disk (CD-RWs), and magneto-optical disks, semiconductor devices such as read-only memories (ROMs), random access memories (RAMs), such as a dynamic RAM (DRAM), erasable programmable read-only memories (EPROMs), flash memories, electrically erasable programmable read-only memories (EEPROMs), magnetic or optical cards, or any other type of non-transitory media suitable for storing electronic instructions that are capable of being conveyed via a computer system bus.

A system according to embodiments of the invention may include components such as, but not limited to, a plurality of central processing units (CPU) or any other suitable multi-purpose or specific processors or controllers, a plurality of input units, a plurality of output units, a plurality of memory units, and a plurality of storage units. A system may additionally include other suitable hardware components and/or software components. In some embodiments, a system may include or may be, for example, a personal computer, a desktop computer, a mobile computer, a laptop computer, a notebook computer, a terminal, a workstation, a server computer, a tablet computer, a network device, or any other suitable computing device. Unless explicitly stated, the method embodiments described herein are not constrained to a particular order or sequence. Additionally, some of the described method embodiments or elements thereof can occur or be performed at the same point in time.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently.

The following examples are presented in order to more fully illustrate the preferred embodiments of the invention. They should in no way be construed, however, as limiting the broad scope of the invention.

EXAMPLES

Example 1

Synthesis of Compound 1

Material and Methods:

Chemicals, saccharides, spectroscopic grade solvent, and anhydrous solvents for synthesis were obtained from Sigma Aldrich, and were used without further purification. Fmoc-Asp-O$^t$Bu was purchased from Nova-Biochem. Compound 6 was prepared according to literature procedures (Chen, X. Y., Koch, S.; Uhlenbrock, K.; Weise, K.; Das, D., Gremer, L.; Brunsveld, L.; Wittinghofer, A.; Winter, R.; Triola, G.; Waldmann, H., *Angew. Chem. Int. Ed.* 2010, 49, 6090-6095). Anhydrous solvents were transferred using an oven-dried syringe. Flasks were oven dried under a stream of argon. The Teledyne combiflash was used to purify all the synthetic intermediates. Reverse phase HPLC separations were performed with a Spectra series P200 HPLC system equipped with variable wavelength absorbance detector and a pre-packed Vydac C-18 column. The purity of fractions was ascertained by analytical reverse phase HPLC using a prepacked Chromolith™ Performance RP-18e column. The ¹H NMR spectra of all compounds were recorded on a Bruker Avance 300 MHz spectrometer and the spectrum of the final compound was recorded on Bruker Avance 400 MHz NMR spectrometer. Mass spectra were recorded on a Waters Micromass LC-Q-TOF micro spectrometer. Fluorescent measurements were performed on a VarianTechnology International Fluorimeter. Quartz cuvettes were used for the fluorescence measurements. Principal component analysis of the emission spectra was performed using XLSTAT version 2011.4.03 (32 bit).

Compound 1 is synthesized as presented in FIG. 1.

Synthesis of Compound 3:

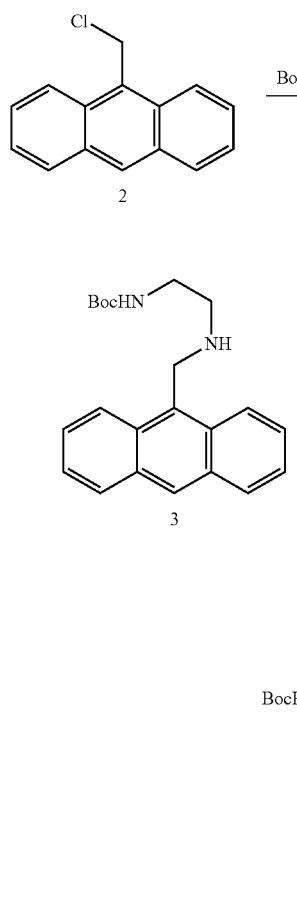

To a stirred solution of N-Boc-ethylenediamine (0.55 g, 3.43 mmol) in dry THF (15 mL) were added 9-chloromethylanthracene 2 (0.04 g, 1.76 mmol) and triethylamine (0.45 mL, 3.11 mmol) under argon. The reaction mixture was refluxed at 90° C. for 2.5 h. The solution was then separated from the solid formed during the reaction and was evaporated to dryness. The crude reaction mass was subjected to combi-flash column chromatography (silica gel, 2% methanol in DCM) to afford 3 (0.4 g) as yellow solid in 65% yield. ¹H NMR (300 MHz, CDCl₃) 1.43 (9H, s), 2.98 (2H, t, J=6 Hz), 3.30 (2H, m, br), 4.73 (2H, s), 4.98 (1H, br), 7.44-7.56 (4H, m), 8.0 (2H, d, J=9 Hz), 8.31 (2H, d, J=9 Hz), 8.41 (1H, s); MS (ESI+): m/z (%)=541.17 (100) [M+H]⁺, 563.11 (15) [M+Na]⁺

Synthesis of Compound 4:

Compound 3 (0.36 g, 1.05 mmol), 2-bromomethyl phenyl boronic acid (0.33 g, 1.5 mmol) and triethylamine (0.29 mL, 2 mmol) were mixed in dry THF (20 mL) and the reaction mixture was refluxed at 90° C. for 2 h. The liquid was separated from the solid using pipette and evaporated to dryness. The crude reaction mass was subjected to combi-flash column chromatography (silica gel, 2% methanol in DCM) to afford 4 (0.32 g) in 63% yield. ¹H NMR (300 MHz, CDCl₃) 1.23 (9H, s), 2.63 (2H, t, br), 3.10 (2H, t, br), 3.90 (2H, s), 4.50 (2H, s), 7.35 (3H, s), 7.39-7.46 (4H, m), 7.85 (1H, s, br), 7.93-7.96 (2H, m), 8.06 (2H, d, br), 8.38 (1H, s); MS (ESI+): m/z (%)=485.19 (35) [M+H]⁺, 499.20 (40) [M+H−H₂O+MeOH]⁺, 507.12 (100) [M+Na]⁺, 521.20 (70) [M−H₂O+MeOH+Na]⁺

Synthesis of Compound 7:

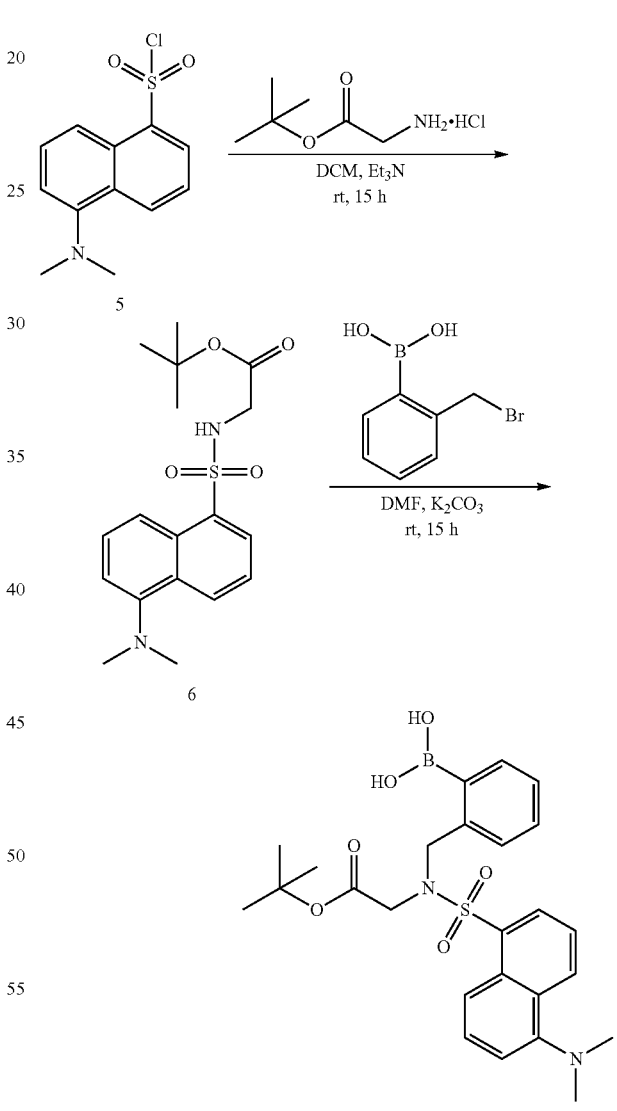

To sulphonamide 6 (0.36 g, 1.05 mmol) in anhydrous DMF (20 mL) were added 2-bromomethyl phenyl boronic acid (0.33 g, 1.5 mmol) and K₂CO₃ (0.29 mg, 2 mmol) under argon. The reaction mixture was stirred at room temperature for 15 h. The solvent was evaporated and the residue was dissolved in ethyl acetate (50 mL) and washed twice with water (50 mL) followed by brine (20 mL). The organic layer was dried over anhydrous sodium sulphate and evaporated to dryness. The crude reaction mass was subjected to combi-flash column chromatography (silica gel, 2% MeOH in DCM) to furnish 7 (0.32 g) in 80% yield (based on starting material recovery). $^1$H NMR (300 MHz, CD$_3$OD) 1.14 (9H, s), 3.14 (6H, s), 3.87 (2H, s), 4.73 (2H, s), 7.10 (1H, d, J=6 Hz), 7.22-7.32 (2H, m), 7.35 (1H, d, J=6 Hz), 7.63 (1H, d, J=9 Hz), 7.69-7.76 (2H, m), 8.36 (1H, d, J=6 Hz), 8.58 (1H, d, J=9 Hz) 8.68 (1H, d, J=9 Hz); MS (ESI+): m/z (%)=549.09 (100) [M−2H$_2$O+2MeOH+Na]$^+$, 1075.20 (20) [2(M−2H$_2$O+2MeOH)+Na]$^+$ Synthesis of Compound 9:

Synthesis of Compound 10:

To a stirred solution of 9 (0.3 g, 0.9 mmol) in dry THF (20 mL) were added 2-bromomethyl phenyl boronic acid (0.32 g, 1.5 mmol) and triethylamine (0.28 mL, 2 mmol) under argon. The solution was refluxed for 6 h at 90° C. Upon completion of the reaction, the reaction mixture was cooled to room temperature and the solution was separated from the solid using pippette. The organic layer was evaporated and the crude reaction mass was subjected to combi-flash column chromatography (silica gel, 2% MeOH in DCM) to obtain 10 (0.32 g) as a white solid in 69% yield. $^1$H NMR (300 MHz, CD$_3$OD) 1.37 (9H, s), 2.80 (2H, t, J 6 Hz), 3.27 (2H, t, J=6 Hz), 4.05 (2H, s), 4.27 (2H, s), 7.29-7.36 (3H, m), 7.46-7.51 (3H, m), 7.56 (1H, s, br), 7.61 (1H, d, J=9 Hz), 7.87-7.91 (2H, m), 7.94 (1H, d, J=9 Hz); MS (ESI+): m/z (%)=435.29 (35) [M+H]$^+$, 449.30 (100) [M+H−H$_2$O+MeOH]$^+$, 463.31 (55) [M+H−2H$_2$O+2MeOH]$^+$, 471.28 (20) [M−H$_2$O+MeOH+Na]$^+$, 485.31 (75) [M−2H$_2$O+2MeOH+Na]$^+$ Synthesis of Compound 12:

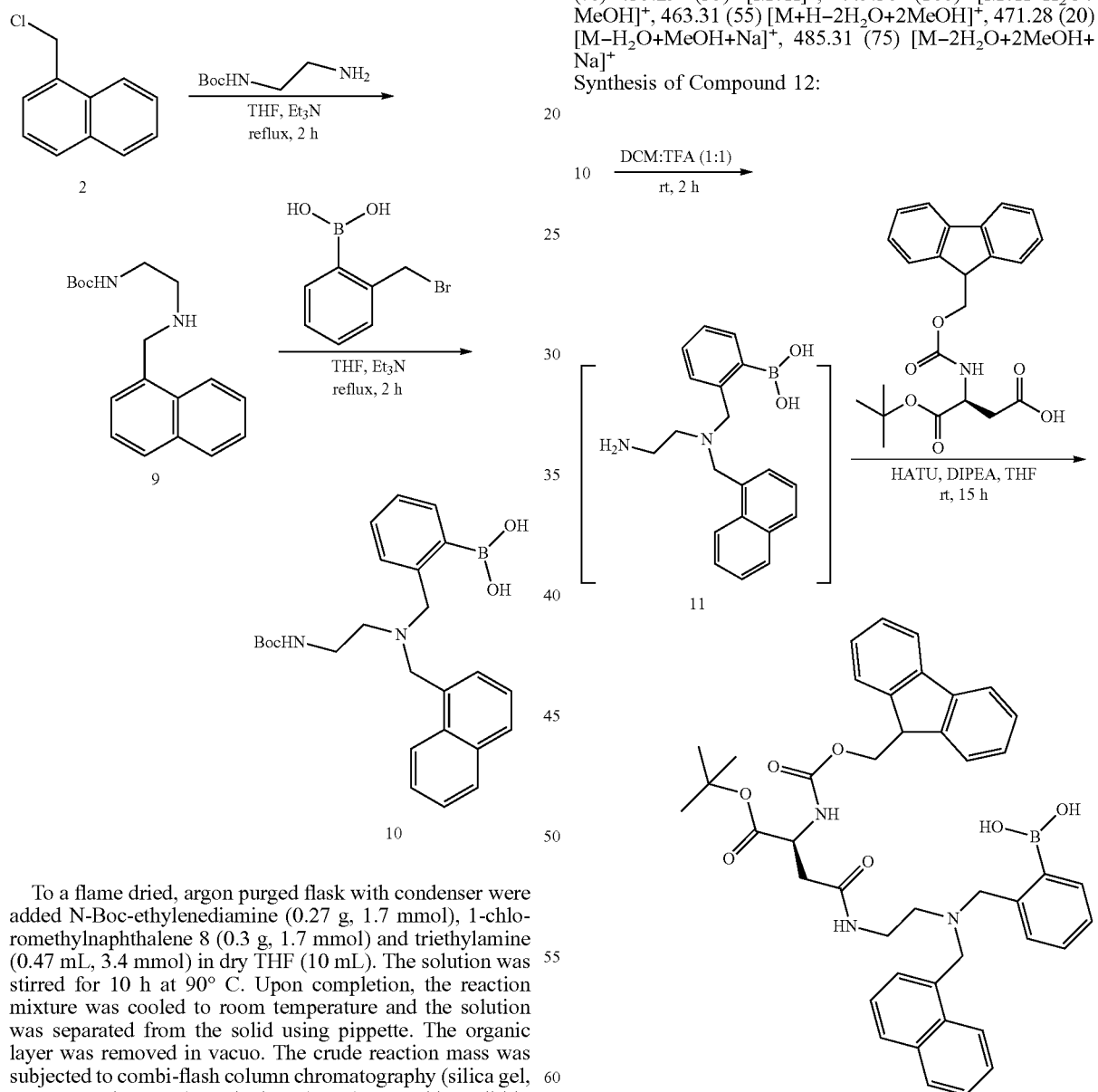

To a flame dried, argon purged flask with condenser were added N-Boc-ethylenediamine (0.27 g, 1.7 mmol), 1-chloromethylnaphthalene 8 (0.3 g, 1.7 mmol) and triethylamine (0.47 mL, 3.4 mmol) in dry THF (10 mL). The solution was stirred for 10 h at 90° C. Upon completion, the reaction mixture was cooled to room temperature and the solution was separated from the solid using pippette. The organic layer was removed in vacuo. The crude reaction mass was subjected to combi-flash column chromatography (silica gel, 2% MeOH in DCM) to obtain 9 (0.3 g) as a white solid in 55% yield. $^1$H NMR (300 MHz, CDCl$_3$) 1.42 (9H, s), 2.85 (2H, t, J=7.5 MHz), 3.26 (2H, m, br), 4.23 (2H, s), 4.97 (1H, s, br), 7.41-7.53 (4H, m), 7.77 (1H, d, J=6 Hz), 7.86 (1H, d, J=6 Hz), 8.10 (1H, d, J=6 Hz); MS (ESI+): m/z (%)=301.24 (100) [M+H]$^+$, 601.40 (95) [2M+H]$^+$, 623.40 (35) [2M+Na]$^+$.

To a solution of 10 (0.2 g, 0.46 mmol) in DCM (1 mL) was added trifluoroacetic acid (1 mL) and the reaction was stirred for 2 h at room temperature. After completion of the reaction, the solvent was evaporated for 5 h under high vacuum. The crude solid 11 was dissolved in dry THF (10 mL) and the solution was basified to pH~7-8 with DIPEA (0.18 mL, 0.92 mmol). In the following step, N-α-Fmoc-L-aspartic acid α-t-butylester (0.19 g, 0.46 mmol) and HATU (0.17 g, 0.46 mmol) were added and the reaction mixture was stirred at room temperature for 15 h under argon. The solvent was evaporated and the crude mass was subjected to combi-flash column chromatography (silica gel, 3% MeOH in DCM) to furnish 12 (0.2 g) in 60% yield. $^1$H NMR (300 MHz, CD$_3$OD) 1.41 (9H, s), 2.21-2.37 (2H, m), 3.24 (2H, s), 3.44 (2H, t, br), 4.20 (1H, t, J=7.5 Hz), 4.31-4.39 (3H, m), 4.64 (2H, s, br), 4.90 (2H, s), 7.28-7.34 (2H, m), 7.39-7.44 (2H, m), 7.49-7.57 (6H, m), 7.60-7.65 (2H, m), 7.79-7.83 (5H, m), 7.94-7.97 (1H, m), 8.03 (1H, d, J=9 Hz); MS (ESI+): m/z (%)=728.44 (10) [M+H]$^+$, 742.45 (60) [M+H−H$_2$O+MeOH]$^+$, 756.46 (60) [M+H−2H$_2$O+2MeOH]$^+$, 764.38 (55) [M−H$_2$O+MeOH+Na]$^+$, 778.39 (100) [M−2H$_2$O+2MeOH+Na]$^+$ Synthesis of Compound 13:

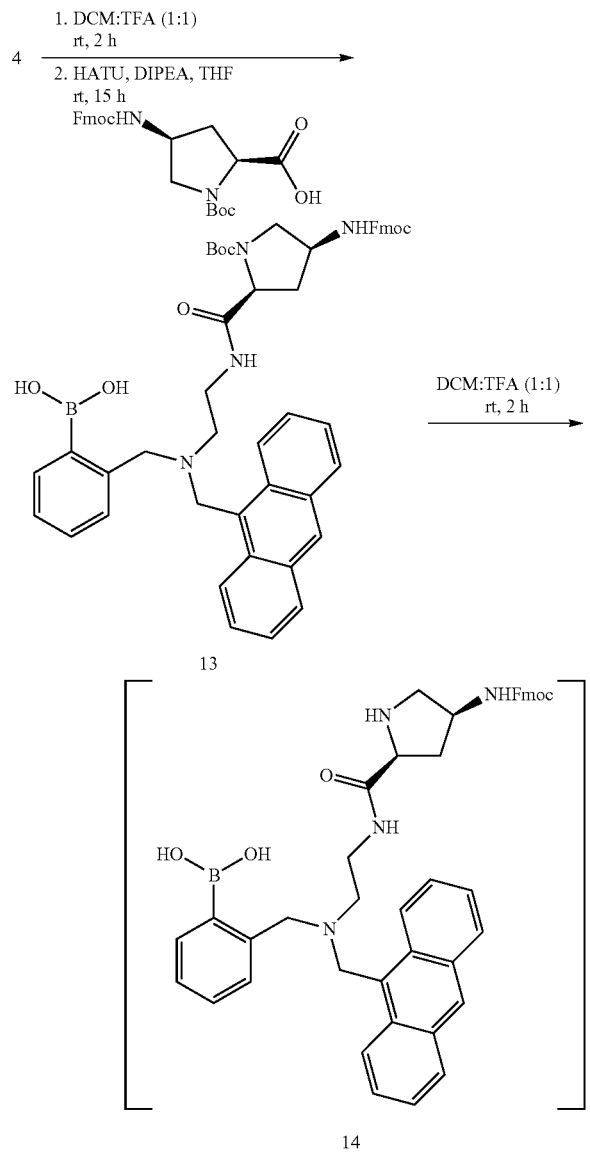

Compound 4 (0.22 g, 0.45 mmol) was dissolved in DCM (1 mL) and the solution was cooled to 0° C. Trifluoroacetic acid was dripped into the solution and the reaction was slowly warmed to room temperature. After 2 h, the solvent was evaporated and the residue was dried for 5 h under high vacuum. The crude solid was dissolved in THF (10 mL) and the solution was basified to pH~7-8 with DIPEA (0.17 mL, 0.90 mmol). In the following step, N-Boc-cis-4-N-Fmoc-amino-L-proline (0.20 g, 0.45 mmol) and HATU (0.17 g, 0.45 mmol) were added and the reaction mixture was stirred at room temperature for 15 h under argon. The solvent was removed in vacuo and the crude mass was subjected to combi-flash column chromatography (silica gel, 3% MeOH in DCM) to afford 13 (0.2 g) in 54% yield. $^1$H NMR (300 MHz, CD$_3$OD) 1.20 (9H, s), 1.96-2.06 (2H, m), 2.62 (2H, s), 3.13 (2H, m, br), 3.33 (1H, s), 3.56-3.62 (2H, m), 3.78-3.82 (1H, d, br), 3.88 (1H, s, br), 4.00-4.04 (1H, t, br), 4.10-4.15 (1H, t, br), 4.35 (2H, m), 4.45 (2H, s), 7.24-7.43 (11H, m), 7.59 (2H, d, J=9 Hz), 7.59 (1H, br), 7.72 (2H, d, J=9 Hz), 7.89 (2H, d, J=6 Hz), 8.11 (2H, d, J=6 Hz), 8.31 (1H, s); MS (ESI+): m/z (%)=819.46 (5) [M+H]$^+$, 833.47 (20) [M+H−H$_2$O+MeOH]$^+$, 847.48 (15) [M+H−2H$_2$O+2MeOH]$^+$, 855.46 (25) [M−H$_2$O+MeOH+Na]$^+$, 869.47 (100) [M−2H$_2$O+2MeOH+Na]$^+$ Synthesis of Compound 14:

Trifluoroacetic acid (0.5 mL) was added dropwise to a solution of 13 (0.12 g, 0.165 mmol) in DCM (0.5 mL). The reaction was stirred at room temperature for 2 h. After consumption of the starting material, the solvents were removed under reduced pressure. The reaction mixture was dried for 5 h under high vacuum to afford 14 (0.07 g) in quantitative yield.

Synthesis of Compound 15:

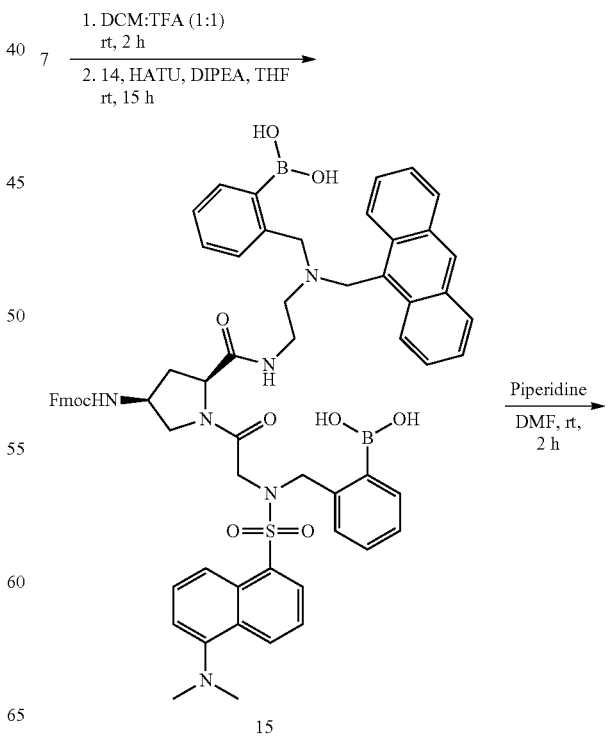

-continued

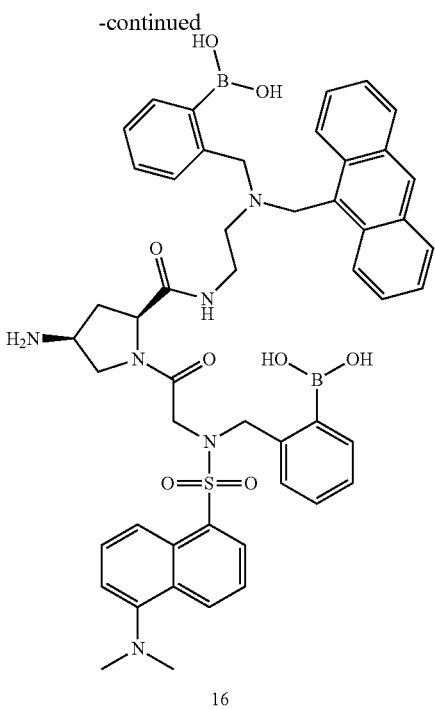

16

To compound 7 (0.08 g, 0.165 mmol) in DCM (0.5 mL) was added trifluoroacetic acid (0.5 mL) at room temperature. The reaction mixture was stirred for 2 h. Upon completion, the solvent was evaporated for 5 h under high vacuum and the crude solid was re-dissolved in dry THF (10 mL). The stirred solution was basified with DIPEA (0.06 mL, 0.33 mmol) to obtain pH~7-8 followed by the addition of 14 (0.07 g, 0.165 mmol) and HATU (0.06 g, 0.165 mmol) under argon. After 15 h, the solvent was removed under vacuum and the crude mass was subjected to combi-flash column chromatography (silica gel, 3% MeOH in DCM) to obtain a light yellowish solid 15 (0.07 g) in 37% yield. $^1$H NMR (300 MHz, CD$_3$OD) 2.60 (2H, s), 2.82 (6H, s), 3.07-3.19 (3H, m), 3.37 (1H, s), 3.71 (1H, s, br), 3.83 (2H, d, br), 3.65-3.75 (1H, m), 3.98 (2H, s, br), 4.03 (2H, d, br), 4.33 (2H, s, br), 4.46-4.64 (5H, m, br), 6.84-6.91 (1H, m), 6.95-7.15 (2H, m), 7.19 (2H, d, J=6 Hz), 7.25-7.45 (12H, m), 7.47-7.56 (4H, m), 7.71-7.77 (2H, m), 7.91 (2H, d, J=9 Hz), 8.12-8.15 (2H, d, br), 8.27-8.35 (3H, m), 8.51 (1H, d, J=9 Hz); MS (ESI+): m/z (%)=1165 (10) [M+Na]$^+$, 622.32 (45) [M−4H$_2$O+4MeOH+2Na]$^{+2}$, 1207.21 (20) [M−3H$_2$O+3MeOH+Na]$^+$, 1221.27 (100) [M−4H$_2$O+4MeOH+Na]$^+$ Synthesis of Compound 16:

The bisboronic acid 15 (0.05 g) was dissolved in a solution of 20% piperidine in DMF (1.5 mL). The reaction mixture was stirred at room temperature for 2 h. The solvent was removed at 40° C. using high vacuum and the crude reaction mass was purified by reverse phase HPLC. A binary gradient was made taking solution A (0.1% TFA in H$_2$O) and solution B (0.1% TFA in acetonitrile: H$_2$O; 3:1, v:v). The gradient used in HPLC was 15% B to 80% B over 80 min. The column effluents were monitored by UV absorbance at 220 nm. The purity of fractions were checked by reverse phase analytical HPLC with 10-100% B over 10 min with a flow rate of 3 ml/min. Pure fractions were collected and lyophilized to afford a light yellowish amine 16 (0.025 g) in 78% yield (HPLC purity=100%, Retention time=8.42 min). $^1$H NMR (300 MHz, CD$_3$OD) 2.02 (2H, d, J=15 Hz), 2.45-2.50 (2H, m), 2.90 (1H, s), 2.95 (6H, s), 3.47 (2H, s, br), 3.71 (4H, s, br), 3.98-4.04 (2H, m), 4.33 (2H, m), 4.50 (2H, d, J=12 Hz), 4.65 (1H, s, br), 5.43 (2H, s), 6.53 (1H, d, J=9 Hz), 6.96 (1H, t, J=7.5 Hz), 7.18 (1H, t, J=9 Hz), 7.25 (1H, d, J=9 Hz), 7.36 (1H, d, J=9 Hz), 7.49-7.62 (9H, m), 7.84 (1H, br), 8.02 (1H, br), 8.12 (2H, d, J=9 Hz), 8.34 (2H, t, J=9 Hz), 8.59 (2H, d, J=9 Hz), 8.69 (1H, s); MS (ESI+): m/z (%)=489.31 (40) [M+2H−4H$_2$O+4MeOH]$^{+2}$, 500.40 (65) [M+H−4H$_2$O+4MeOH+Na]$^{+2}$, 963.53 (45) [M+H−3H$_2$O+3MeOH]$^+$, 977.47 (100) [M+H−4H$_2$O+4MeOH]$^+$ Synthesis of Compound 1:

12 → 1. DCM:TFA (1:1) rt, 2 h
2. 16, HATU, DIPEA, THF rt, 15 h

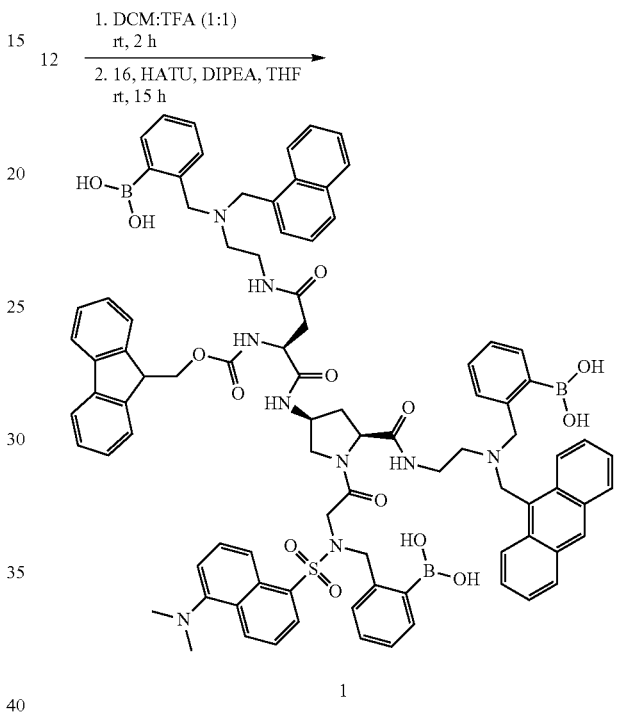

1

To an oven dried argon purged flask were added t-butylester 12 (0.025 g, 0.029 mmol) in DCM (0.5 mL) and trifluoroacetic acid (0.5 mL). The reaction mixture was stirred for 2 h at room temperature. Upon completion, the solvent was evaporated for 5 h in high vacuum and redissolved in dry THF (10 mL). The solution was basified to pH~7-8 with DIPEA (0.02 mL, 0.11 mmol), then amine 16 (0.07 g, 0.165 mmol) and HATU (0.011 g, 0.029 mmol) were added. The reaction was stirred at room temperature for 12 h under an argon atmosphere. The solvent was evaporated and the crude mass was purified by reverse phase HPLC. A binary gradient was made taking solution A (0.1% TFA in H$_2$O) and solution B (0.1% TFA in acetonitrile: H$_2$O; 3:1, v:v). The gradient used in HPLC was 40% B to 100% B over 80 min. The column effluents were monitored by UV absorbance at 220 nm. The purity of fractions were checked by reverse phase analytical HPLC with 10-100% B over 10 min with a flow rate of 3 ml/min. Pure fractions were collected and lyophilized to afford a light yellowish solid 1 (0.004 g) in 8.3% yield (HPLC purity=98.7%, Retention time=11.1 min). $^1$H NMR (400 MHz, CD$_3$OD) 2.19-2.30 (2H, m), 2.32-2.43 (2H, m), 2.49-2.65 (2H, m), 2.89 (6H, s), 3.20 (1H, br), 3.36 (3H, s, br), 3.45 (1H, s), 3.48-3.50 (1H, m), 3.55-3.65 (1H, m, br), 3.94 (1H, dd, J=5.1, 12.1 Hz), 4.08 (2H, t, J=7.1 Hz), 4.15-4.16 (2H, m), 4.24-4.29 (3H, m), 4.32-4.36 (3H, m), 4.39-4.47 (3H, m), 4.58 (2H, d, br), 4.68 (2H, s, br), 6.62 (1H, t, J=7.2 Hz), 6.88 (1H, t, J=8.3 Hz), 6.99 (1H, t, J=7.5 Hz), 7.14-7.18 (3H, m), 7.20-7.31 (5H, m), 7.45-7.53 (15H, m), 7.66-7.68 (2H, m, br), 7.67 (1H, d, J=7.5 Hz), 7.73-7.77 (2H, br), 7.75 (1H, t, J=7.1 Hz), 7.89 (2H, d, J=8.6 Hz), 7.95 (2H, d, J=8.3 Hz), 8.09 (2H, d, J=7.7 Hz), 8.39 (2H, t, J=10 Hz), 8.56 (1H, d, J=8.6 Hz), 8.66 (1H, s); MS (ESI+): m/z (%)=787.90 (10) $[M+2H]^{+2}$, 794.80 (40) $[M+2H-H_2O+MeOH]^{+2}$, 815.91 (75) $[M+2H-4H_2O+4MeOH]^{+2}$, 822.82 (70) $[M+2H-5H_2O+5MeOH]^{+2}$, 829.73 (20) $[M+2H-6H_2O+6MeOH]^{+2}$, 1575.36 (5) $[M+H]^+$, 1588.60 (5) $[M+H-H_2O+MeOH]^+$, 1602.54 (5) $[M+H-2H_2O+2MeOH]^+$, 1616.60 (5) $[M+H-3H_2O+3MeOH]^+$, 1630.48 (10) $[M+H-4H_2O+4MeOH]^+$, 1644.67 (10) $[M+H-5H_2O+5MeOH]^+$, 1658.55 (5) $[M+H-6H_2O+6MeOH]^+$. Exact mass: $[M+H-5H_2O+5MeOH]^+$ $C_{94}H_{101}B_3N_9O_{14}S$ calc. 1644.7468; found 1644.7496.

Example 2

Fluorescence Measurements of Molecular Differential Sensor of Compound 1 with Saccharides A solution of compound 1 (3 µM, 60 µL) in PBS:MeOH (1:1, pH=7.28) (FIG. 7a), HEPES:MeOH (1:1, pH=7.5) (FIG. 7b), or methanol (FIG. 6) was mixed with a solution of a saccharide in water (1M or 100 mM, 3 µL). The solution mixture was allowed to equilibrate for 6 min. Fluorescence measurements were taken in a 3 mm cuvette using 295-1100 nm emission filter and 10 nm excitation and emission slit width. The spectra were recorded at a rate of 120 nm per min. In all spectra, the emission of the pure sensor (none) corresponds to an addition of only water.

Figure 6:
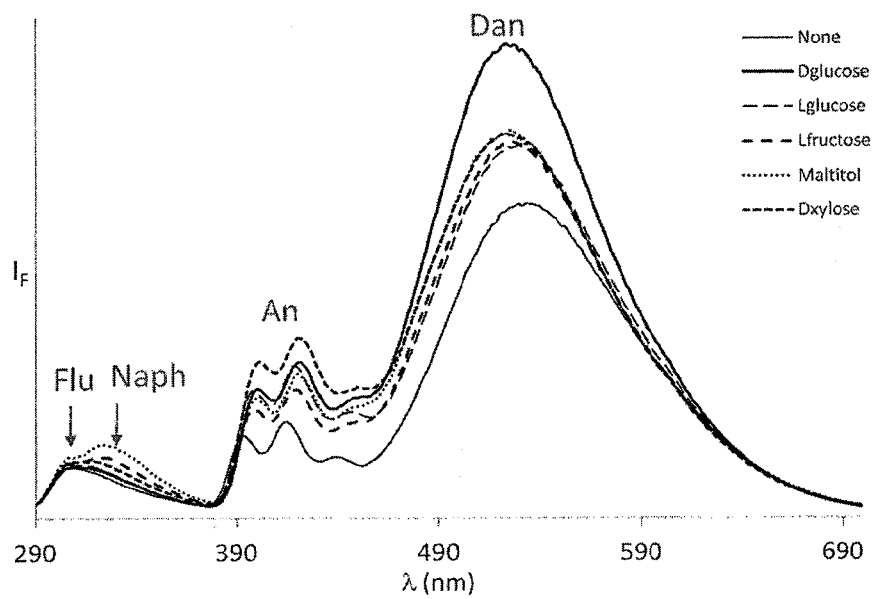
FIG. 6 depicts changes in fluorescence emission spectrum of compound 1 upon addition of D-glucose, L-glucose, L-fructose, maltitol, and D-xylose. Conditions: 4.8 mM of saccharide and 3.3 µM of sensor in methanol (5% water) excited at 270 nm.
Figure 7A:
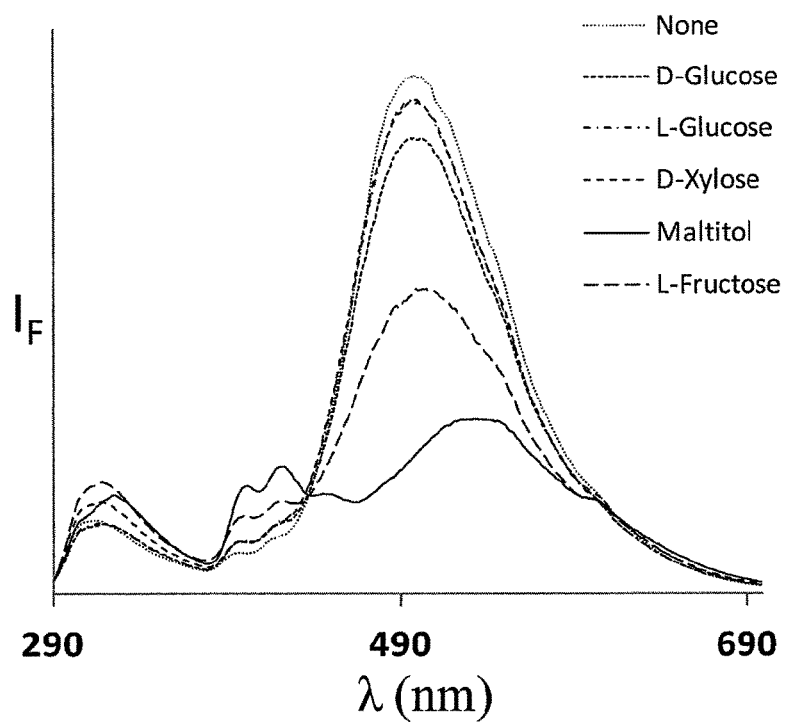
FIG. 7A-7C depict fluorescence emission spectra of compound 1 in PBS:MeOH (1:1, pH=7.28) (FIG. 7A), HEPES: MeOH (1:1, pH=7.5) upon addition of different saccharides (48 mM) (FIG. 7B) and PCA graph for the repeat experiments of five saccharides in PBS:Methanol (1:1, pH=7.28) (FIG. 7C). Excitation wavelength: 270 nm.
Figure 7B:
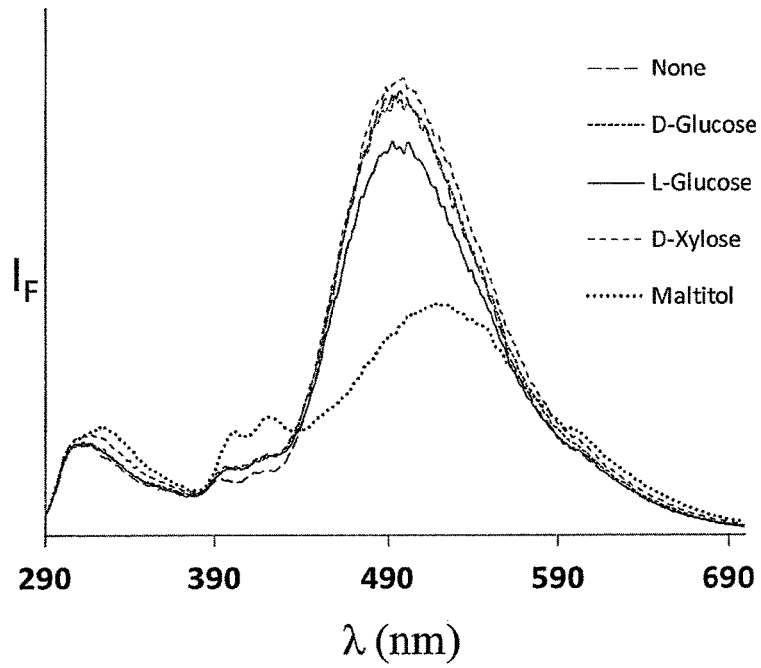

FIGS. 6 and 7 present fluorescence emission spectra of compound 1 upon addition of several saccharides. The binding of compound 1 and each saccharide provide a unique fingerprint (optical signature).

Exciting compound 1 at 270 nm (FIG. 4) resulted in fluorescence emission across the UV-Vis spectrum owing to intramolecular FRET processes. Adding L-glucose led to enhancement in both anthracene (58%) and dansyl (18%) emissions as well as to a hypsochromic shift in dansyl fluorescence. Almost no change was observed in the UV region. D-glucose generated a pattern similar to that of L-glucose in the naphthalene, fluorenyl, and antharacene emission regions; however, it induced a much stronger increase in dansyl emission (51%). In contrast, the pattern generated by L-fructose differs from D-glucose mainly in the UV region where a 30% enhancement in naphthalene's fluorescence intensity was observed. Finally, maltitol and Dxylose can be easily distinguished from the other three saccharides because they induced the largest change in the emission of naphthalene (54%) and anthracene (85%), respectively.

Example 3

PCA of Molecular Differential Sensor of Compound 1 with Saccharides

Figure 7C:
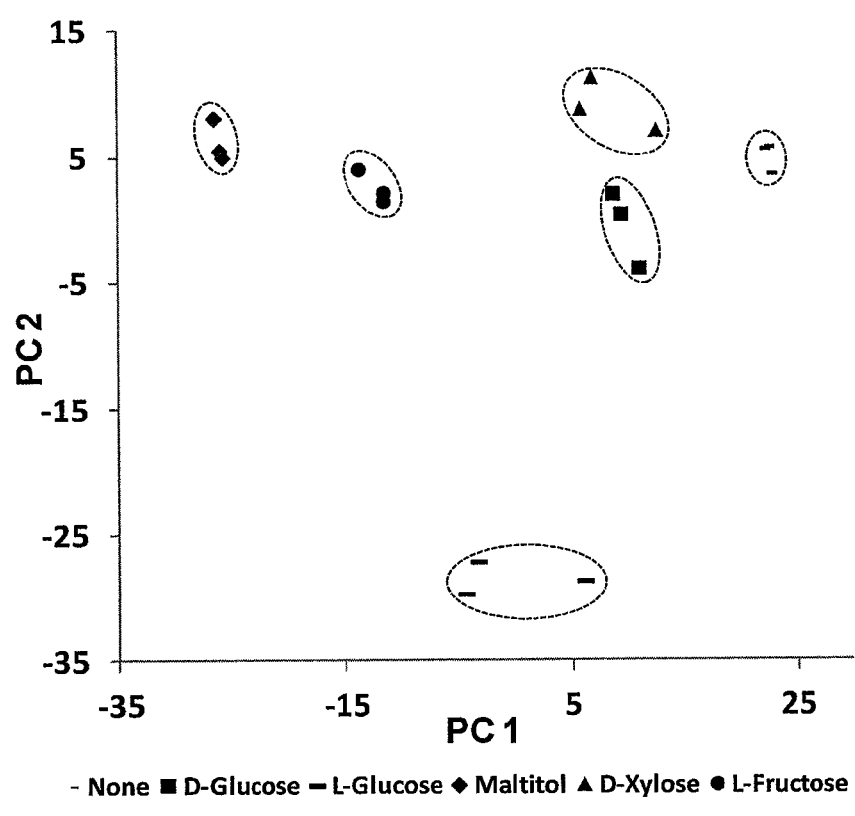

The fluorescence emission for compound 1 with different saccharides (48 mM) in PBS buffer:MeOH (1:1, pH=7.28) were performed and analyzed using principal component analysis (PCA) (FIG. 7c). Each cluster represents multiple trials for each saccharide.

Figure 8:
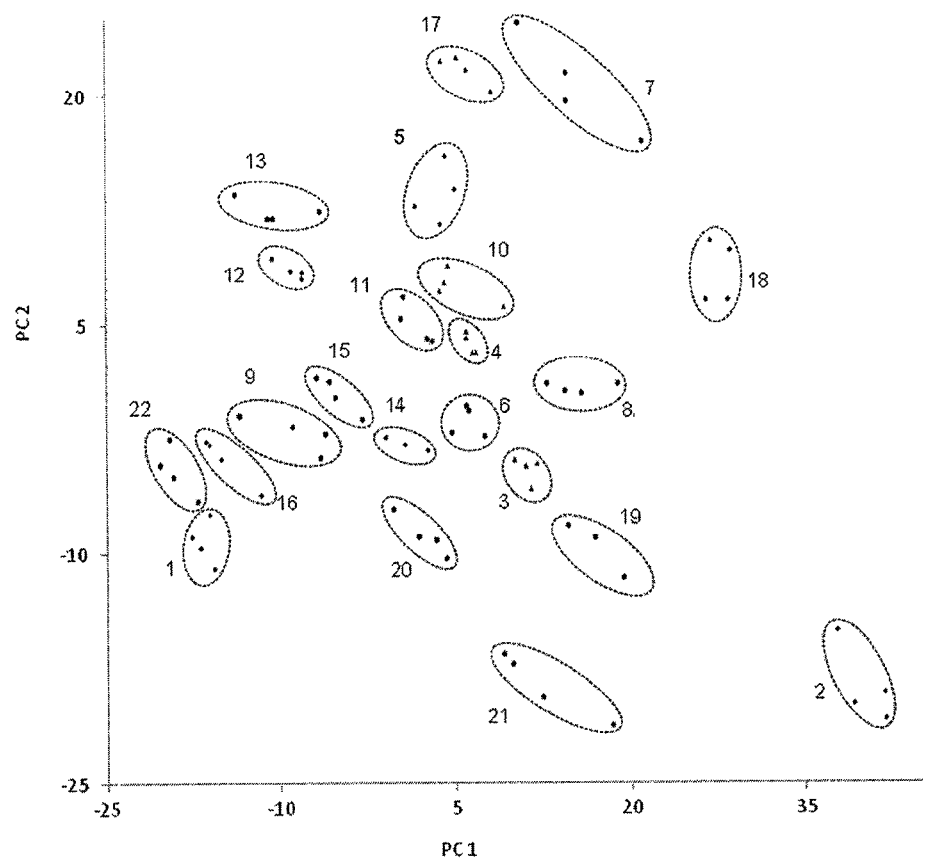
FIG. 8 depicts a PCA mapping of emission patterns generated by various saccharides. 1) None; 2) D-glucose; 3) L-glucose; 4) D-fructose; 5) L-fructose; 6) D-arabinose; 7) D-xylose; 8) L-xylose; 9) L-mannose; 10) D-galactose; 11) D-sorbitol; 12) mannitol; 13) dulcitol; 14) adonitol; 15) xylitol; 16) L-threitol; 17) maltitol; 18) lactulose; 19) D-lactose; 20) D-maltose; 21) D-trehalose; 22) maltotriose.

Principal component analysis (PCA) was used to distinguish between these patterns as well as between optical signatures generated by other saccharides under the same conditions (FIG. 8). To ensure reproducibility, each experiment was repeated four times. The PCA plot showed a clear differentiation between a variety of structurally similar sugars, including ring-forming monosaccharides (2-10), linear sugar alcohols (i.e. reduced monosaccharides) (11-17), disaccharides (18-21), and a trisaccharide (22). Therefore, these results confirm the feasibility of discriminating between numerous closely related analytes using a single fluorescent molecular sensor.

Example 4

Excitation and Emission of Dyes

Figure 3A:
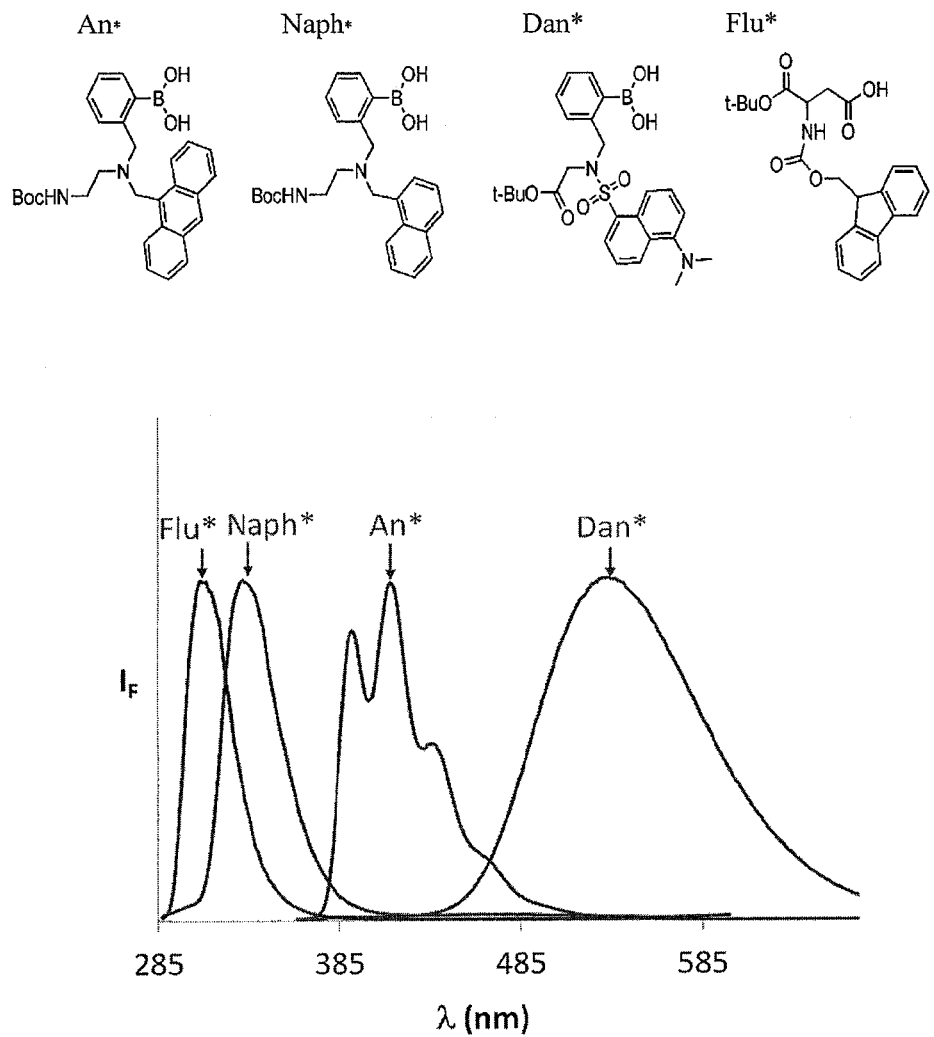
FIGS. 3A and 3B depict normalized excitation (FIG. 3A) and emission (FIG. 3B) spectra of fluorenyl-aspartic acid (Flu*), naphthalene-boronic acid (Naph*), antharacene-boronic acid (An*) and dansyl-boronic acid (Dan*) derivatives in a methanol solution. The emission spectra of Flu* and Naph* were obtained under an excitation wavelength of 270 nm using 295-1100 nm filter, whereas the emissions of An* and Dan* were recorded while exciting at 345 nm using 360-1100 nm filter.
Figure 3B:
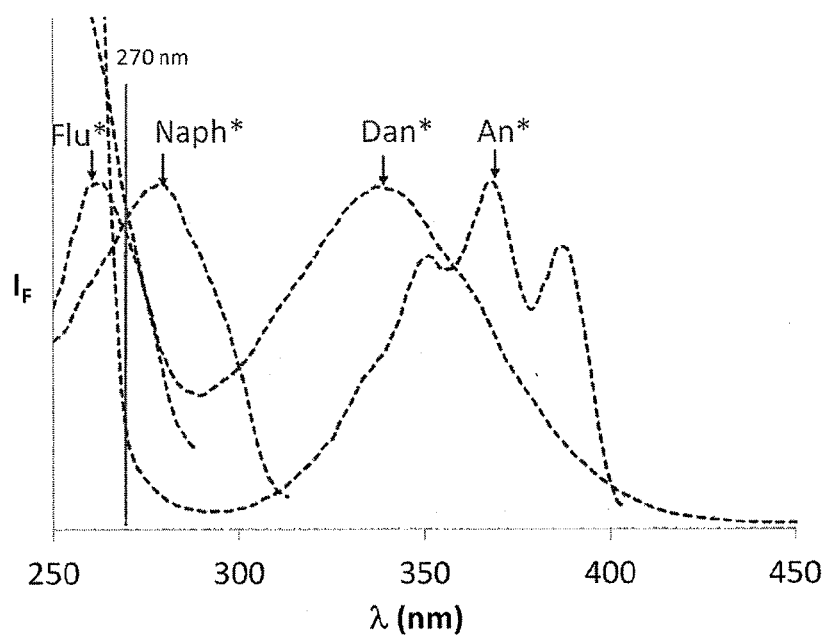

FIG. 3A-3B present the excitation (FIG. 3A) and emission (FIG. 3B) spectra of the individual fluorescent dyes, namely, each boronic acid-dye pair (e.g., Naph*, An*, and Dan*) and a fluorenyl-aspartic acid derivative (Flu*). The emission spectra of naphthalene and fluorenyl overlap with the excitation spectra of antharacene and dansyl. Therefore, illuminating at 270 nm resulted in an emission pattern ranging across the UV-Vis spectrum (FIG. 5) due to FRET between the donors (e.g., naphthalene and fluorenyl) and acceptors (e.g., dansyl and anthracene) as well as direct excitations, mainly of naphthalene, fluorenyl, and dansyl. An additional energy transfer process that occurred to a lesser extent involved FRET between anthracene and dansyl (see FIG. 4).

Solution of N-α-Fmoc-L-aspartic acid α-t-butylester (Flu*), naphthalene boronic acid derivative 10 (Naph*), anthracene boronic acid derivative 4 (An*), dansyl boronic derivative 7 (Dan*) in methanol were prepared. The excitation spectra of Flu*, Naph*, An*, Dan* were recorded while setting the emission wavelengths to 307 nm, 330 nm, 416 nm (using 360-1100 nm filter) and 521 nm (using 360-1100 nm filter), respectively. The emission spectra of Flu* and Naph* were obtained under an excitation wavelength of 270 nm using 295-1100 nm filter, whereas the emissions of An* and Dan* were recorded while exciting at 345 nm using 350-1100 nm filter. (FIG. 3B) The slit widths were set to 10 nm for both excitation and emission measurements. The spectra were scanned at a rate of 120 nm per min.

Figure 4:
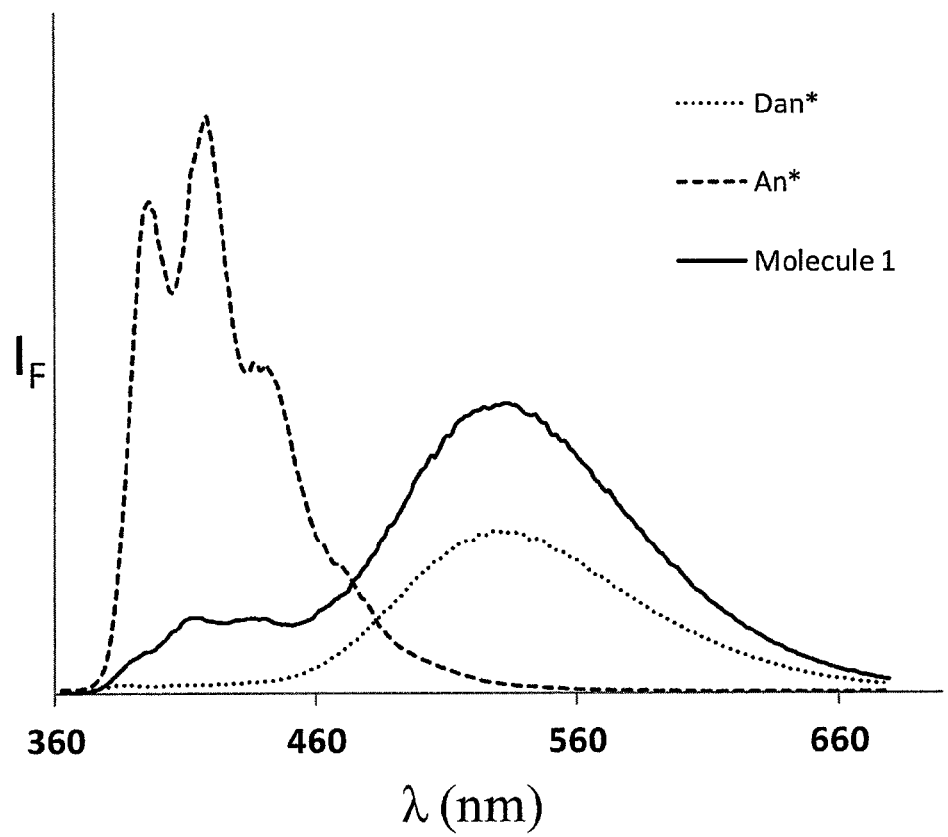
FIG. 4 depicts fluorescence emission spectra of dansyl derivative 7 (Dan*), anthracene derivative 4 (An*) and compound 1 in methanol excited at 345 nm.
Figure 5:
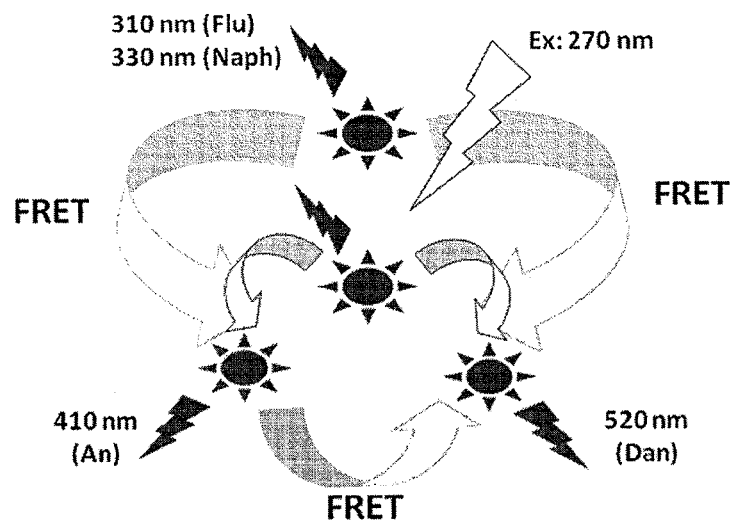
FIG. 5 depicts a schematic representation of the possible FRET processes that can occur among the four fluorophores when excited at 270 nm.

Fluorescence Resonance Energy Transfer (FRET) Between Anthracene and Dansyl:

An equal solution concentration (3.35 µM) of anthracene boronic acid derivative 4 (An*), dansyl boronic derivative 7 (Dan*) and compound 1 in methanol were prepared. The fluorescence spectra of each sample (60 µL) were measured under an excitation wavelength of 345 nm. The enhanced fluorescence emission of the dansyl moiety (540 nm), accompanied by a reduction of emission intensity for the anthracene moiety (385 nm) in compound 1 indicates of FRET between anthracene and dansyl (FIG. 4).

Example 5

Computational Structure of Compound 1

All electronic structure calculations were carried out using GAUSSIAN09 REVISION C.01. Two classes of electronic structure methods were used. Geometries were initially optimized using the semiempirical parameter model 6 (PM6). PM6 should be sufficient to provide qualitative relative energies. Selected geometries were then reoptimized using density functional theory (DFT). For the geometry optimizations, the Perdew-Burke-Emzerhof (PBE) functional was used. Energies were then calculated with Adamo and Barone's hybrid version of this functional (PBE0, also denoted as PBEh or PBE1PBE). Density fitting basis sets (DFBS), as implemented in GAUSSIAN09, were employed in order to improve the computational efficiency of the calculation. Because the use of DFBSs precludes the use of a hybrid DFT exchange-correlation functional, they were used in conjunction with the PBE functional for the geometry optimizations. Due to the rather large size of the system, in order to make the geometry optimizations tractable, the Stuttgart-Dresden effective core potential-basis set was used on all atoms (denoted as SDDall, excluding hydrogen). The single-point energies employed Pople's 6-31G(d,p) basis set. Bulk solvation effects were approximated in the single-point energy calculations using Marenich and Truhlar's solvation model dispersion (SMD), which is an empirical reparamterization of the polarizable continuum model (PCM), specifically the integral equation formalism model (IEF-PCM); methanol was used as the solvent. The accuracy of the DFT methods was improved by adding the empirical dispersion correction as recommended by Grimme. The older version (DFTD2) is available, with analytical gradients and Hessians, in GAUSSIAN09 and was used during geometry optimizations and frequency calculations; the GAUSSIAN09 was Locally Modified to allow for its use for any DFT functional rather than just the limited set included in the commercially available version. The newer, and more accurate, DFTD3 version, which includes parameters for most of the periodic table, was used as an a posteriori correction to the PBE0 energies obtained from GAUSSIAN09; the code written by Grimme was used. All DFT-optimized structures were characterized as minima by having zero imaginary frequencies; small imaginary frequency (<10i cm$^{-1}$) were ignored as artifacts of the large size and flexible nature of the system.

Figure 9:
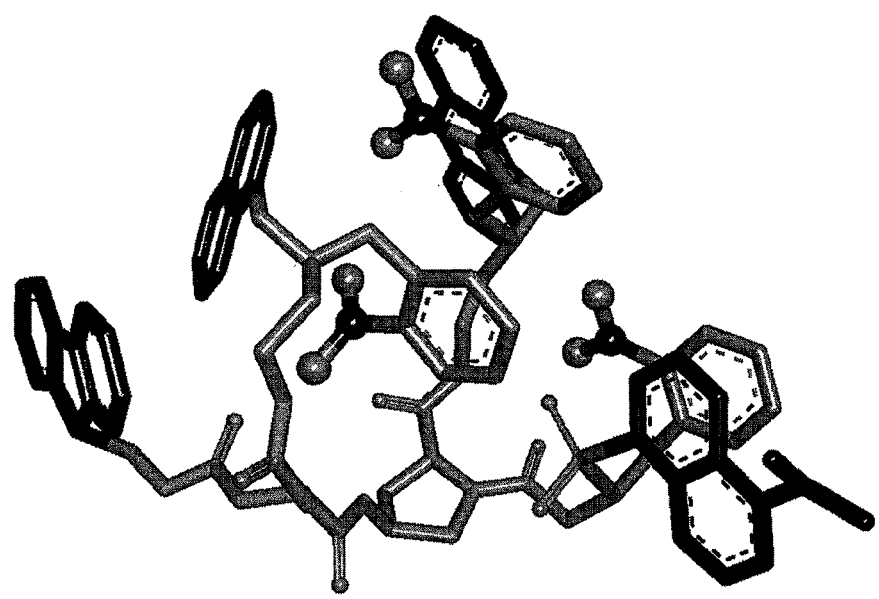
FIG. 9 depicts a DFT optimized structure of compound 1. Color scheme: Grey Stick: Molecular cavity; Black Stick: Four Dyes; Black ball: Boron; Grey ball: Oxygen; Carbon, Nitrogen, Sulphur is not highlighted individually and Hydrogen is omitted for clarity.
Figure 10:
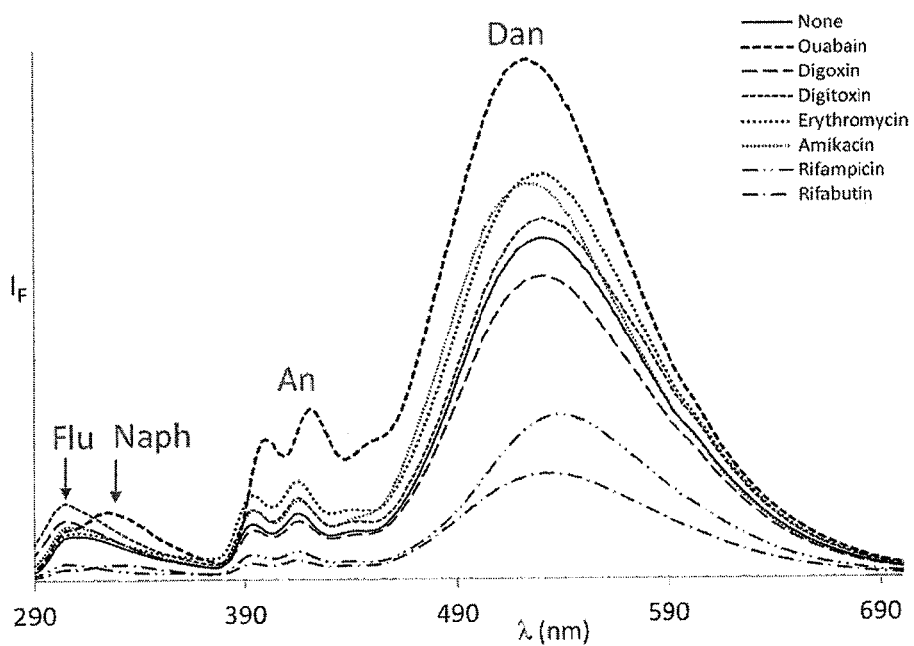
FIG. 10 depicts fluorescence emission spectra of compound 1 (3 µM,) in methanol mixed with antibiotics in DMSO 100 mM. Fluorescence measurements were taken in a 3 mm cuvette under an excitation wavelength of 270 nm using 295-1100 nm emission filter and 10 nm excitation and emission slit width. The spectra were recorded at a rate of 120 nm per min. The emission of the compound 1 (none) corresponds to an addition of only DMSO.

To assess the possibility of such intra-molecular interactions, the structure of compound 1 was simulated using density functional theory (DFT) in a solvent continuum model. The modeling showed that the compound forms a flexible and structurally preorganized cavity in which the three phenyl boronic acids project toward the same direction (FIG. 9) Importantly, the structure was maintained via intra-molecular hydrogen bonds and π-stacking involving the three phenyl boronic acids. For example, the phenyl boronic acid neighboring the dansyl group formed π-interactions with the adjacent aromatic ring (FIG. 9), whereas its hydroxyl groups were hydrogen bonded to an amide and an amine on the neighboring arm as well as to a nearby carbonyl.

Example 6

Fluorescence Measurements of Molecular Differential Sensor of Compound 1 with Antibiotics A solution of molecule 1 (3 μM, 60 μL) in methanol was mixed with a solution of a drug in DMSO (100 mM, 3 μL). The solution mixture was allowed to equilibrate for 6 min. Fluorescence measurements were taken in a 3 mm cuvette under an excitation wavelength of 270 nm using 295-1100 nm emission filter and 10 nm excitation and emission slit width. The spectra were recorded at a rate of 120 nm per min. The emission of the pure sensor (none) corresponds to an addition of only DMSO.

Figure 11:
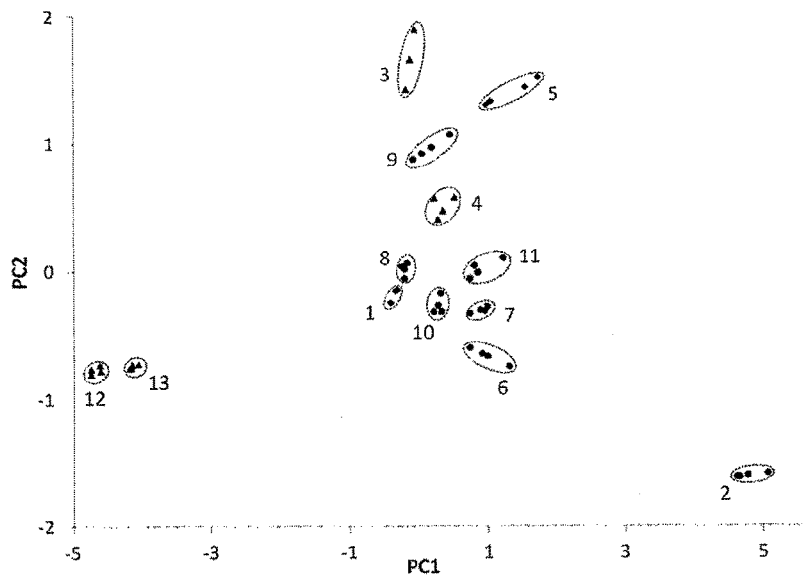
FIG. 11 depicts a principal component analysis (PCA) to distinguish between optical signatures generated by antibiotics such as macrolides, aminoglycosides, cardiac glycosides, and rifamycins, including structures of carbohydrates of this invention.
Figure 11:
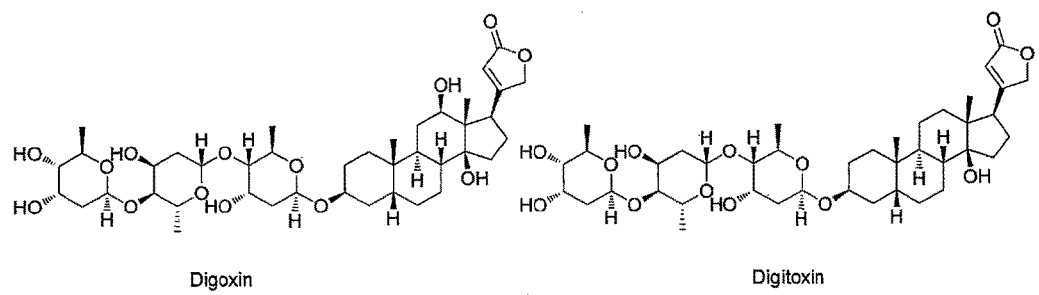

Principal component analysis (PCA) was applied to distinguish between these patterns as well as between optical signatures generated by other macrolides, aminoglycosides, cardiac glycosides, and rifamycins (FIG. 11). Unknown samples were then taken from the training set and PCA was effectively applied to identify their content with an accuracy of 97%.

In such studies, patients are administered a normal dose of rifampicin (e.g. 300 mg) and a much larger amount of the saccharide (e.g. 5 g), as part of a standard D-xylose test used for assessing the absorptive capacity of the intestines.

Figure 12A:
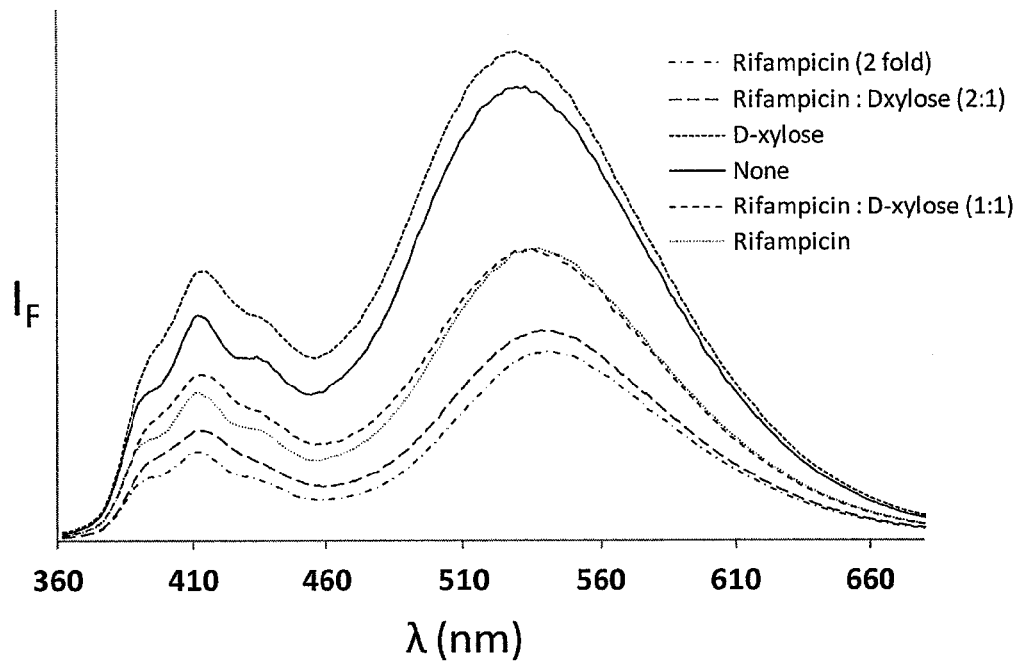
FIG. 12A: Emission Spectra of compound 1 subjected to human urine loaded with different ratios of D-xylose and rifampicin. The parallel analysis of rifampicin and D-xylose levels in urine is used for diagnosing rifampicin malabsorption in patients with tuberculosis.
Figure 12B:
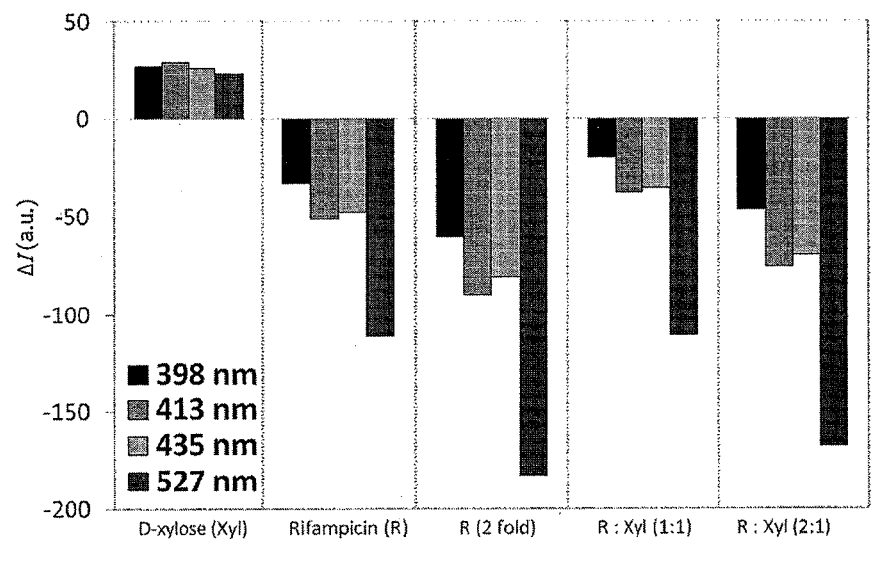
FIG. 12B: Fluorescence response ($\Delta I$) pattern of different drug combinations at four different wavelength
Figure 12C:
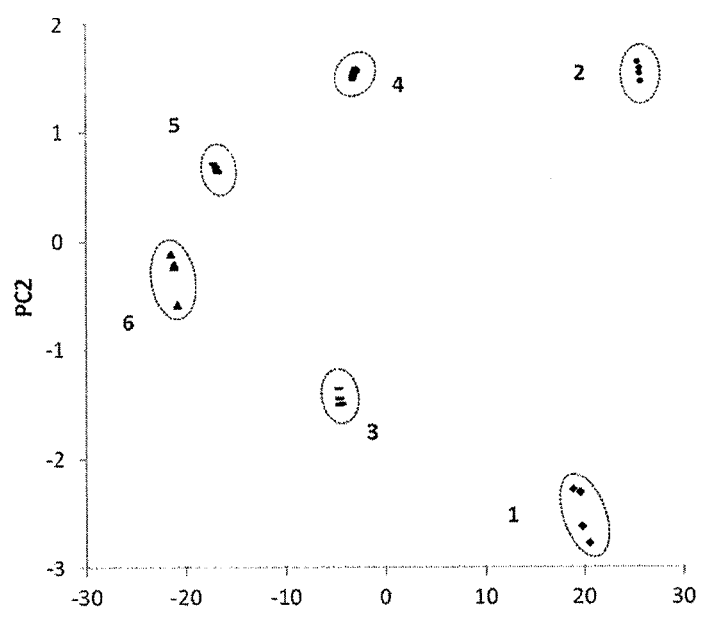
FIG. 12C: PCA mapping of emission experiments.

To test whether the compound of this invention can distinguish between various drug concentrations and combinations within medicinally relevant samples, 1 was subjected to human urine loaded with different ratios of D-xylose and rifampicin. As shown in FIG. 12A, urine samples with just D-xylose or rifampicin induced markedly distinct changes in the emission patterns. Notably, addition of the first resulted in a substantial increase in antharacene fluorescence, whereas the second mainly led to a reduction in dansyl's emission. Similar measurements were performed with urine samples consisting of different antibiotic-saccharide mixtures and PCA was used to differentiate between the patterns generated at the anthracene and dansyl emission region (FIG. 12C). The robustness of the molecular diagnostic system was confirmed by its ability to identify urine-drug samples with a 95% success rate.

Example 7

Preparation of Compound 32 and Other Boronic Acid-Dye Conjugates

Figure 14:
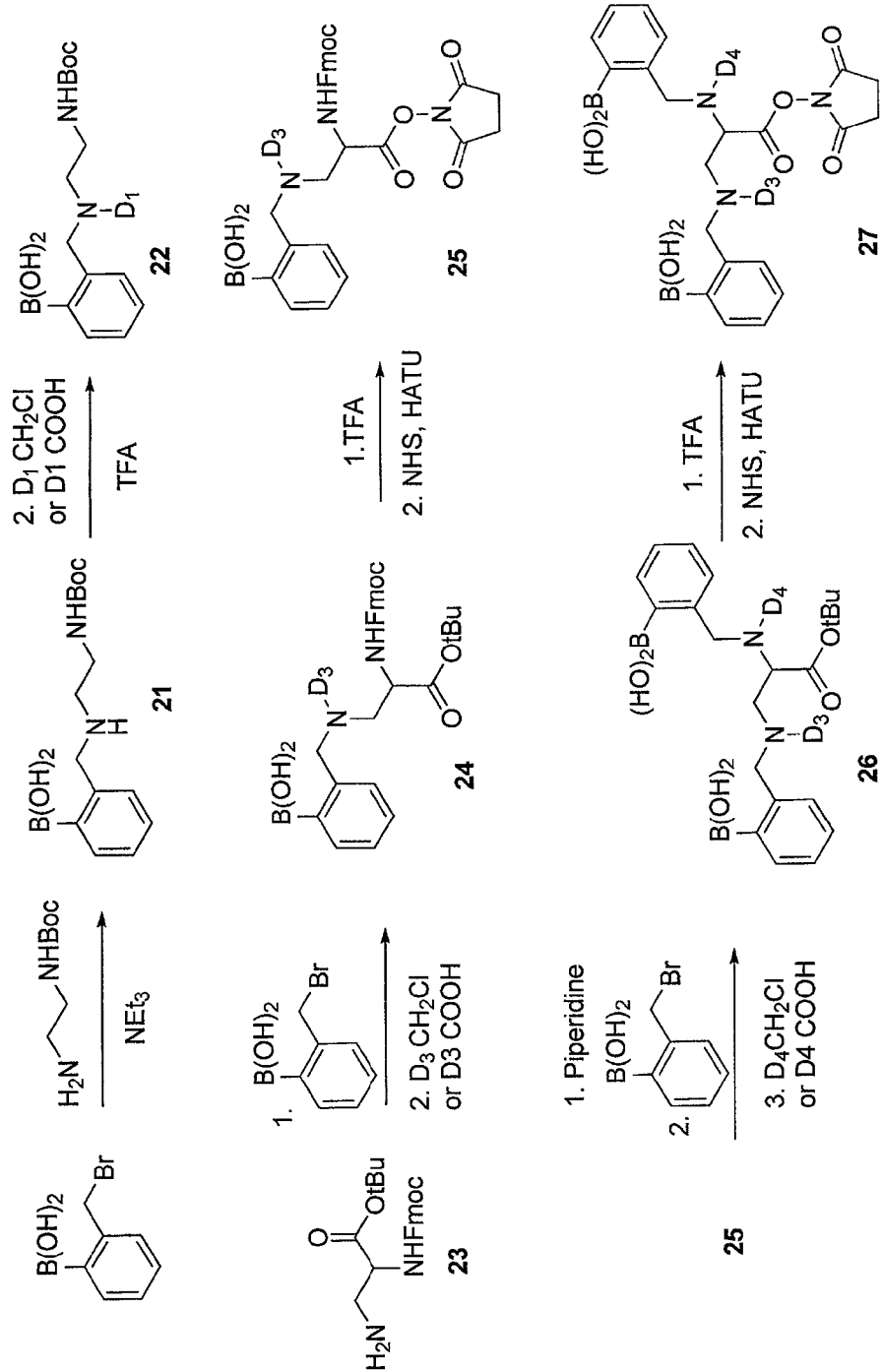
FIG. 14 depicts synthetic steps for preparing various red and NIR emitting boronic acid-dye conjugates.
Figure 15:
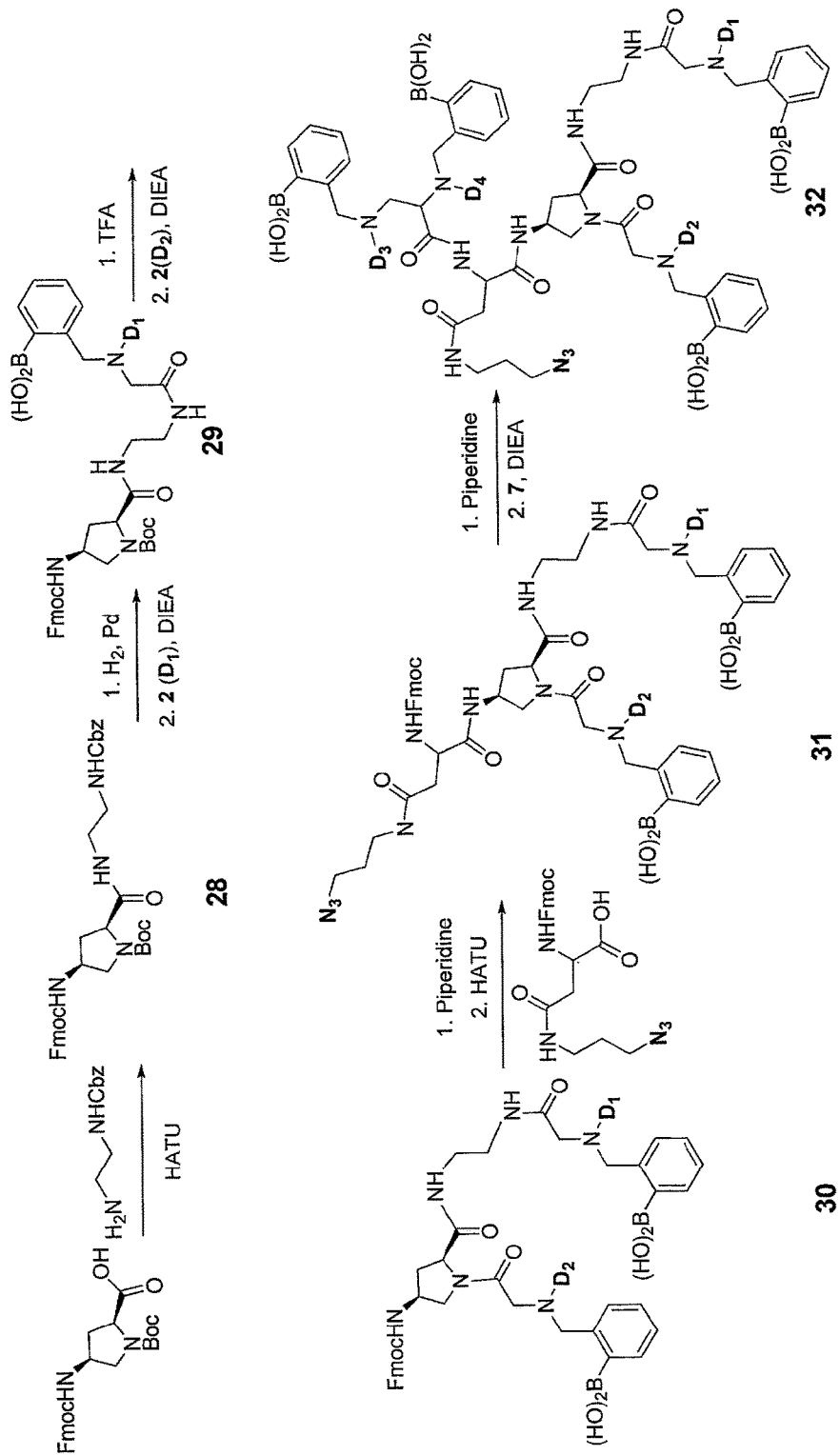
FIG. 15 depicts synthetic steps for preparing a monomolecular combinatorial sensor based on cis-amino proline scaffold, wherein $D_1$ to $D_4$ refer to a chromophore of this invention.

Using the above protocols for preparing various boronic acid-dye conjugates and for attaching them to a single Cis-amino L-proline scaffold, a wide range of boronic acid-dye pairs will initially be prepared from commercially available, carboxy-modified dyes, which emit in the red and NIR spectral regions (FIG. 13, R=OH, NH(CH$_2$)$_2$Br or halide). Lanthanide complexes can also be synthesized to extend the spectral range of the emission patterns. FIG. 14 shows how N-hydroxysuccinimide (NHS) esters (compounds 22 and 27) of a wide range of boronic acid-dye conjugates can be straightforwardly prepared. FIG. 15 shows how the same boronic acid-dye conjugates (compounds 29, 30 and 31) are used for preparing compound 32 (FIG. 15).

The boronic acid-dye conjugates are linked to the Cis amino L-proline via amide bonds. D$_1$, D$_2$, D$_3$ and D$_4$ of FIG. 15 refer to dyes/chromophores of this inventions. Specifically the dyes as depicted in FIG. 13.

Example 8

Two State Molecular Encoding System

Figure 24:
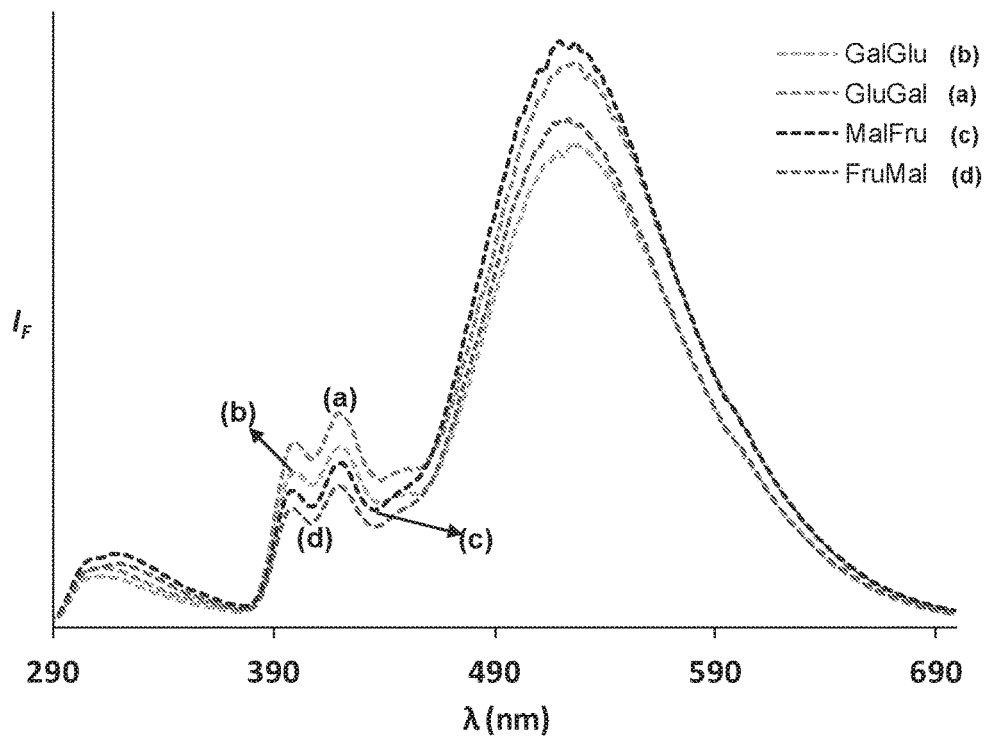
FIG. 24 depicts fluorescence emission spectra of 1 (3 µM) upon a) the addition of $1^{st}$: 2.5 mM D-glucose, $2^{nd}$: 25 mM galactose; b) $1^{st}$: 25 mM galactose, $2^{nd}$: 2.5 mM D-glucose; c) $1^{st}$: 25 mM maltitol, $2^{nd}$: 2.5 mM D-fructose, d) $1^{st}$: 2.5 mM D-fructose, $2^{nd}$: 25 mM maltitol in methanol. Excitation wavelength: 270 nm.

A series of two state molecular encoding system that respond to different sequences of saccharide pairs, such as D-glucose (G) and D-xylose (X), D-glucose (G) and galactose (L), as well as D-fructose (F) and maltitol (M) (FIG. 17a and FIG. 24) were prepared. The distinct optical signatures observed for inputs GX and XG (FIG. 17a), GL and LG, and FM and MF (FIG. 24) is an example for an encoding system of this invention using 2-input analytes. FIG. 18 exemplifies how the strong binding of the first saccharide (i.e., saccharide 1 or 2) to two of the three boronic acids (i.e., complexes ii and iii) followed by a weaker binding of the second saccharide can impose the formation of a metastable complex (i.e., complex iv or v) whose conversion to the thermodynamic product occurs over a prolonged reaction time.

Figures 17A, 17B:
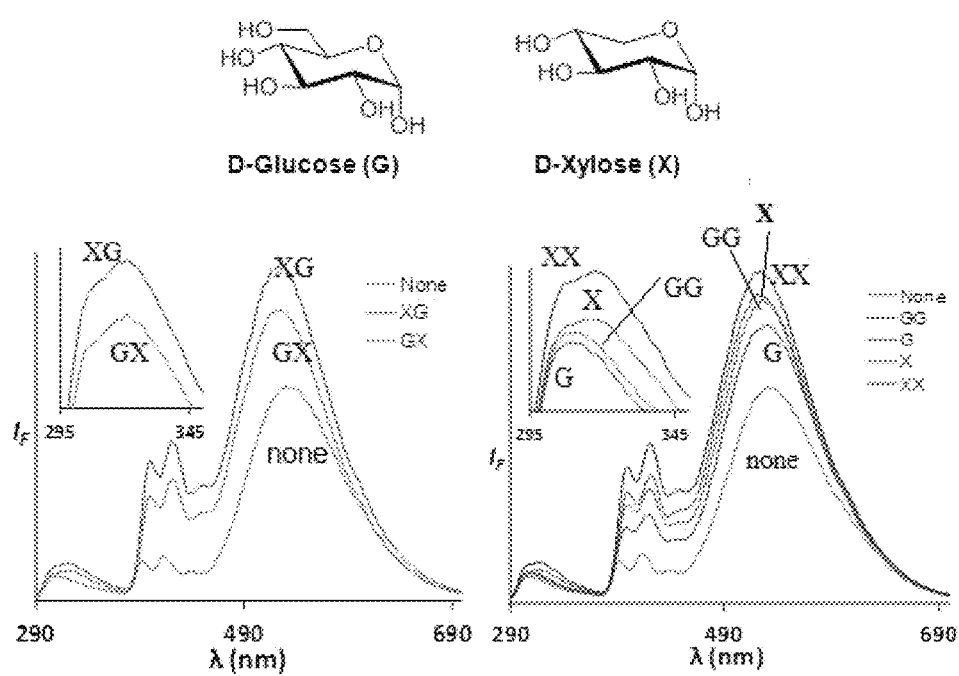
FIG. 17 depicts emission spectra of molecule 1 (3 µM) upon addition of D-glucose (G) (2.5 mM) and D-xylose (X) (25 mM) in different order (a), and at different concentrations (b). Excitation wavelength: 270 nm.

The encoding system of this invention differentiate between 'passwords' of different inputs (i.e analytes) or different ratios/concentrations of the same input (FIG. 17b). The different emission patterns obtained upon addition of each saccharide (X=D-xylose or G=D-glucose), followed by a second addition of the same input signal (XX or GG), confirm that compound 1 can recognize X, G, XX, and GG as distinct code entries. FIG. 18 illustrates how such changes could result in distinguishable emission pattern. Specifically, passwords (i.e inputs) 1, 2, 11, 22, 12, 21 can be differentiated because different saccharides (i.e., 1 or 2) induce the formation of distinct complexes (i.e., ii and vi or iii and vii), while their concentration affects the ratio between them. Principal component analysis (PCA) (FIG. 19) of the complete spectral data (FIGS. 17a and 17b) proves that an individual fluorescent molecule discriminated between all possible combinations of 1- and 2-code entries, namely, X, G, XX, GG, XG and GX, akin to an equivalent electronic device.

Example 9

Three State Molecular Encoding System Consisting of Different Combination of 3-Inputs FIG. 20 includes 27 code entries, and many of them should be readily differentiated by the encoding system of this invention. In FIG. 20, each digit (1, 2 or 3) represents a different chemical input and the 27 combinations are divided to 10 password groups (FIG. 20, groups a-j) that differ either in the type of inputs 'keys' or in the ratio between them. Because compound 1 can effectively differentiate between different chemical inputs and between distinct input concentrations (FIG. 17b), many of the passwords (inputs) that belong to different groups (a-j) should be distinguished. In addition, the ability of compound 1 to discriminate between input sequences (FIG. 17a and FIG. 26) should allow it to differentiate passwords within each group (e.g. groups d-i). For example, passwords (11)2 and 2(11) in group should induce the formation of distinct optical fingerprints.

Figure 21A:
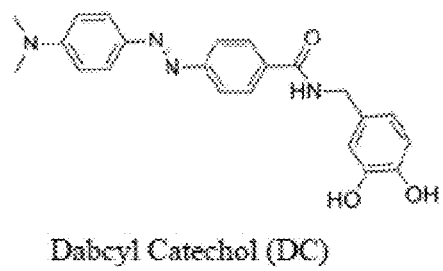
FIG. 21 depicts a) the structure of DC; b) the change in fluorescence spectrum of compound 1 (9 µM) upon addition of maltitol (50 mM), D-xylose (17 mM) and DC (125 µM); (c) the displacement of DC by D-xylose (X); (d) the fluorescence response ($\Delta I$) of different two state encoding system using DC, D-xylose (X) and maltitol (M) as inputs. Excitation: 270 nm.
Figure 21B:
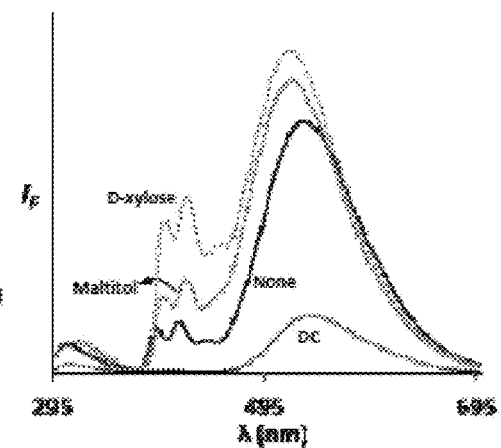
Figure 21C:
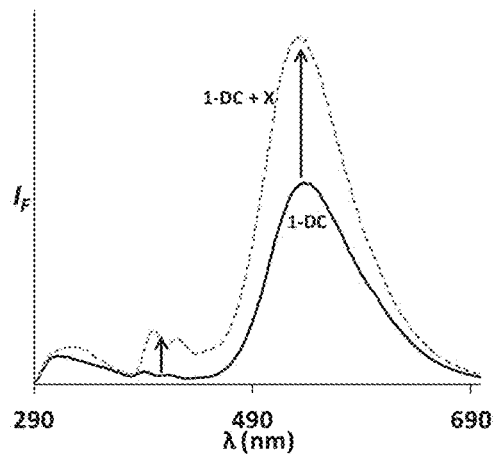
Figure 21D:
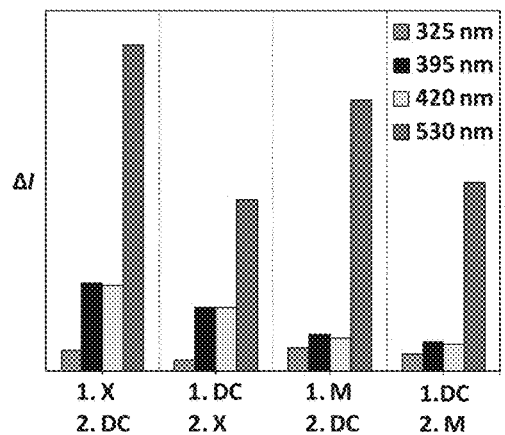

To efficiently discriminate between groups a-j (FIG. 20), chemical inputs and different concentrations that, individually, induce the most distinguishable changes to the emission signal was first screened. In addition to testing 12 different saccharides (FIG. 26), a new chemical input that integrates catechol and dabcyl functionalities (FIG. 21a, DC) was synthesized (Example 10). The strong affinity of catechol to boronic acids and the ability of dabcyl to quench the emission of various fluorphores enables DC to compete with the binding of various saccharides, as well as to generate markedly distinct emission patterns. As shown in FIG. 21b, maltitol, D-xylose, and DC, which were selected from this screen, generated entirely different patterns and the addition of DC has indeed led to fluorescence quenching across the UV-Vis spectrum. Moreover, the fluorescence emission was resorted upon adding competing saccharides (FIG. 21c) and the resulting optical fingerprints were dependent on the order of addition (FIG. 21d).

Example 10

Synthesis of Compound 35 (Dabcyl Catechol (DC)

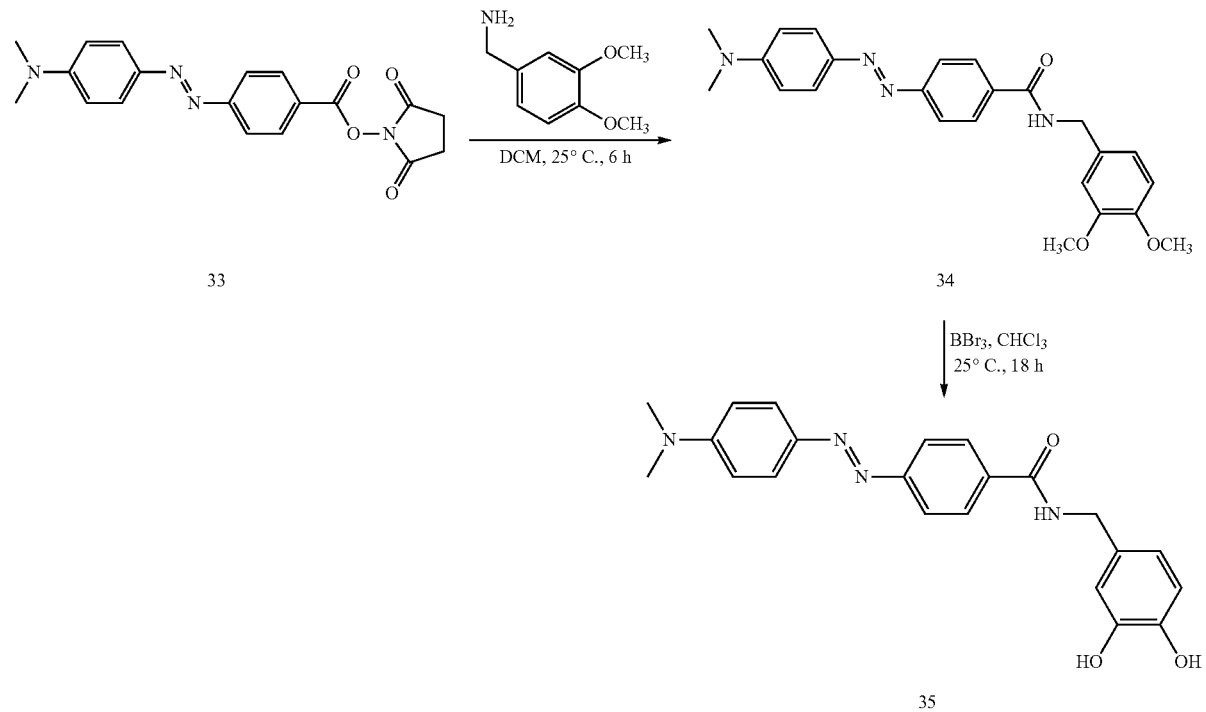

Synthesis of Compound 34:

To a stirred solution of DABCYL-NHS 33 (0.25 g, 0.068 mmol) in dry DCM (1.5 mL) was added 3,4-Dimethoxy benzylamine (0.011 g, 0.068 mmol) under argon. The reaction mixture was stirred at room temperature for 6 h. The solvent was evaporated and the crude reaction mass was subjected to combi-flash column chromatography (silica gel, 1% methanol in DCM) to afford 34 (0.20 g) as red solid in 70% yield. $^1$H NMR (300 MHz, CDCl$_3$) 3.10 (6H, s), 3.87 (6H, s), 4.59 (2H, d, J=6 Hz), 6.48 (1H, s, br), 6.75 (2H, d, J=9 Hz), 6.84 (1H, d, J=9 Hz), 6.90 (2H, s), 7.87 (6H, s); MS (ESI+): m/z (%)=419.31 (100) [M+H]$^+$, 441.31 (75) [M+Na]$^+$, 859.52 (60) [2M+Na]$^+$, 1277.80 (25) [3M+Na]$^+$.

Synthesis of Compound 35:

To a stirred solution of 34 (0.20 g, 0.047 mmol) in dry DCM (1.5 mL) was added boron tribromide (0.1 g, 0.4 mmol, 400 µL of 1M solution of BBr$_3$) under argon at 0° C. The solution was warmed to room temperature and then stirred for 18 h. The reaction was diluted with DCM (25 mL) and washed with saturated solution of NaHCO$_3$ (2×5 mL). The organic layer was washed with brine (5 mL) and dried over anhydrous Na$_2$CO$_3$. The solvent was evaporated and the crude reaction mass was subjected to combi-flash column chromatography (silica gel, 4% methanol in DCM) to afford 35 (0.014 g) as red solid in 76% yield. $^1$H NMR (300 MHz, CDCl$_3$) 3.10 (6H, s), 4.45 (2H, s), 6.67-6.75 (2H, m), 6.80 (3H, d, J=9 Hz), 7.81-7.85 (4H, m), 7.94 (2H, d, J=9 Hz); MS (ESI+): m/z (%)=391.28 (65) [M+H]$^+$, 413.28 (45) [M+Na]$^+$, 803.49 (40) [2M+Na]$^+$.

Example 11

Three-State Molecular Encoding System

Figure 22A:
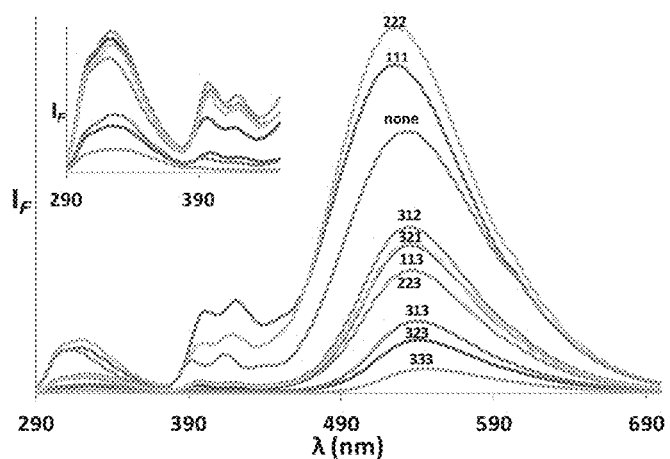
FIG. 22 depicts a) fluorescence spectra of compound 1 (9 µM) upon addition of maltitol (1), D-xylose (2), and DC (3) in nine different combinations; and b) the corresponding PCA plot. Excitation wavelength=270 nm.
Figure 22B:
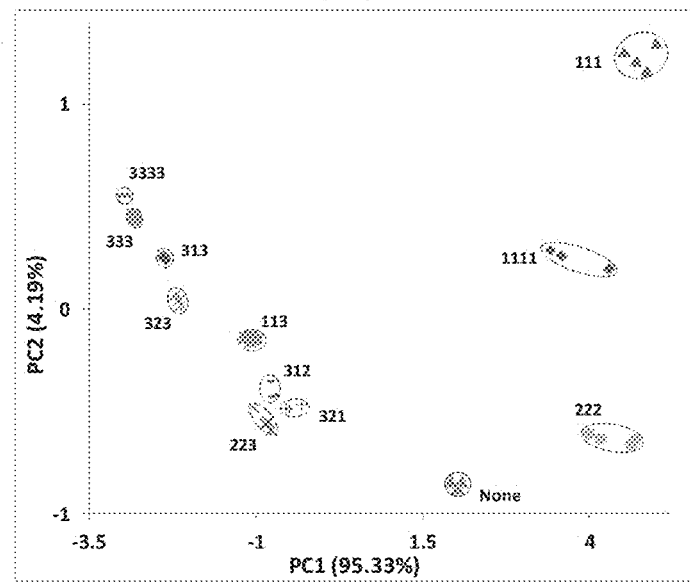
Figure 26:
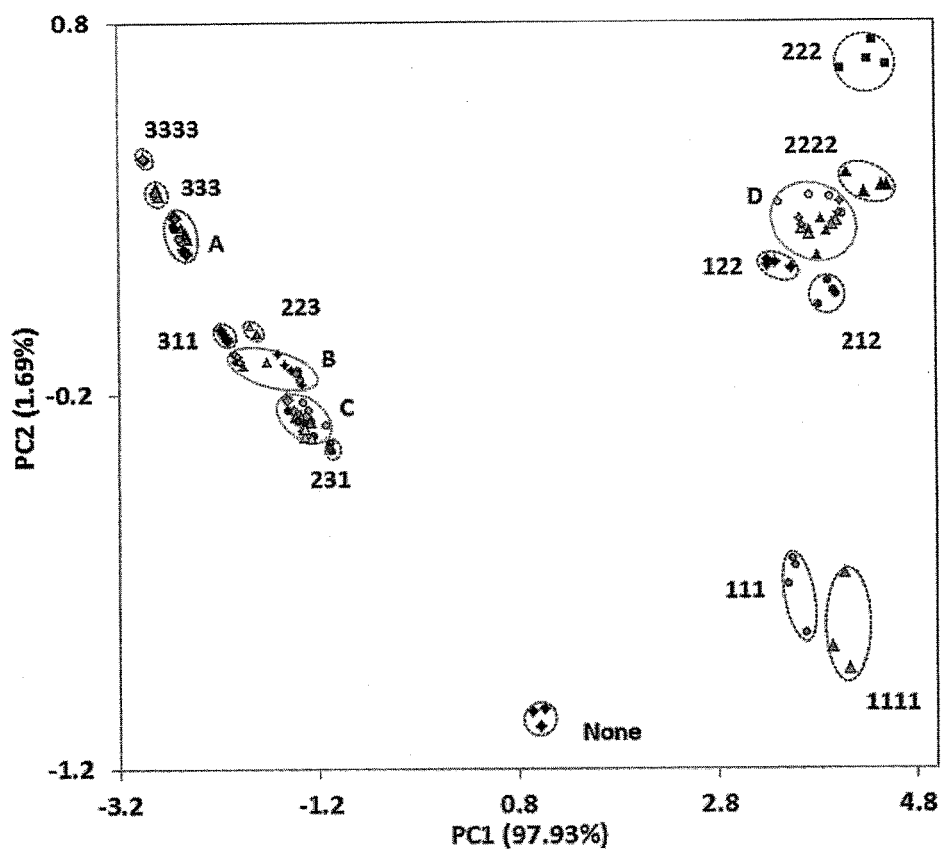
FIG. 26 depicts a PCA mapping of emission patterns generated by 50 mM maltitol (1), 17 mM D-xylose (2) and 125 µM DC (3) in twenty seven different combinations. A, B, C, D are the groups containing passwords that match each other, Group A contains 133, 331, 313, 233, 332, 323; Group B contains 113, 131, 322, 232; Group C contains 213, 123, 132, 312, 321; and Group D contains 221, 112, 211, 121.

A three state encoding system of this invention was prepared using of 1. maltitol, 2. D-xylose, and 3. DC as input signals. FIG. 22a shows some of the patterns generated by 'inputs 1 to 3. Pattern analysis of all 27 combinations (FIG. 20) reveals that nine 3-digit passwords can be authorized by the unimolecular security system (FIG. 22b). The feasibility of distinguishing 4-digit code entries such as, 1111, 2222, and 3333, was also demonstrated (FIG. 26). Because patterns generated from repeats of identical chemical inputs are unique; these 4-digit 'passwords' should also be distinguished from the 81 possible 4-digit combination codes (i.e, $3^4$=81).

Example 12

Fluorescence Measurements

Analysis of Two State Passwords

Figure 19:
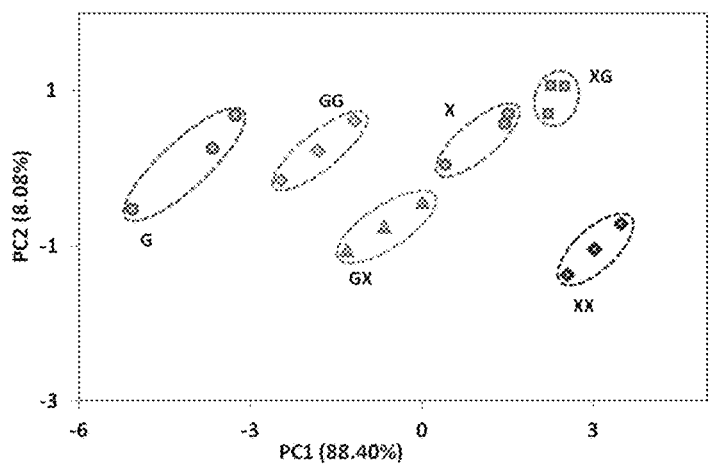
FIG. 19 depicts a PCA mapping of emission patterns generated by compound 1 upon addition of D-glucose (G) and D-xylose (X) in different sequences and concentrations.

Saccharides (1.5 µL) were added to a solution of 1 (3 µM, 60 µL) in methanol (FIG. 17). The mixture was allowed to equilibrate for 6 min after each saccharide addition. Fluorescence measurements were taken in a 3 mm cuvette using an excitation wavelength of 270 nm, an emission filter of 295-1100 nm and excitation and emission slit width of 10 nm. The spectra were recorded at a rate of 120 nm per min. A solution of 1 M D-xylose and 100 mM of D-glucose were used for measurements of two input passwords (FIGS. 17 and 19). The emission of the pure sensor (none) corresponds to addition of pure water.

Analysis of Saccharide and Three State Passwords

A solution of a saccharide or analyte (1 µL) was added to a solution of 1 (3 µM, 60 µL) in methanol (FIG. 21b). The mixture was allowed to equilibrate for 6 min after each addition. Fluorescence measurements were taken in a 3 mm cuvette using an excitation wavelength of 270 nm, 295-1100 nm emission filter and 10 nm excitation and emission slit width. A solution of 3 M Maltitol in water, 1 M D-glucose in water and 7.7 mM DC in methanol were used for the measurements of three input passwords (FIGS. 21 and 22). The spectra were recorded at a rate of 120 nm per min. The emission of the pure sensor (none) corresponds to addition of pure water.

Saccharide Detection

Figure 25:
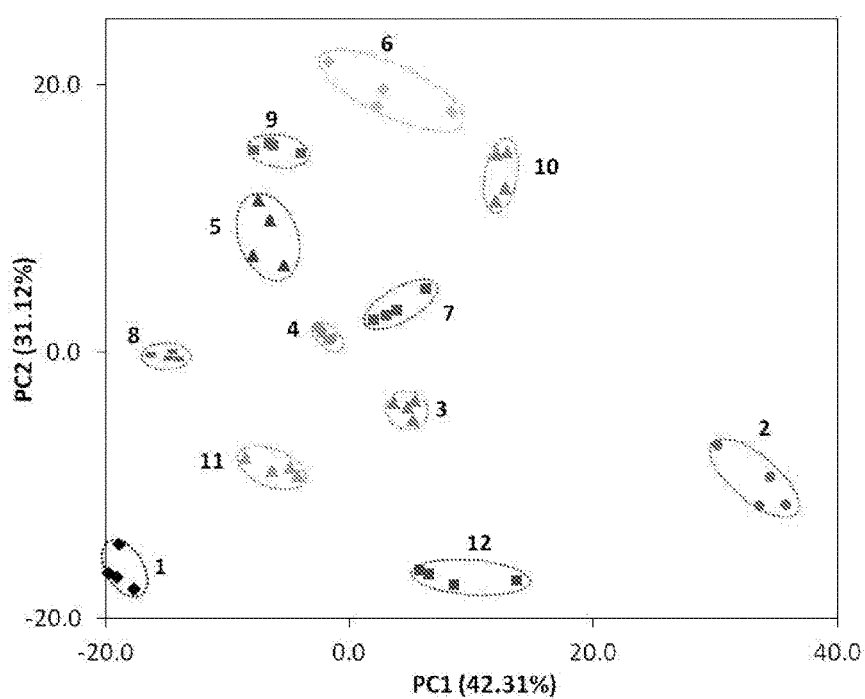
FIG. 25 depicts a PCA mapping of emission patterns generated by 5 mM solution of various saccharides. 1) None; 2) D-glucose; 3) L-glucose; 4) D-fructose; 5) L-fructose; 6) D-xylose; 7) L-xylose; 8) mannitol; 9) maltitol; 10) lactulose; 11) D-maltose; 12) maltotriose.

A solution of a saccharide (3 µL, 100 mM) was added to a solution of 1 (3 µM, 60 µL) in methanol (FIG. 25). The mixture was allowed to equilibrate for 6 min. Fluorescence measurements were taken in a 3 mm cuvette under an excitation wavelength of 270 nm using 295-1100 nm emission filter and 10 nm excitation and emission slit width. The spectra were recorded at a rate of 120 nm per min. The emission of the pure sensor (none) corresponds to an addition of only water.

Example 13

Principal Component Analysis (PCA)

The fluorescence experiments were performed in four replicates for all the saccharides and PCA was applied to distinguish between patterns generated by the fluorescence intensities at wavelengths ranging from 295 nm to 700 nm (FIG. 25).

Similarly, differentiation between D-xylose and D-glucose combinations and concentrations (FIG. 19) was achieved by analyzing emission intensities at seven different wavelengths (e.g. 304 nm, 326 nm, 397 nm, 421 nm, 449 nm, 496 nm and 527 nm). The analysis of three input passwords was done at eight different wavelengths (e.g. 305 nm, 325 nm, 395 nm, 420 nm, 445 nm, 520 nm, 530 nm and 540 nm). Principal component analysis of the emission spectra was performed using XLSTAT version 2013.1.01 (32 bit).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A compound comprising an array of at least three chromophores, at least one receptor and an anchor, wherein binding said receptor to an analyte results in a unique optical signature; wherein said receptor is a boronic acid receptor, wherein said anchor is cis-amino L proline, trans-amino-L proline, cis-amino-D L proline or trans-amino-D proline and wherein said chromophore is attached to said anchor via a linker, wherein said linker comprises nitrogen.

2. The compound of claim 1, wherein said at least three chromophores are the same or different.

3. The compound of claim 1, wherein said chromophore is naphthalene, anthracene, fluorenyl, dansyl or any combination thereof.

4. The compound of claim 1, wherein said receptor is phenyl boronic acid.

5. The compound of claim 1, wherein said analyte is antibiotic selected from: macrolides, aminoglycosides, cardiac glycosides or rifamycins; or carbohydrate selected from: L-Glucose, D-Glucose, D-fructose, L-fructose, D-arabinose, D-xylose, L-xylose, L-mannose, D-galactose, D-sorbitol, mannitol, dulcitol, adonitol, xylitol, L-threitol, maltitol, lactulose, D-lactose, D-maltose, D-trehalose or maltotriose.

6. The compound of claim 1, wherein said compound is represented by the following structure 1:

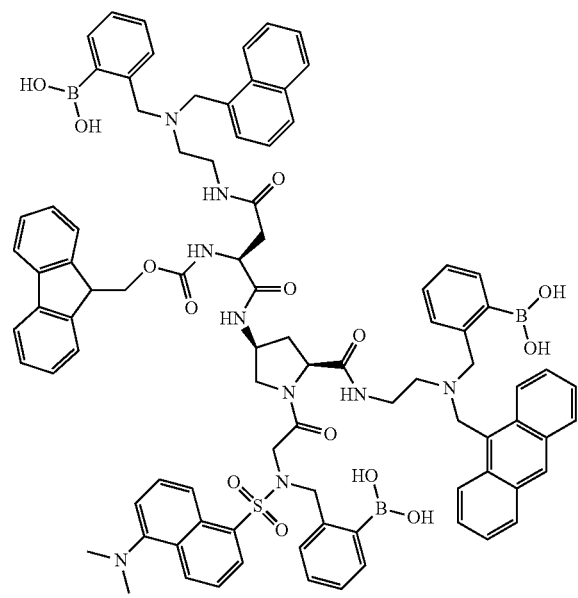

(1)

7. The compound of claim 1, wherein a first fluorescent dye emits at a wavelength which is the absorption wavelength of a second fluorescent dye.

8. The compound of claim 1, wherein a first fluorescent dye is naphthalene, fluorenyl or combination thereof, wherein said first fluorescent dye emits light at a wavelength of between 300-370 nm following excitation at 270 nm; wherein said second fluorescent dye is dansyl, anthracene or combination thereof, wherein said second fluorescent dye absorbs at a range of between 300 to 400 nm.

9. A method of differentiating between carbohydrates comprising:
contacting a carbohydrate with a compound in a liquid medium, wherein said carbohydrate and said compound form a complex; wherein said compound comprises an array of at least three chromophores, at least one boronic acid receptor and an anchor; wherein said anchor is cis-amino-L proline, trans-amino-L proline, cis-amino-D proline or trans-amino-D proline and wherein said chromophore is attached to said anchor via a linker, wherein said linker comprises nitrogen; wherein contacting said carbohydrate with said compound results in a conformational change of said compound and thereby to a unique optical signature of said complex; and measuring the optical signature of said complex;
and thereby, differentiating said carbohydrate.

10. The method of claim 9, wherein said chromophore is naphthalene, anthracene, fluorenyl, dansyl or any combination thereof.

11. The method of claim 9, wherein said carbohydrate is antibiotic or a saccharide, wherein said saccharide is L-Glucose, D-Glucose, D-fructose, L-fructose, D-arabinose, D-xylose, L-xylose, L-mannose, D-galactose, D-sorbitol, mannitol, dulcitol, adonitol, xylitol, L-threitol, maltitol, lactulose, D-lactose, D-maltose, D-trehalose or maltotriose; wherein said antibiotic is macrolides, aminoglycosides, cardiac glycosides, or rifamycins.

12. The method of claim 9, wherein said receptor is phenyl boronic acid.

13. The method of claim 9, wherein said compound is represented by the following structure 1:

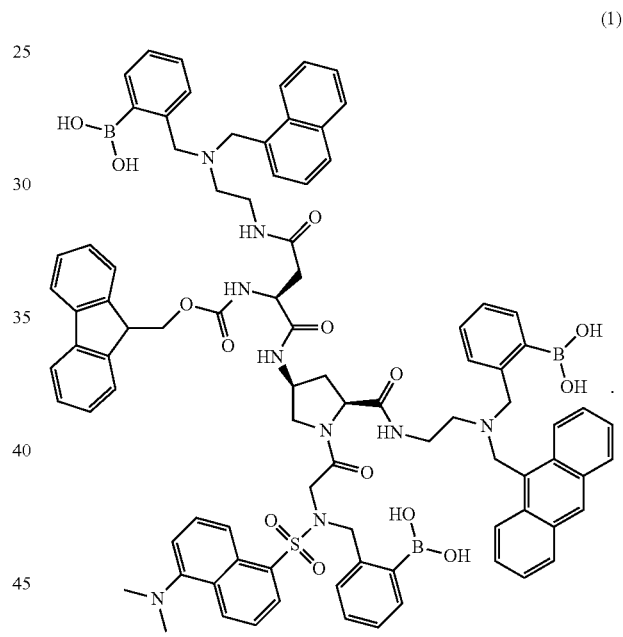

(1)

14. The method of claim 9, wherein said unique optical signature is a fluorescence pattern of said complex; and said fluorescence pattern is obtained followed irradiation of said complex at a wavelength that at least one of said fluorescent dye is excited.

15. The method of claim 14, wherein said fluorescence pattern indicates the presence of at least one carbohydrate in said medium.

16. The method of claim 9, wherein said liquid medium is an aqueous solution.

17. The method of claim 9, wherein said carbohydrate is a component of a glycoprotein, a proteoglycan or a glycolipid.

18. The method of claim 11, wherein said saccharide is a monosaccharide, a disaccharide or a glycan independent of a protein or lipid compound.

19. A method of diagnosing a disease in a subject, wherein said diagnosis comprises detection of a carbohydrate biomarker; said method comprising:

collecting a biological sample from a subject;

optionally isolating components from said biological sample;

contacting a compound with a carbohydrate comprised within said sample or isolated component in a liquid medium; wherein said carbohydrate forms a complex with said compound; wherein said compound comprises an array of at least three chromophores, at least one boronic acid receptor and an anchor; wherein said anchor is cis-amino-L proline, trans-amino-L proline, cis-amino-D proline or trans-amino-D proline and wherein said chromophore is attached to said anchor via a linker, wherein said linker comprises nitrogen; wherein contacting said compound with said carbohydrate results in a conformational change of said compound and thereby to a unique optical signature of said complex;

measuring the optical signature of said complex;

identifying a carbohydrate biomarker in said sample, said carbohydrate biomarker being characteristic of a disease; or measuring a change in a concentration of a carbohydrate biomarker in said sample compared to normative values, wherein said change is characteristic of a disease;

thereby, diagnosing a disease in a subject.

20. The method of claim 19 wherein said chromophore is naphthalene, anthracene, fluorenyl, dansyl or any combination thereof.

21. The method of claim 19 wherein said carbohydrate is L-Glucose, D-Glucose, D-fructose, L-fructose, D-arabinose, D-xylose, L-xylose, L-mannose, D-galactose, D-sorbitol, mannitol, dulcitol, adonitol, xylitol, L-threitol, maltitol, lactulose, D-lactose, D-maltose, D-trehalose or maltotriose.

22. The method of claim 19 wherein said receptor is phenyl boronic acid.

23. The method of claim 19 wherein said compound is represented by the following structure 1:

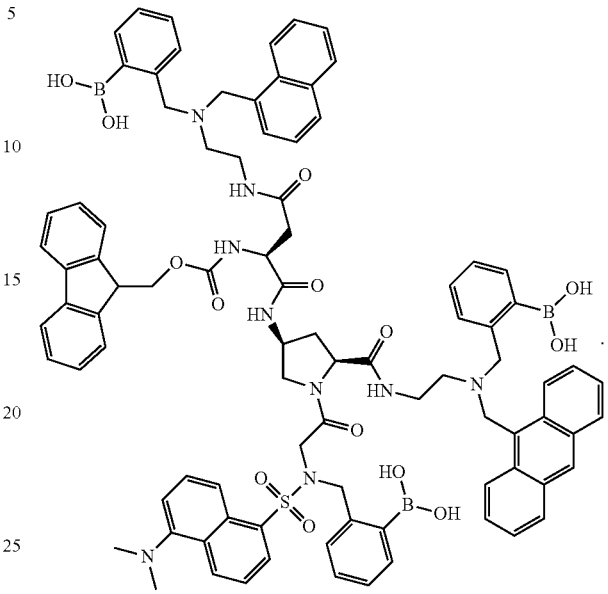

(1)

24. The method of claim 19 wherein said unique optical signature is a fluorescence pattern of said complex; and said fluorescence pattern is obtained followed irradiation of said complex at a wavelength that at least one of said fluorescent dye is excited.

25. The method of claim 19 wherein said disease is selected from hypoglycemia, prostate cancer, diabetes, syndrome X or a glycoprotein based disease selected from multiple sclerosis, crohn's disease, autoimmune disease, colitis, inflammatory bowel disease, cancer, lysosomal storage disease, or celiac.

26. The method of claim 19, wherein said carbohydrate biomarker is a component of a glycoprotein, a glycolipid or a proteoglycan.

27. The method of claim 19, wherein said carbohydrate biomarker is a monosaccharide, a disaccharide or a glycan independent of a protein or lipid molecule.

* * * * *